US012636173B2

(12) United States Patent
Falco et al.

(10) Patent No.: US 12,636,173 B2
(45) Date of Patent: May 26, 2026

(54) MEDICAL IMPLANT DELIVERY SYSTEM AND RELATED METHODS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Kevin M. Falco, Chelmsford, MA (US); Jeffrey L. Barnes, Medford, MA (US); Aaron M. Burke, Andover, MN (US); Carolyn M. Krasniak, Melrose, MA (US); Nathaniel Van Tran, Lakeville, MN (US); Nathaniel Zenz-Olson, Ham Lake, MN (US); Justin A. Callaway, Goffstown, NH (US); Cori G. Pierce, Salem, NH (US); Jessica M. Grabinsky, Melrose, MA (US); Rachel Sophia Keen, Andover, MA (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 635 days.

(21) Appl. No.: 17/986,570

(22) Filed: Nov. 14, 2022

(65) Prior Publication Data

US 2023/0097234 A1 Mar. 30, 2023

Related U.S. Application Data

(63) Continuation of application No. PCT/US2021/038198, filed on Jun. 21, 2021.

(Continued)

(51) Int. Cl.
*A61B 17/128* (2006.01)
*A61F 2/95* (2013.01)

(52) U.S. Cl.
CPC ........ *A61F 2/9517* (2020.05); *A61B 17/1285* (2013.01)

(58) Field of Classification Search
CPC . A61B 17/128; A61B 17/1285; A61B 17/068; A61B 17/0682; A61B 2017/0688;
(Continued)

(56) References Cited

U.S. PATENT DOCUMENTS

| | | | |
|---|---|---|---|
| 3,650,453 A | 3/1972 | Smith, Jr. | |
| 4,043,504 A | 8/1977 | Hueil et al. | |

(Continued)

*Primary Examiner* — Linda J. Hodge
(74) *Attorney, Agent, or Firm* — Seager, Tufte & Wickhem LLP

(57) ABSTRACT

An implant delivery system including a fixation member delivery system including an elongate shaft, first and second rails, a plurality of fixation members with each fixation member slidably disposed on the first and second rails and an actuation assembly. The actuation assembly includes a first elongate member including a first plurality of engagement members disposed along the first elongate member with a distal end region of each engagement member in engagement with one of the fixation members, a second elongate member including a second plurality of engagement members disposed along the second elongate member with a distal end region of each engagement member in engagement with one of the fixation members. Additionally, cyclical actuation of the actuation assembly is configured to incrementally move the fixation members distally along the first and second rails to deploy each of the plurality of fixation members in sequence.

15 Claims, 49 Drawing Sheets

Related U.S. Application Data

(60) Provisional application No. 63/042,196, filed on Jun. 22, 2020, provisional application No. 63/042,160, filed on Jun. 22, 2020, provisional application No. 63/042,174, filed on Jun. 22, 2020, provisional application No. 63/042,197, filed on Jun. 22, 2020.

(58) Field of Classification Search
CPC .............. A61B 17/064; A61B 17/0642; A61B 2017/0646; A61F 2/9517; A61F 2/0811
USPC .................... 227/175.1, 179.1; 606/142, 143
See application file for complete search history.

(56) References Cited

U.S. PATENT DOCUMENTS

| | | | |
|---|---|---|---|
| 4,403,693 A | | 9/1983 | Froehlich |
| 4,430,997 A | * | 2/1984 | DiGiovanni ......... A61B 17/128 |
| | | | 606/143 |
| 4,454,875 A | | 6/1984 | Pratt et al. |
| 4,478,362 A | | 10/1984 | Foslien |
| 4,509,518 A | * | 4/1985 | McGarry ............. A61B 17/128 |
| | | | 606/143 |
| 4,523,707 A | | 6/1985 | Blake, III et al. |
| 4,527,726 A | | 7/1985 | Assell et al. |
| 4,618,086 A | | 10/1986 | Li et al. |
| 4,787,387 A | | 11/1988 | Burbank, III et al. |
| 4,951,860 A | | 8/1990 | Peters et al. |
| 5,038,991 A | | 8/1991 | Thornton |
| 5,049,152 A | * | 9/1991 | Simon ................ A61B 17/1285 |
| | | | 606/139 |
| 5,089,009 A | | 2/1992 | Green |
| 5,114,065 A | | 5/1992 | Storace |
| 5,170,926 A | | 12/1992 | Ruckdeschel et al. |
| 5,258,010 A | | 11/1993 | Green et al. |
| 5,725,554 A | | 3/1998 | Simon et al. |
| 5,911,353 A | | 6/1999 | Bolanos et al. |
| 6,277,131 B1 | | 8/2001 | Kalikow |
| 6,352,541 B1 | | 3/2002 | Kienzle et al. |
| 6,767,356 B2 | * | 7/2004 | Kanner ................ A61B 17/068 |
| | | | 606/220 |
| 7,473,258 B2 | | 1/2009 | Clauson et al. |
| 7,530,484 B1 | | 5/2009 | Durrani |
| 7,533,790 B1 | | 5/2009 | Knodel et al. |
| 7,753,250 B2 | | 7/2010 | Clauson et al. |
| 7,926,692 B2 | | 4/2011 | Racenet et al. |
| 7,954,683 B1 | | 6/2011 | Knodel et al. |
| 7,963,432 B2 | | 6/2011 | Knodel et al. |
| 8,056,789 B1 | | 11/2011 | White et al. |
| 8,066,720 B2 | | 11/2011 | Knodel et al. |
| 8,220,690 B2 | | 7/2012 | Hess et al. |
| 8,240,538 B1 | | 8/2012 | Manoux |
| 8,261,958 B1 | | 9/2012 | Knodel |
| 8,317,072 B1 | | 11/2012 | Knodel et al. |
| 8,465,501 B2 | * | 6/2013 | Matsuoka .......... A61B 17/1222 |
| | | | 606/157 |
| 8,602,286 B2 | | 12/2013 | Crainich et al. |
| 8,733,616 B2 | | 5/2014 | Bailly et al. |
| 8,870,049 B2 | | 10/2014 | Amid et al. |
| 8,939,343 B2 | | 1/2015 | Milliman et al. |
| 9,027,819 B2 | | 5/2015 | Euteneuer et al. |
| 9,095,337 B2 | | 8/2015 | Euteneuer et al. |
| 9,125,650 B2 | | 9/2015 | Euteneuer et al. |
| 9,364,216 B2 | | 6/2016 | Rockrohr et al. |
| 9,364,240 B2 | | 6/2016 | Whitfield et al. |
| 9,370,356 B2 | * | 6/2016 | Euteneuer ............ A61F 2/0811 |
| 9,486,218 B2 | | 11/2016 | Criscuolo et al. |
| 9,713,468 B2 | | 7/2017 | Harris et al. |
| 10,039,545 B2 | | 8/2018 | Sadowski et al. |
| 10,123,796 B2 | | 11/2018 | Westling et al. |
| 10,463,368 B2 | | 11/2019 | Kostrzewski |
| 10,470,761 B2 | | 11/2019 | Morgan et al. |
| 11,730,476 B2 | * | 8/2023 | Rodriguez-Navarro ..................... A61B 34/73 |
| | | | 606/142 |
| 2004/0097971 A1 | | 5/2004 | Hughett |
| 2007/0075115 A1 | | 4/2007 | Olson et al. |
| 2008/0078807 A1 | | 4/2008 | Hess et al. |
| 2009/0018553 A1 | | 1/2009 | McLean et al. |
| 2009/0112234 A1 | | 4/2009 | Crainich et al. |
| 2010/0057102 A1 | | 3/2010 | Sorrentino et al. |
| 2010/0057103 A1 | | 3/2010 | Sorrentino et al. |
| 2010/0198192 A1 | | 8/2010 | Serina et al. |
| 2010/0292713 A1 | | 11/2010 | Cohn et al. |
| 2010/0292715 A1 | | 11/2010 | Nering et al. |
| 2010/0312250 A1 | | 12/2010 | Euteneuer et al. |
| 2011/0079627 A1 | | 4/2011 | Cardinale et al. |
| 2012/0211543 A1 | | 8/2012 | Euteneuer |
| 2013/0178871 A1 | | 7/2013 | Koogle, Jr. et al. |
| 2013/0245627 A1 | * | 9/2013 | Euteneuer .............. A61B 17/56 |
| | | | 606/75 |
| 2013/0245682 A1 | | 9/2013 | Euteneuer et al. |
| 2016/0157703 A1 | * | 6/2016 | Brooks .............. A61B 17/1285 |
| | | | 600/104 |
| 2023/0116756 A1 | * | 4/2023 | Mata .................... A61B 17/068 |
| | | | 227/175.1 |

* cited by examiner

MEDICAL IMPLANT DELIVERY SYSTEM AND RELATED METHODS

CROSS REFERENCE TO RELATED APPLICATIONS

This application is a continuation of International Application No. PCT/US2021/038198, filed Jun. 21, 2021, titled MEDICAL IMPLANT DELIVERY SYSTEM AND RELATED METHODS, which claims the benefit of and priority to U.S. Provisional Patent Application Ser. No. 63/042,160, filed Jun. 22, 2020, titled REGENETEN NEXT-GEN MULTISHOT TENDON ANCHOR INSERTER HANDLE SET, U.S. Provisional Patent Application Ser. No. 63/042,174, filed Jun. 22, 2020, titled PRE-LOADED MULTI-SHOT STAPLER, U.S. Provisional Patent Application Ser. No. 63/042,197, filed Jun. 22, 2020, titled MULTI-SHOT PRE-LOADED ANCHOR DELIVERY INSTRUMENT, U.S. Provisional Patent Application Ser. No. 63/042,196, filed Jun. 22, 2020, titled MEDICAL IMPLANT DELIVERY SYSTEM AND RELATED METHODS, the disclosures of which are incorporated herein by reference.

TECHNICAL FIELD

The present disclosure pertains generally, but not by way of limitation, to orthopedic implants and methods of treatment. More particularly, the present disclosure relates to a tendon repair implant delivery system, such as one that is engineered for arthroscopic placement over or in the area of a full or partial thickness tear of a tendon, such as the supraspinatus tendon of the shoulder or other anatomical joint

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Current procedures for treatment of a torn tendon include affixing a biocompatible implant over the torn tendon. There is an ongoing need to deliver and adequately secure medical implants during an arthroscopic procedure in order to treat injuries to the rotator cuff, rotator cuff tendons, or other soft tissue or tendon injuries throughout a body.

BRIEF SUMMARY

This disclosure provides design, material, manufacturing method, and use alternatives for medical devices. An example implant delivery system includes a fixation member delivery system including an elongate shaft extending along a longitudinal axis, first and second rails extending parallel to the longitudinal axis, a plurality of fixation members arranged sequentially along the longitudinal axis with each fixation member slidably disposed on the first and second rails and an actuation assembly. The actuation assembly includes a first elongate member including a first plurality of engagement members disposed along the first elongate member with a distal end region of each engagement member of the first elongate member in engagement with one of the fixation members, a second elongate member including a second plurality of engagement members disposed along the second elongate member with a distal end region of each engagement member of the second elongate member in engagement with one of the fixation members. Additionally, cyclical actuation of the actuation assembly is configured to incrementally move the fixation members distally along the first and second rails to deploy each of the plurality of fixation members in sequence.

Alternatively or additionally to any of the embodiments above, wherein the cyclical actuation of the actuation assembly includes simultaneous distal advancement of the first longitudinal member and the second longitudinal member relative to the first rail and the second rail.

Alternatively or additionally to any of the embodiments above, wherein the cyclical actuation of the actuation assembly further includes proximal retraction of the second longitudinal member relative to the first longitudinal member, the first rail, the second rail, and one or more of the fixation members.

Alternatively or additionally to any of the embodiments above, wherein the first longitudinal member, the first rail, the second rail, and one or more of the fixation members are held stationary as the second longitudinal member is proximally retracted.

Alternatively or additionally to any of the embodiments above, wherein one or more of the second plurality of engagement members is configured to flex away from the longitudinal axis as the second longitudinal member is proximally retracted.

Alternatively or additionally to any of the embodiments above, wherein the distal end region of each of the first plurality of engagement members remains engaged to a corresponding fixation member as the second longitudinal member is proximally retracted.

Alternatively or additionally to any of the embodiments above, wherein the cyclical actuation of the actuation assembly further includes subsequent proximal retraction of the first longitudinal member after the proximal retraction of the second longitudinal member.

Alternatively or additionally to any of the embodiments above, wherein one or more of the first plurality of engagement members is configured to flex away from the longitudinal axis as the first longitudinal member is proximally retracted.

Alternatively or additionally to any of the embodiments above, wherein the distal end region of each of the second plurality of engagement members remains engaged to a corresponding fixation member as the first longitudinal member is proximally retracted.

Alternatively or additionally to any of the embodiments above, wherein the plurality of fixation members are aligned with one another in a single plane along the longitudinal axis.

Alternatively or additionally to any of the embodiments above, wherein each of the first plurality of engagement members are longitudinally aligned with one another and wherein each of the second plurality of engagement members are longitudinally aligned with one another.

Alternatively or additionally to any of the embodiments above, wherein the proximal end region of each of the plurality of fixation members includes a first profile, and wherein the distal end region of each of the first plurality of engagement members and the distal end region of each of the second plurality of engagement members includes a second profile, and wherein the first profile is configured to mate with the second profile.

Alternatively or additionally to any of the embodiments above, wherein each of the first rail and the second rail have a flared distal end region.

Alternatively or additionally to any of the embodiments above, wherein the flared distal end region of each of the first rail and the second rail includes a first width measured perpendicular to the longitudinal axis, and wherein each of the first aperture and the second aperture have a second width measured parallel to the first width, and wherein the first width of the flared distal end region is larger than the second width of the first and second apertures.

Alternatively or additionally to any of the embodiments above, wherein the first rail extends through the first aperture of each of the plurality of fixation members, and wherein the second rail extends through the second aperture of each of the plurality of fixation members.

Alternatively or additionally to any of the embodiments above, wherein each cycle of the cyclical actuation of the actuation assembly deploys a distalmost fixation member of the plurality of fixation members from a distal end of the elongate shaft.

Alternatively or additionally to any of the embodiments above, wherein the first and second elongate members extend parallel to and are positioned on opposing sides of the longitudinal axis and parallel therewith with a portion of each of the first plurality of engagement members extending inward toward the longitudinal axis and a portion of each of the second plurality of engagement members extending inward toward the longitudinal axis.

Alternatively or additionally to any of the embodiments above, wherein the first rail and the second rail are substantially parallel to one another.

Another example fixation member delivery system includes an outer shaft, the outer shaft including a lumen, a proximal end region, a distal end region and an opening positioned at a distal end thereof. The system also includes a handle coupled to the proximal end region of the outer shaft and an actuation assembly positioned within the lumen of the outer shaft and coupled to the handle. The actuation assembly includes first and second rails extending parallel to a longitudinal axis of the outer shaft, a plurality of fixation members arranged sequentially along the longitudinal axis with each fixation member slidably disposed on the first and second rails, a first elongate member including a first plurality of engagement members disposed along the first elongate member with a distal end region of each engagement member of the first elongate member in engagement with one of the fixation members, and a second elongate member including a second plurality of engagement members disposed along the second elongate member with a distal end region of each engagement member of the second elongate member in engagement with one of the fixation members. Additionally, cyclical actuation of the actuation assembly is configured to incrementally move the fixation members distally along the first and second rails to deploy each of the plurality of fixation members in sequence.

An example method of deploying a plurality of fasteners to a target site includes positioning a fastener delivery system adjacent a target site, the fastener delivery system including an actuation assembly. The actuation assembly includes an elongate shaft extending along a longitudinal axis, first and second rails extending parallel to the longitudinal axis, a plurality of fasteners arranged sequentially along the longitudinal axis with each fastener slidably disposed on the first and second rails, a first elongate member including a first plurality of engagement members disposed along the first elongate member with a distal end region of each engagement member of the first elongate member in engagement with one of the fasteners, a second elongate member including a second plurality of engagement members disposed along the second elongate member with a distal end region of each engagement member of the second elongate member in engagement with one of the fasteners. The method also includes cyclically actuating the actuation assembly to incrementally move the fasteners distally along the first and second rails and deploying each of the plurality of fasteners in sequence.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1A:
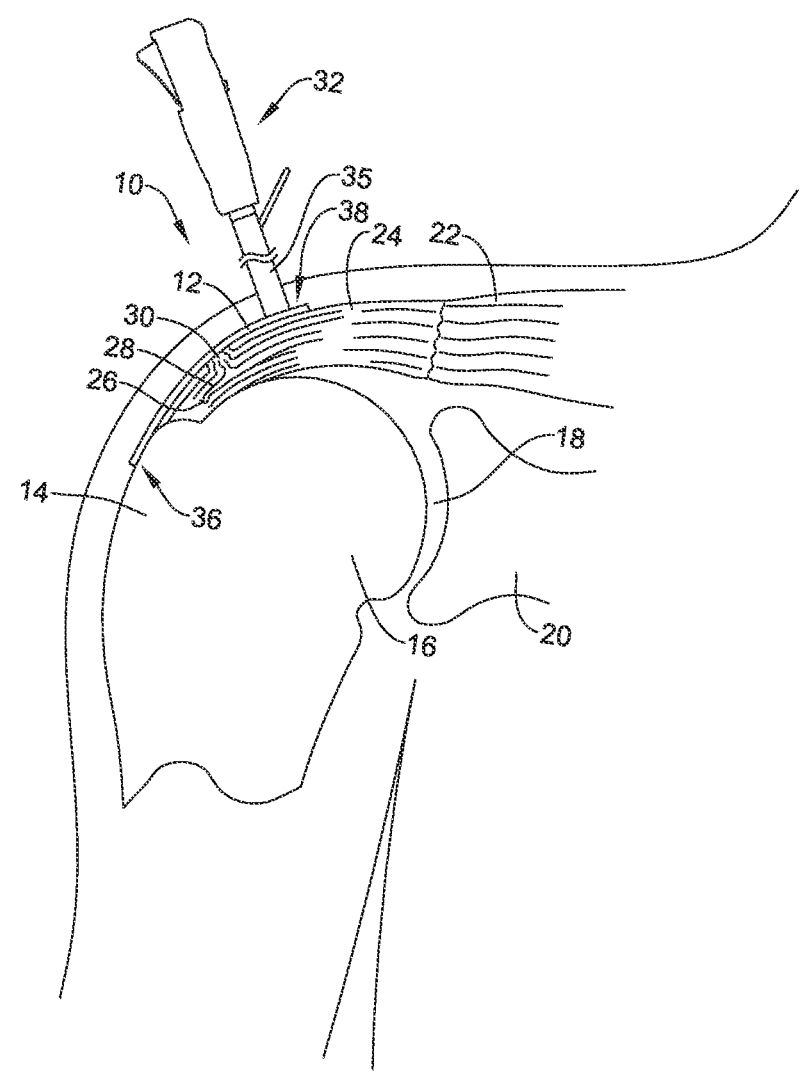
FIG. 1A illustrates an example implant delivery device positioned within a shoulder of a patient.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Current repair procedures may attempt to alleviate impingement or make room for movement of the tendon to prevent further damage and relieve discomfort. An accepted treatment for rotator cuff tears may include reattaching the torn tendon to the humeral head using sutures or anchors. Additionally, in treating rotator cuff tears, an accepted practice may also include the placement of a scaffold over the repaired tendon to mechanically reinforce the repaired tendon or promote tissue growth for natural repair. The scaffold may be secured to the tendon using one or more, or a plurality of fixation members, such as staples or other anchors. Therefore, there is an ongoing need to deliver and adequately secure medical implants during an arthroscopic procedure in order to treat injuries to the rotator cuff, rotator cuff tendons, or other soft tissue or tendon injuries throughout a body.

FIG. 1A shows a cross-sectional view of a shoulder 10 including an example implant 12. The shoulder 10 further shows a head 14 of the humerus 16 mating with a glenoid fossa 18 of the scapula 20. The glenoid fossa 18 includes a shallow depression in the scapula 20. A supraspinatus tendon 22 is also shown. These muscles (along with others) control the movement of the humerus 16 relative to the scapula 20. A distal tendon 24 of the supraspinatus tendon 22 meets the humerus 16 at an insertion point 26.

In FIG. 1A, the tendon 24 includes a damaged portion 28 located near the insertion point 26. The damaged portion 28 includes a tear 30 extending partially through the tendon 24. The tear 30 may be referred to as a partial thickness tear. The depicted partial thickness tear 30 is on the bursal side of the tendon, however, the tear may also be on the opposite or articular side of the tendon 24 and/or may include internal tears to the tendon 24 not visible on either surface.

FIG. 1A further illustrates that the tendon repair implant 12 has been placed over the partial thickness tear 30. In this example, the tendon repair implant 12 is placed on the bursal side of the tendon regardless of whether the tear is on the bursal side, articular side or within the tendon. Further, the tendon repair implant 12 may overlay multiple tears.

In some instances, delivery of an implant 12 (e.g., a sheet-like implant) to a target site of a patient may require a physician to create an incision in the patient sufficient to access the target implant site. After creating this "access site," the physician may insert an implant delivery system through the access site and position the distal end of the implant delivery system adjacent the target implant site. The physician may then manipulate the implant delivery system to deploy an implant out of a delivery sheath (not shown in FIG. 1A) adjacent the target implant site.

When positioning the implant 12 adjacent a target site, a clinician may orient the implant 12 such that the proximal portion 36 may be adjacent (e.g., overlaid) on a portion of the humerus 16 (e.g., on the bone), while the distal portion 38 of the implant 12 may overlay the tendon 24. Further, once the implant 12 has been placed appropriately, it may be desirable to utilize a stapling instrument 32 to insert staples 34 (not shown in FIG. 1A, but shown in FIG. 2) through the implant 12 into the tendon tissue 24 and/or the bone 16.

FIG. 1A further illustrates that, in some examples, the stapling instrument 32 may include a removeable outer access sheath 35 designed to provide an atraumatic entry profile during the advancement of the stapling instrument 32 to the implant site. As will be described in greater detail below, the outer access sheath 35 may cover the distal end region of the stapling instrument 32, thereby shielding portions of the patient's shoulder from sharp portions of the stapling instrument 32 as the stapling instrument 32 is inserted through the skin (e.g., the access site) and positioned adjacent the implant 12.

Figure 1B:
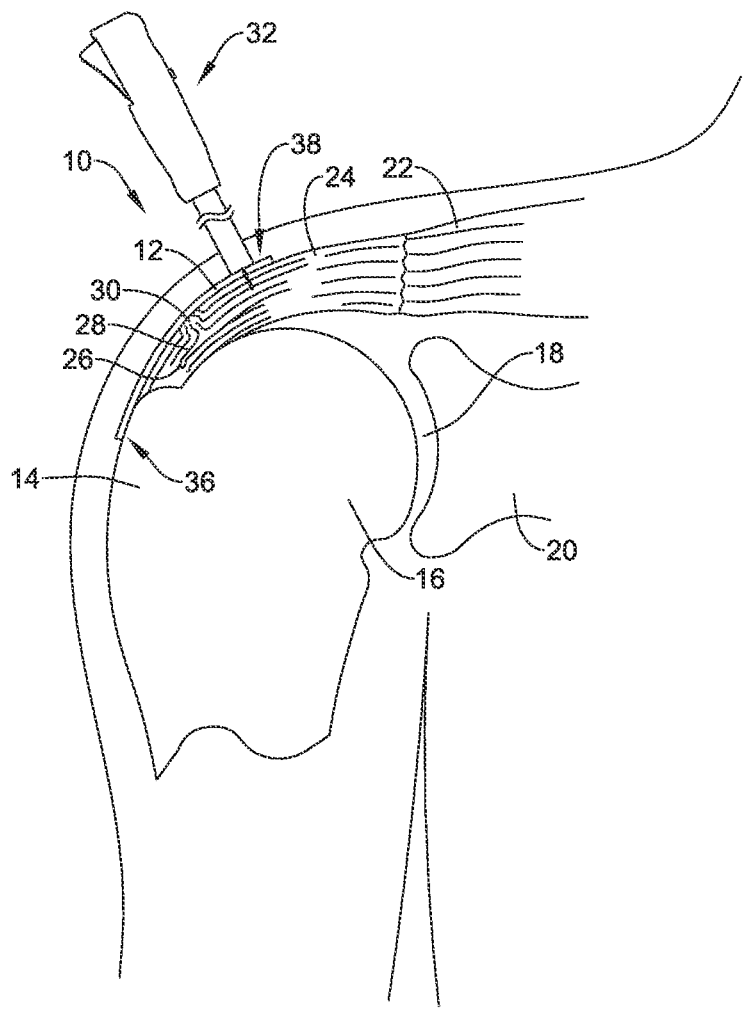
FIG. 1B illustrates the example implant delivery device shown in FIG. 1 with an outer delivery sheath having been removed.

FIG. 1B illustrates the stapling instrument 32 positioned adjacent to the implant 12. Additionally, FIG. 1B illustrates that the outer access sheath 35 (shown in FIG. 1A) has been removed from the stapling instrument 32. Once the stapling instrument 32, and outer access sheath 35 coupled thereto, has been inserted through the incision and directed to the surgical site, the outer access sheath 35 may be decoupled and removed from the stapling instrument 32. As described herein, removing the outer access sheath 35 from the stapling instrument 32 may expose portions of the stapling instrument 32 which may be utilized to affix the implant 12 to the humerus 16 and/or tendon 24. For example, the implant 12 may be anchored to the humeral head using one or more bone anchors (e.g., staples) and the implant 12 may be anchored to the tendon 24 using a plurality of tendon anchors (e.g., staples) arranged around the periphery of the implant 12.

Figure 2:
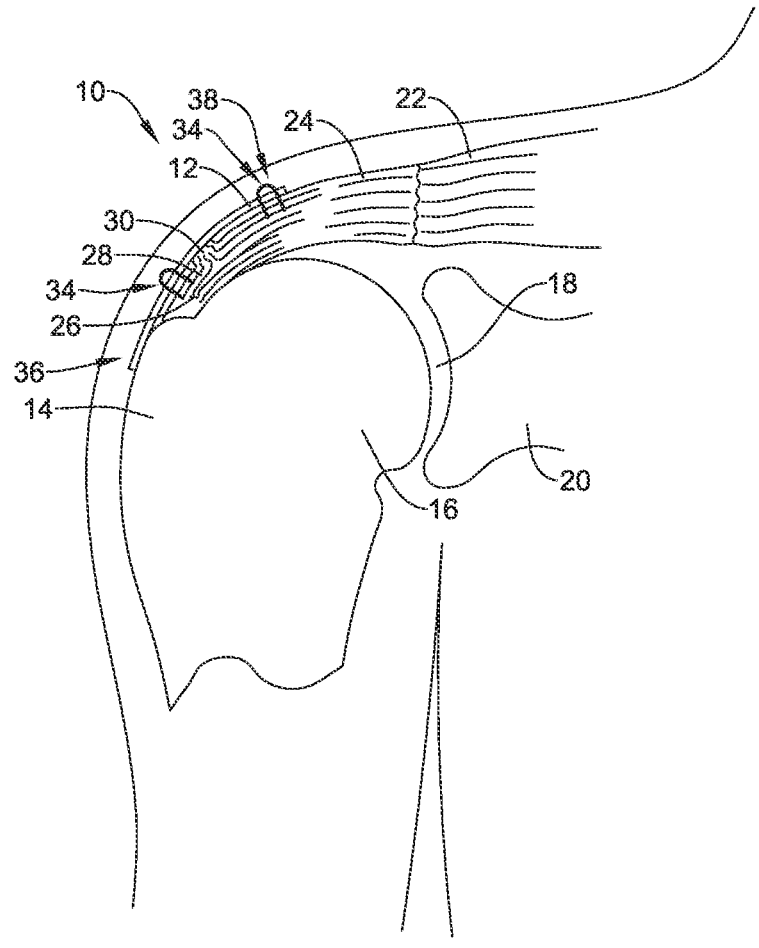
FIG. 2 illustrates a shoulder including a head of the humerus mating with the glenoid fossa of the scapula at a glenohumeral joint and an implant affixed to a tendon.

FIG. 2 illustrates the cross-section of the shoulder 10 shown in FIGS. 1A-1B, whereby the implant 12 may be positioned such that the proximal portion 36 may be adjacent (e.g., overlaid) on a portion of the humerus 16 (e.g., on the bone), while the distal portion 38 of the implant 12 may overlay the tendon 24. Further, FIG. 2 illustrates the cross-section of the shoulder 10 after a clinician has utilized an implant stapler 32 (not shown in FIG. 2, but shown in FIGS. 1A-1B) to insert two example fixation members 34 (e.g., staples, anchors, etc.) along the proximal portion 36 and the distal portion 38 of the implant 12. The fixation members 34 may be used to fixedly secure the implant 12 to the tendon 24. Additional fixation members, such as bone staples, may be used to fixedly secure the implant 12 to the humerus 16.

Figure 3A:
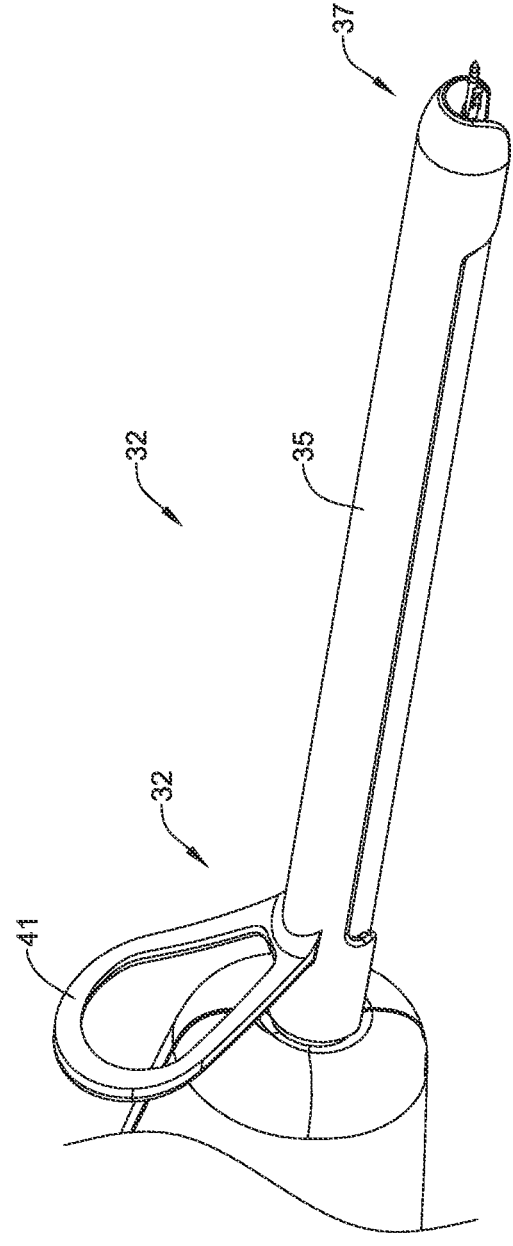
FIG. 3A illustrates an outer delivery sheath attached to an example implant delivery device.

FIG. 3A illustrates a portion of an example stapling instrument 32. In particular, FIG. 3C illustrates the outer delivery sheath 35 described above with respect to FIG. 1A assembled onto the elongate shaft of the stapling instrument 32. It can be appreciated that the outer delivery sheath 35 may include a distal end region 37 and a proximal end region 39. As illustrated in FIG. 3A, the distal end region 37 may include a tapered tip portion. The tapered tip portion may extend distally beyond the distal extent of the elongate shaft of the stapling instrument 32, such as distally beyond the tines 40 (described below). The tapered tip portion may provide the stapling instrument 32 with an atraumatic entry profile. In other words, the tapered tip portion of the distal end region 37 of the outer delivery sheath 35 may provide a tapered tissue entry profile (e.g., a gradual entry profile) which may limit trauma to the skin (or other tissue) as the distal end region of the outer delivery sheath 35 is inserted into a patient.

As discussed herein, after being inserted through an access site of the patient, the outer access sheath 35 may be removed from both the stapling instrument 32 and the patient. For example, FIG. 3B illustrates the outer access sheath 35 after being removed from the outer shaft 42 of the stapling instrument 32.

Figure 3B:
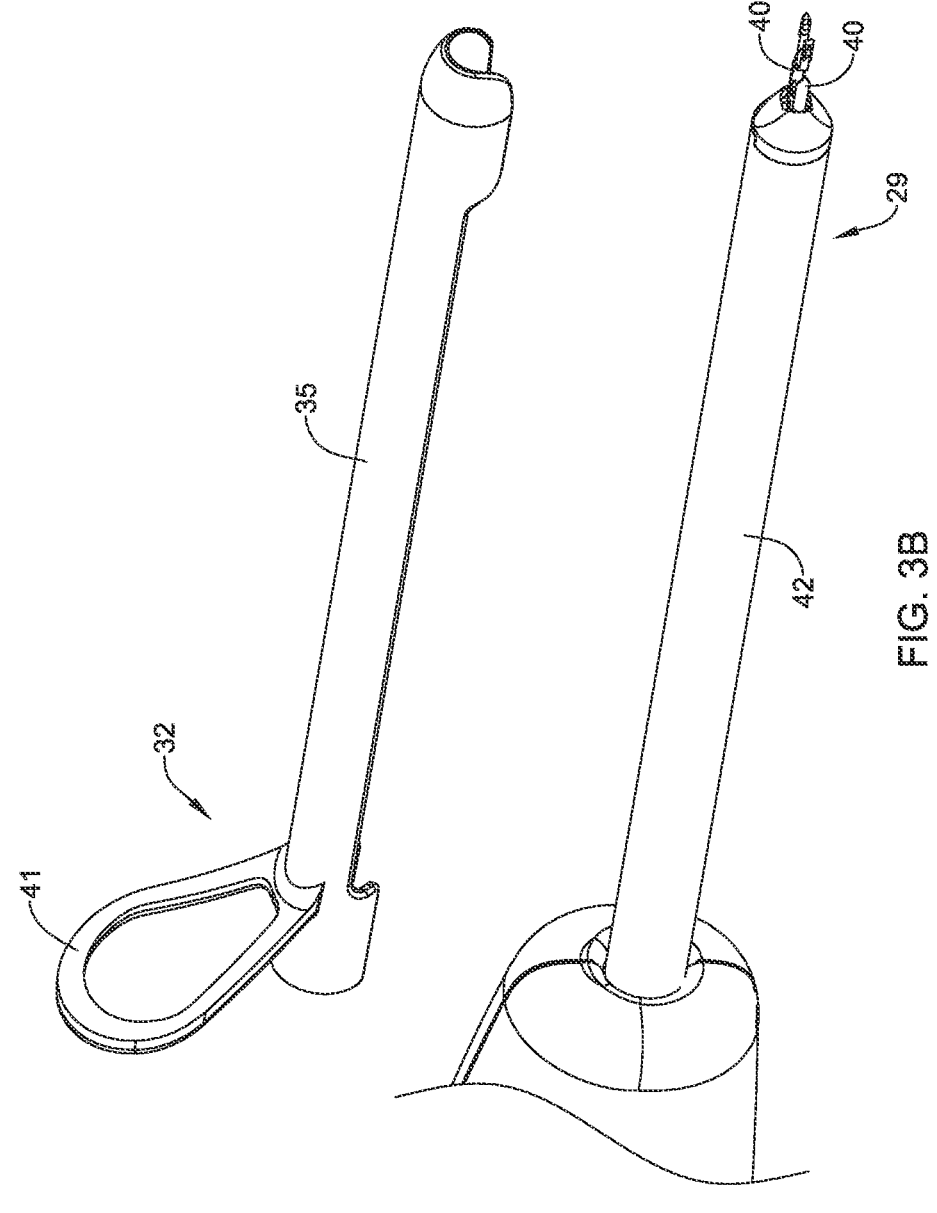
FIG. 3B illustrates the outer delivery sheath shown in FIG. 3A removed from the example implant delivery device.
Figure 3C:
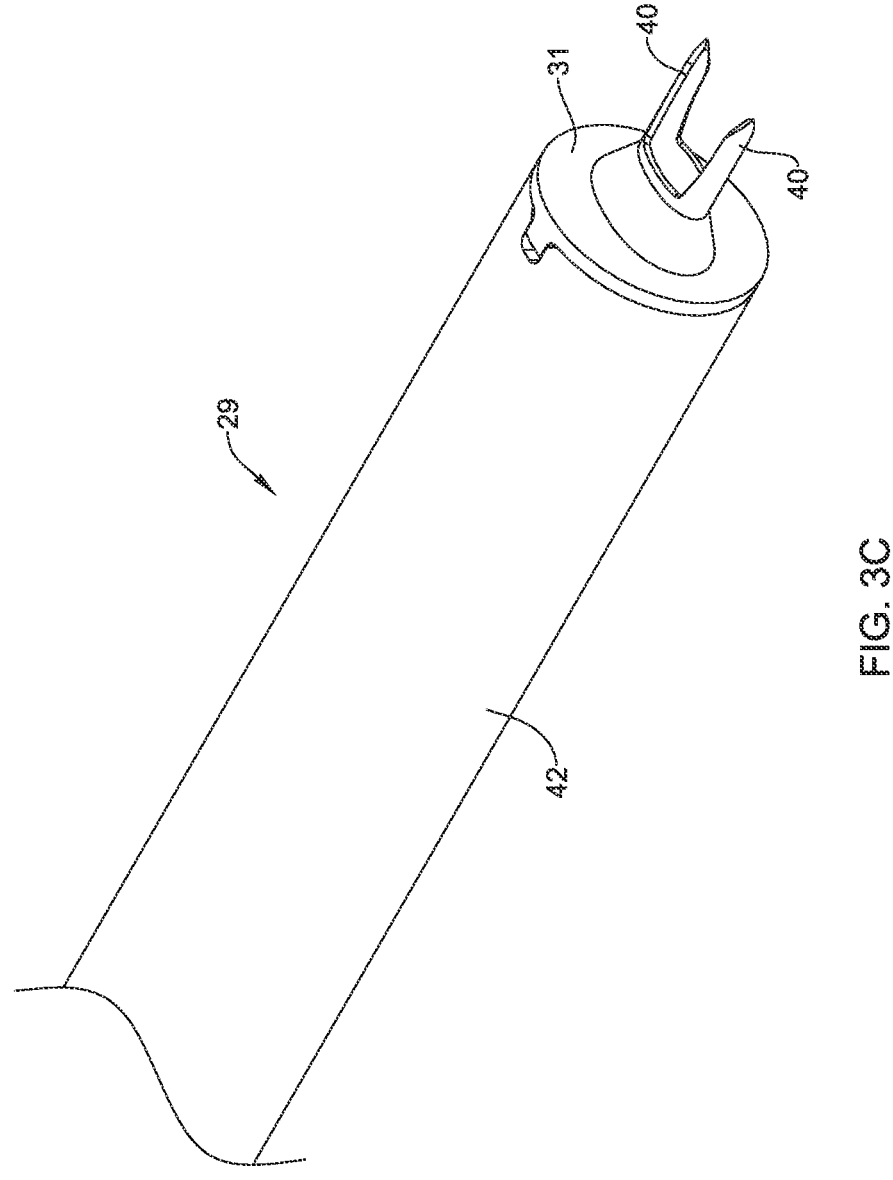
FIG. 3C illustrates another portion of an example implant delivery device.

FIG. 3B further illustrates that the proximal end region of the access sheath 35 may include a finger loop 41 or other structure to grasp in order to separate the access sheath 35 from the outer shaft 42 of the stapling instrument 32. The finger loop 41 may be utilized to grip and remove the outer access sheath 35 from the outer shaft 42. For example, after being inserted through an access site of the patient and positioned adjacent to the implant site, a physician may grip the outer access sheath 35 via the finger loop 41 and subsequently remove the outer access sheath 35 from the outer shaft 42 via pulling on the finger loop 41 (which imparts a removal force sufficient to release the outer access sheath 35 from the outer shaft 42).

It can be appreciated from FIG. 3B that the outer access sheath 35 may be designed to be press-fit (e.g., snap fit) along a portion of the outer shaft 42 of the stapling instrument 32. In some instances, a portion of the outer access sheath 35 may not extend completely around the outer surface of the outer shaft 42. For example, one or more portions of the outer access sheath 35 may include a cross-sectional shape which is substantially semi-circular and designed to mate with the contour of the outer surface of the outer shaft 42. For example, the access sheath 35 may include a longitudinal slot extending the entire length of the access sheath 35 from the distal end of the access sheath 35 to the proximal end of the access sheath 35. Thus, the access sheath 35 may be coupled to the outer shaft 42 by laterally inserting the outer shaft 42 through the longitudinal slot and/or the access sheath 35 may be removed or decoupled from the outer shaft 42 by laterally withdrawing the outer shaft 42 through the longitudinal slot. Accordingly, the outer access sheath 35 may be designed to be press fit onto the outer surface of the outer shaft 42. It can be further appreciated that the access sheath 35 may be designed such that the force required to remove the outer access sheath 35 from the outer shaft 42 may be large enough to prevent the outer access sheath 35 from coming off the outer shaft 42 while being inserted through a tissue access site, while also being low enough that it can be removed from the outer shaft 42 after insertion into the patient.

In some instances, the access sheath 35 may include a proximal portion that wraps or extends around greater than 180°, but less than 360°, of the circumference of the outer shaft 42 and a distal portion that also wraps or extends around greater than 180°, but less than 360°, of the circumference of the outer shaft 42. The access sheath 35 may include a medial portion extending between the proximal portion and the distal portion, where the medial portion wraps around the circumference of the outer shaft 42 less than the proximal portion and the distal portion. For example, the medial portion may wrap or extend around the outer shaft 42 for 180° or less than 180° of the circumference of the outer shaft 42. Thus, the longitudinal slot along the medial portion may be wider than the longitudinal slot through the proximal and distal portions of the access sheath 35. Thus, to laterally remove the access sheath 35 from the outer shaft 42, the user may pull on the loop 41 to laterally remove the outer shaft 42 from the proximal portion of the access sheath 35 while the distal portion of the access sheath 35 remains wrapped around the outer shaft 42. The access sheath 35 may then be withdrawn proximally such that the distal portion of the access sheath 35 slides along the outer shaft 42 proximally until the distal portion of the access sheath 35 has passed through the incision to the exterior of the patient. Once exterior of the patient, the user may again apply a lateral force to decouple the access sheath 35 from the outer shaft 42 by passing the outer shaft 42 out through the longitudinal slot along the distal portion of the access sheath 35.

As described herein, FIG. 3B further illustrates that the distal end region 37 of the access sheath 35 may partially cover (or in some examples, completely cover) one or more tines 40 which extend distally from the distal end of the outer shaft 42. Further, the one or more tines 40 may include a sharp, pointed tip portion which may be utilized to create a pilot hole at the target tissue site. However, as discussed above, it may be undesirable for the tines 40 to engage with tissue other than at the implant site. Therefore, the distal end region 37 of the outer access sheath 35 may house (e.g., nest, cover, etc.) the one or more tines 40 within the distal end region 37 of the outer access sheath while passing the stapling instrument 32 through the access site to the implant securement site. Housing the one or more tines 40 within the distal end region 37 of the outer access sheath 35 may shield the one or more tines 40 from tissue as the stapling instrument 32 is advanced to the implant securement site.

FIG. 3C illustrates another portion of the example stapling instrument 32. In particular, FIG. 3C illustrates a shaft assembly 29 of a stapling instrument 32 (shown in FIG. 18). As will be discussed in greater detail below, the shaft assembly 29 may include a portion of the implant stapler 32 which extends distally away from a handle. Additionally, as described above, FIG. 3C illustrates that the shaft assembly 29 may include an elongate outer shaft 42, which may be an elongate tubular member. The outer shaft 42 may include an outer surface and a lumen extending therein. Additionally, the distal end region of the outer shaft 42 may include a distal face 31. The distal face 31 may include a surface of the outer shaft 42 which is substantially perpendicular to the longitudinal axis of the outer shaft 42.

As described above, FIG. 3C illustrates that the shaft assembly 29 may include a pair of tines 40 extending distally from the distal face 31. Collectively, the pair of tines 40 may define a passage through which a fixation member (not shown in FIG. 3C) may pass through as the fixation member is deployed out of the outer shaft 42 between the tines 40. Further, the tines 40 may be designed such that they create a pilot hole within the target site tissue. For example, after a clinician aligns the distal end of the shaft assembly 29 along the implant 12, the clinician may apply a force to the outer shaft 42 such that the tines 40 pierce through the implant 12 and into the target site (e.g., tendon tissue), thereby creating a pilot hole for which a fixation member (e.g., staple) may be inserted.

FIG. 3C illustrates that the tines 40 may include curved sides (e.g., concave surfaces facing the opposed tine 40 of the pair of tines) and a pointed end. In some examples, the curved sides of tines 40 may be configured to mate with curved sides of a variety of example fixation members. In different examples, the tines 40 may take various shapes, such as spikes, spears, prongs, or other shapes. Whatever shape the tines 40 may take, they may generally have pointed distal ends for piercing tissue or bone.

Figure 4:
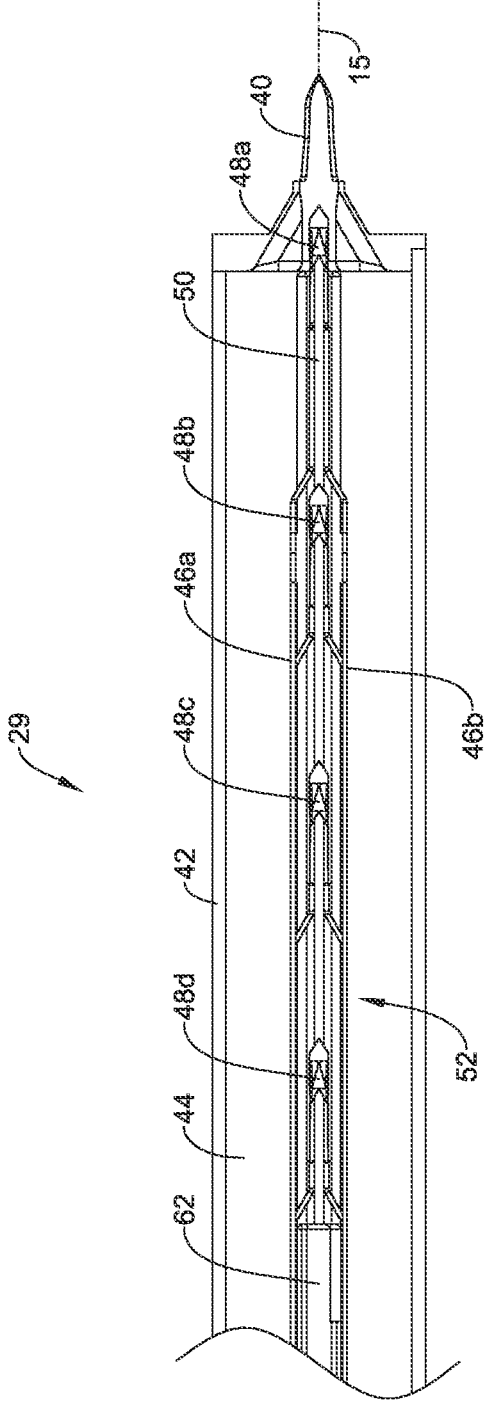
FIG. 4 illustrates another portion of an example implant delivery device.

FIG. 4 illustrates a cross-section of the shaft assembly 29 shown in FIG. 3C. FIG. 4 illustrates that the shaft assembly 29 may include a fixation member actuation assembly 52 positioned within the lumen 44 of the shaft 42. The fixation member actuation assembly 52 may include several components, which collectively, work together to deploy fixation members (e.g., staples) out the distal end of the shaft assembly 29.

FIG. 4 illustrates that the fixation member actuation assembly 52 may include a first longitudinal member 46a, such as a first longitudinal beam, and a second longitudinal member 46b, such as a second longitudinal beam. In some examples, the first longitudinal member 46a and the second longitudinal member 46b may be referred to as a first beam 46a and a second beam 46b, respectively. The first longitudinal member 46a and the second longitudinal member 46b may extend through the lumen 44 of the outer shaft 42 and attach to components of a handle (not shown in FIG. 4).

Figure 5:
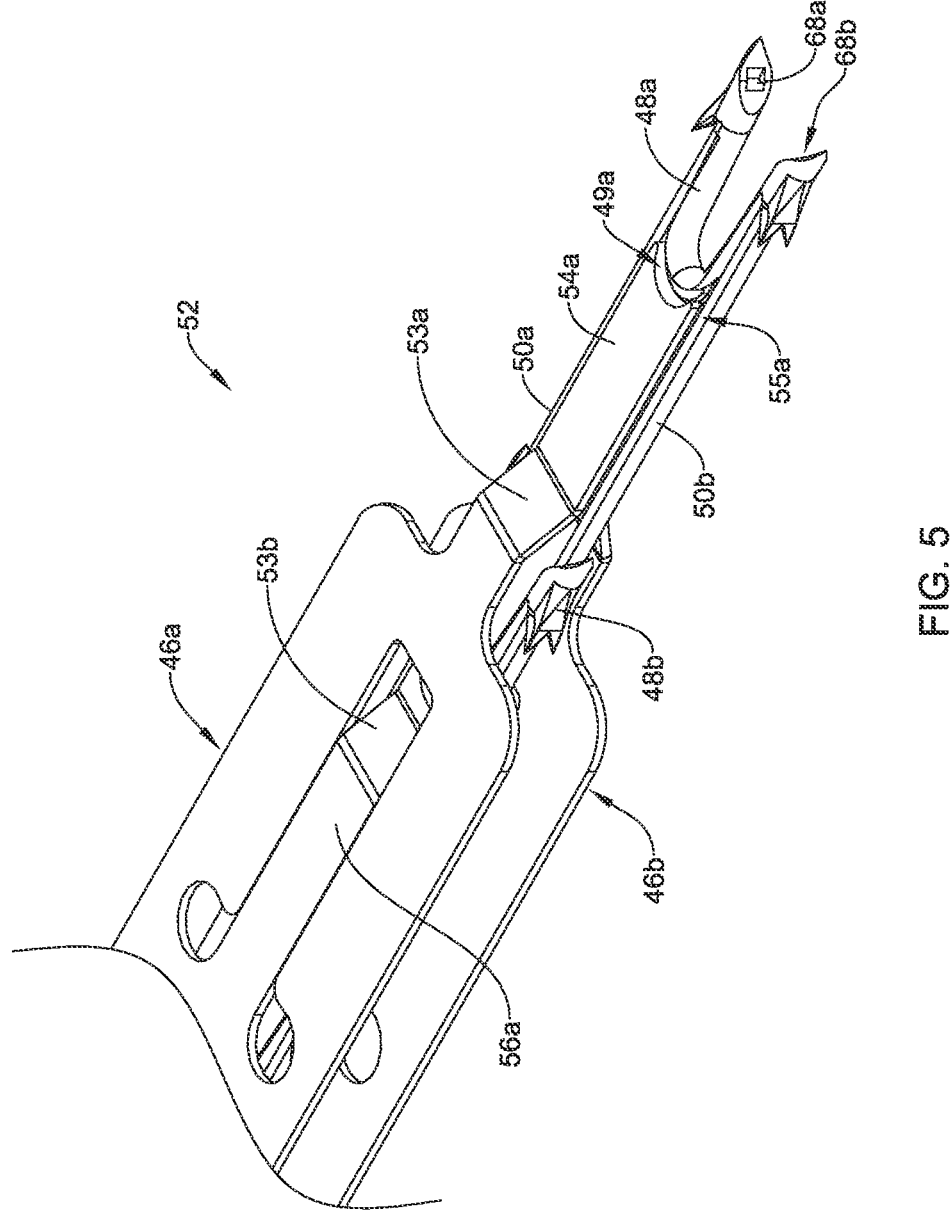
FIG. 5 illustrates another portion of an example implant delivery device.

Additionally, FIG. 4 illustrates that the shaft assembly 29 may further include one or more "rails" which may be attached to an actuation shaft 62 and extend distally therefrom. The rails may extend parallel to a longitudinal axis of the actuation shaft 62. The rails may be fixed relative to the actuation shaft 62 such that the rails move longitudinally with the actuation shaft 62 (i.e., the rails may move in unison with the actuation shaft 62). The rails may include a first rail 50a and a second rail 50b. The second rail 50b is shown in FIG. 4. It can be appreciated that the first rail 50a is obscured by the second rail 50b in FIG. 4. The first rail 50a is shown in FIGS. 5-7. It can further be appreciated that the first rail 50a and the second rail 50b are generally longitudinal members which extend from the actuation shaft 62 distally through the lumen 44 of the outer shaft 42. As will be discussed in greater detail below, the first rail 50a and the second rail 50b generally extend substantially parallel to one another through the lumen 44 of the outer shaft 42, and thus may extend parallel to the central longitudinal axis of the outer shaft 42. The first and second rails 50a/50b and the actuation shaft 62 may be positioned between the first longitudinal member 46a and the second longitudinal member 46b.

FIG. 4 further illustrates that one of more fixation members 48a/48b/48c/48d (e.g., staples) may be threaded onto the first rail 50b and the second rail 50a. For example, the fixation members 48a/48b/48c/48d may be staples having a first anchor portion having a pointed distal tip, a second anchor portion having a pointed distal tip, and a bridge extending between the proximal portions of the first and second anchor portions. Thus, the first rail 50a may extend through a passage of the first anchor portion of each staple and the second rail 50b may extend through a passage of the second anchor portion of each staple. The staples may be oriented in longitudinal alignment with the longitudinal axis of the outer shaft 42 with the distal points of the staples pointed toward the distal end of the outer shaft 42. As shown in FIG. 4, the fixation members 48a/48b/48c/48d may be spaced away from one another along the longitudinal axis 15 of the outer shaft 42 such that adjacent fixation members 48a/48b/48c/48d do not directly contact one another. It can be appreciated from FIG. 4 that the fixation members 48a/48b/48c/48d may be spaced apart from one another while threaded onto the first rail 50a and the second rail 50b. As such, the stapling instrument 32 may be initially loaded with a plurality of fixation members, such as four more staples, six or more staples, or eight or more staples for sequential deployment from the stapling instrument 32. As will be discussed in greater detail below, the fixation members 48a/48b/48c/48d may be sequentially advanced out of the distal end (e.g., through the tines 40) of the outer shaft 42 as the fixation member actuation assembly 52 is manipulated via a handle (the handle is not shown in FIG. 4).

FIG. 5 illustrates a portion of the fixation member actuation assembly 52. In particular, FIG. 5 illustrates that the distal end region of the fixation member actuation assembly 52 including the first longitudinal member 46a and the second longitudinal member 46*b*. It can be appreciated from FIG. 5 that the first longitudinal member 46*a* and the second longitudinal member 46*b* may extend generally parallel to one another while being laterally spaced from each other another. The fixation members 48*a*/48*b*/48*c*/48*d* and first and second rails 50*a*/50*b* may be positioned between the first and second longitudinal members 46*a*/46*b*.

FIG. 5 further illustrates the first fixation member 48*a* threaded onto the first rail 50*a* and the second rail 50*b* (the second fixation member 48*b* is also shown threaded on to the first rail 50*a* and the second rail 50*b*, however, it is partially obscured by the first longitudinal member 46*a* and the second longitudinal member 46*b*). FIG. 5 illustrates that, in some examples, the fixation members 48*a*/48*b*/48*c*/48*d* may include a first aperture 68*a* extending through a first anchor portion of a fixation member and a second aperture 68*b* extending through a second anchor portion of a fixation member through which the first rail 50*a* and the second rail 50*b* may extend, respectively. FIG. 5 further shows that the second fixation member 48*b* may be spaced away from the first fixation member 48*a* along the longitudinal axis (as discussed with respect to FIG. 4). It can be appreciated that the first aperture 68*a* and the second aperture 68 may be sized such that they permit the first fixation member 48*a* and the second fixation member 48*b* to slide along the first rail 50*a* and the second rail 50*b*.

The fixation member actuation assembly 52 is designed to cyclically advance the fixation members 48*a*/48*b*/48*c*/48*d* distally along the first rail 50*a* and the second rail 50*b* such that the fixation members 48*a*/48*b*/48*c*/48*d* may be sequentially deployed out of the distal end of the outer shaft 42 (through the aperture defined by the tines 40, as described above). FIG. 5 illustrates that the first longitudinal member 46*a* and the second longitudinal member 46*b* may include one or more features that facilitate the advancement of the fixation members 48*a*/48*b*/48*c*/48*d* along the first rail 50*a* and the second rail 50*b*. For example, FIG. 5 illustrates that the first longitudinal member 46*a* may include engagement portions 54*a*/56*a* (e.g., engagement tabs) which may be designed to engage a proximal end region of the first fixation member 48*a* and the second fixation member 48*b*, respectively. In particular, FIG. 5 illustrates that the first longitudinal member 46*a* may include an engagement portion 54*a* (e.g., an engagement tab) which includes a distal end region 55*a* designed to engage a proximal end 49*a* (e.g. bridge) of the fixation member 48*a*. As shown in FIG. 5, the engagement portion 54*a* may include an angled portion 53*a* which transitions the engagement portion 54*a* from a position in which the engagement portion 54*a* lies within a first plane of the first longitudinal member 46*a* to a second plane in which the engagement portion 54*a* lies within the plane of the fixation member 48*a*. Likewise, as further illustrated in FIG. 6, the second longitudinal member 46*b* may include an engagement portion 54*b* (e.g., an engagement tab) which includes a distal end region 55*b* designed to engage a proximal end 49*a* (e.g. bridge) of the fixation member 48*a*. The angled portions 53*a*/53*b* permit the first longitudinal member 46*a* and the second longitudinal member 46*b* to remain spaced apart from one another while also allowing the first engagement member 54*a* and the second engagement member 56*a* to engage the proximal end regions of the fixation member 48*a* and the fixation member 48*b*, respectively.

Further, as discussed above, the distal end region 55*a* of the engagement portion 54*a* may include a profile which is designed to mate with the profile of the proximal end region 49*a* of the fixation member 48*a*. For example, the distal end region 55*a* of the engagement portion 54*a* may include a curved profile which mates with a curved profile of the proximal end region 49*a* of the fixation member 48*a*. The matching profiles of the distal end region 55*a* of the engagement portion 54*a* and the proximal end region 49*a* of the fixation member 48*a* may allow the engagement portion 54*a* to transfer a maximum force to the fixation member 48*a* when deploying the fixation member 48*a* out of the distal end of the outer shaft 42.

Figure 6A:
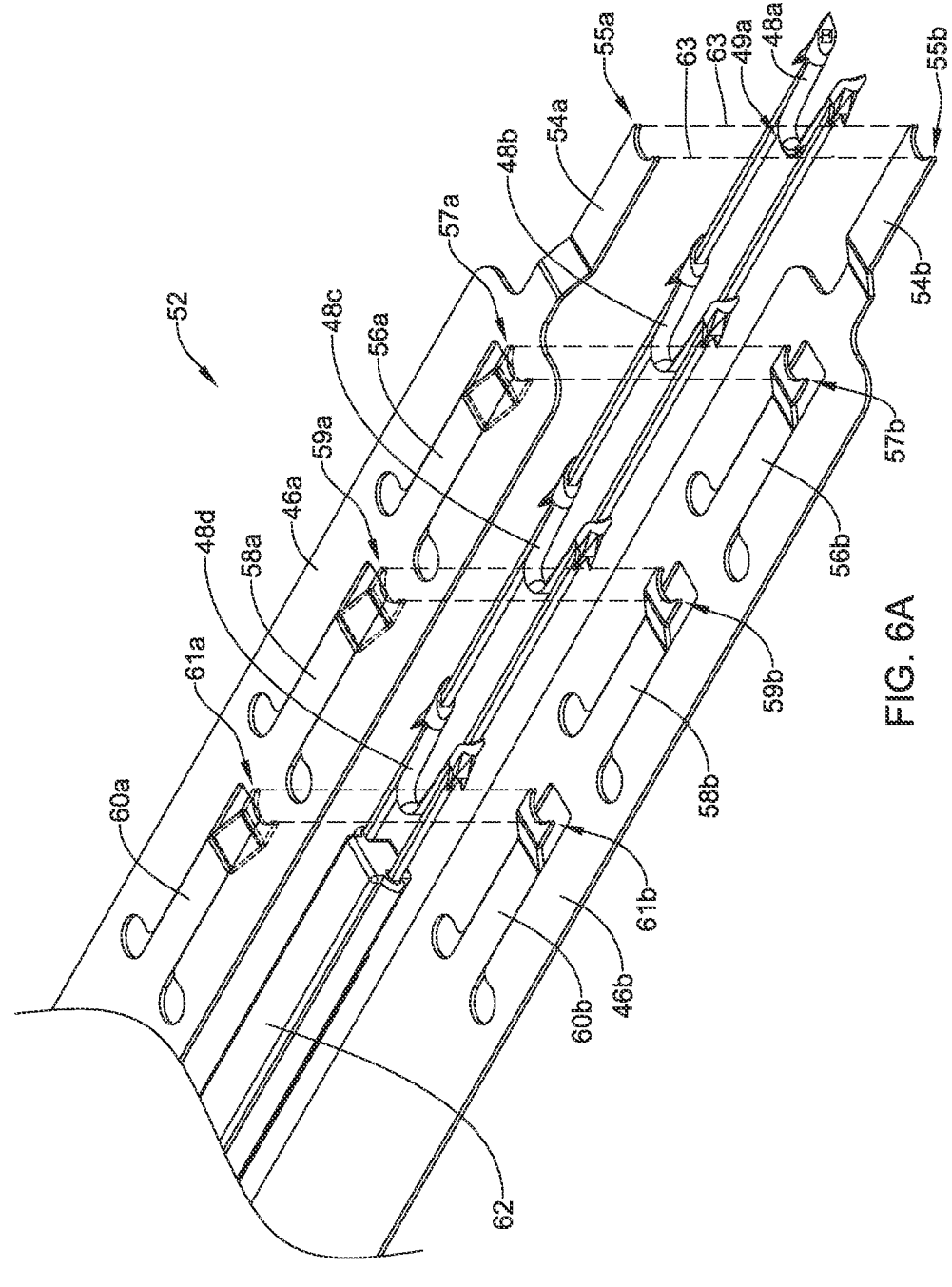
FIG. 6A illustrates another portion of an example implant delivery device.
Figure 7:
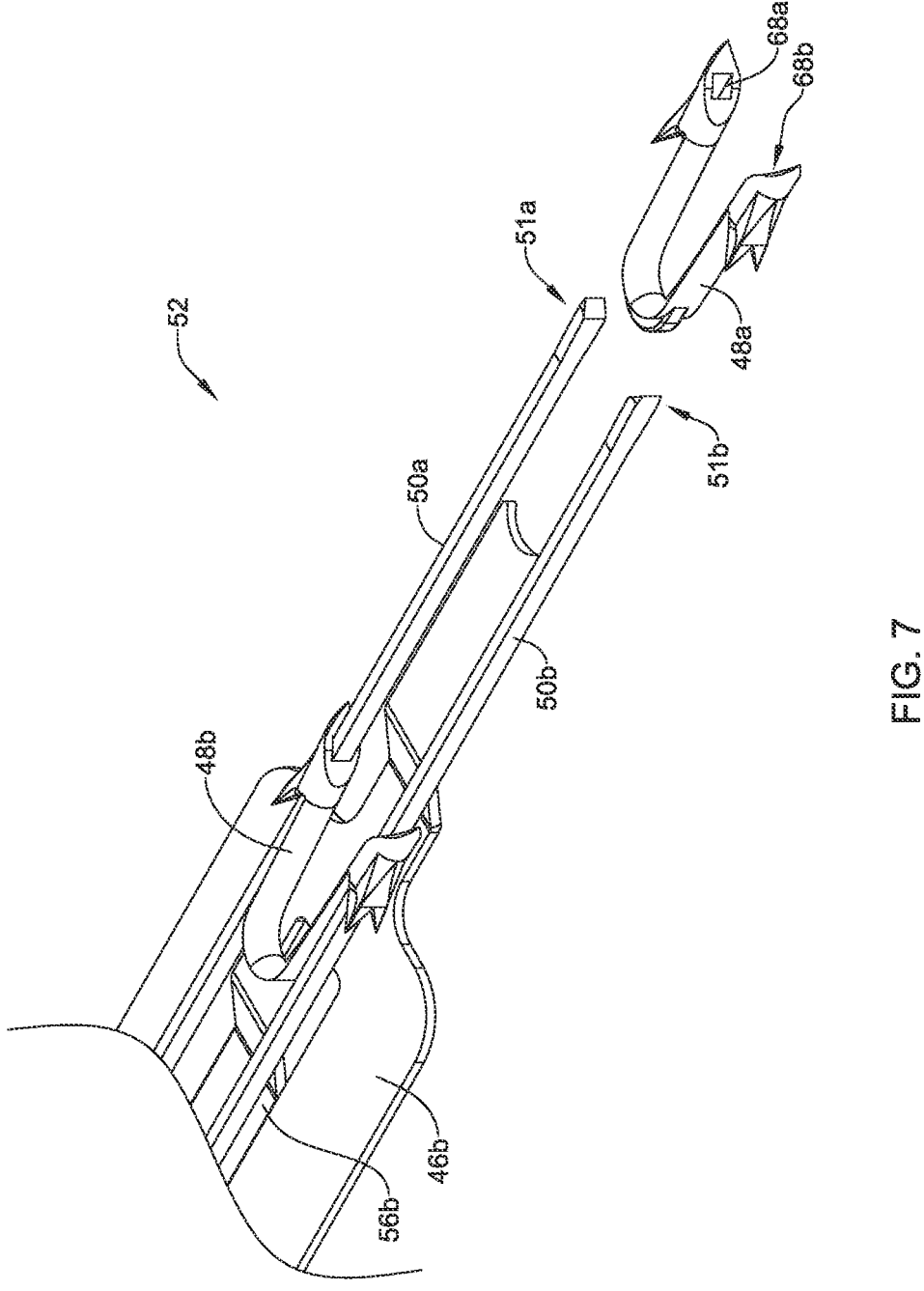
FIG. 7 illustrates another portion of an example implant delivery device.

FIG. 6A illustrates an exploded view of the fixation member actuation assembly 52. In particular, FIG. 6A illustrates the first longitudinal member 46*a* having engagement portions 54*a*/56*a*/58*a*/60*a*, each of which are disposed and aligned along the first longitudinal member 46*a*. The first longitudinal member 46*a* may have an engagement portion for each fixation member initially loaded into the stapling instrument 32. Similarly, FIG. 6A illustrates the second longitudinal member 46*b* having engagement portions 54*b*/56*b*/58*b*/60*b*, each of which are disposed and aligned along the second longitudinal member 46*b*. The second longitudinal member 46*b* may have an engagement portion for each fixation member initially loaded into the stapling instrument 32. FIG. 6A further illustrates the fixation members 48*a*/48*b*/48*c*/48*d* threaded onto the first rail 50*a* and the second rail 50*b*. As described above, the fixation members 48*a*/48*b*/48*c*/48*d* may be axially spaced apart from one another with each fixation member engaged with one of the engagement portions of each of the first and second longitudinal members 46*a*/46*b*. Further, each of the first rail 50*a* and the second rail 50*b* may be coupled to the actuation shaft 62.

FIG. 6A further illustrates the general alignment of the engagement portions 54*a*/56*a*/58*a*/60*a* of the first longitudinal member 46*a* and the engagement portions 54*b*/56*b*/58*b*/60*b* of the second longitudinal member 46*b* with each of the fixation members 48*a*/48*b*/48*c*/48*d*, respectively. For example, the vertical dashed lines 63 illustrate the vertical alignment of the distal end 55*a* of the engagement portion 54*a* and the distal end 55*b* of the engagement portion 54*b* with the proximal end 49*a* of the fixation member 48*a* at the same longitudinal position of the stapling instrument 32. It can be appreciated from FIG. 6A that the distal end of each of the other engagement portions 56*a*/58*a*/60*a* and the engagement portions 56*b*/58*b*/60*b* are similarly aligned with each corresponding fixation member 48*b*/48*c*/48*d* (as illustrated by the additional vertical dashed lines shown in FIG. 6A). In other words, when assembled, the engagement portions 54*a*/56*a*/58*a*/60*a* of the first longitudinal member 46*a* and the engagement portions 54*b*/56*b*/58*b*/60*b* of the second longitudinal member 46*b* may be engaged with each of the fixation members 48*a*/48*b*/48*c*/48*d* such that proximal-to-distal advancement of the first longitudinal member 46*a* and the second longitudinal member 46*b* may push each of the fixation members 48*a*/48*b*/48*c*/48*d* along the first rail 50*a* and the second rail 50*b*.

Figure 6B:
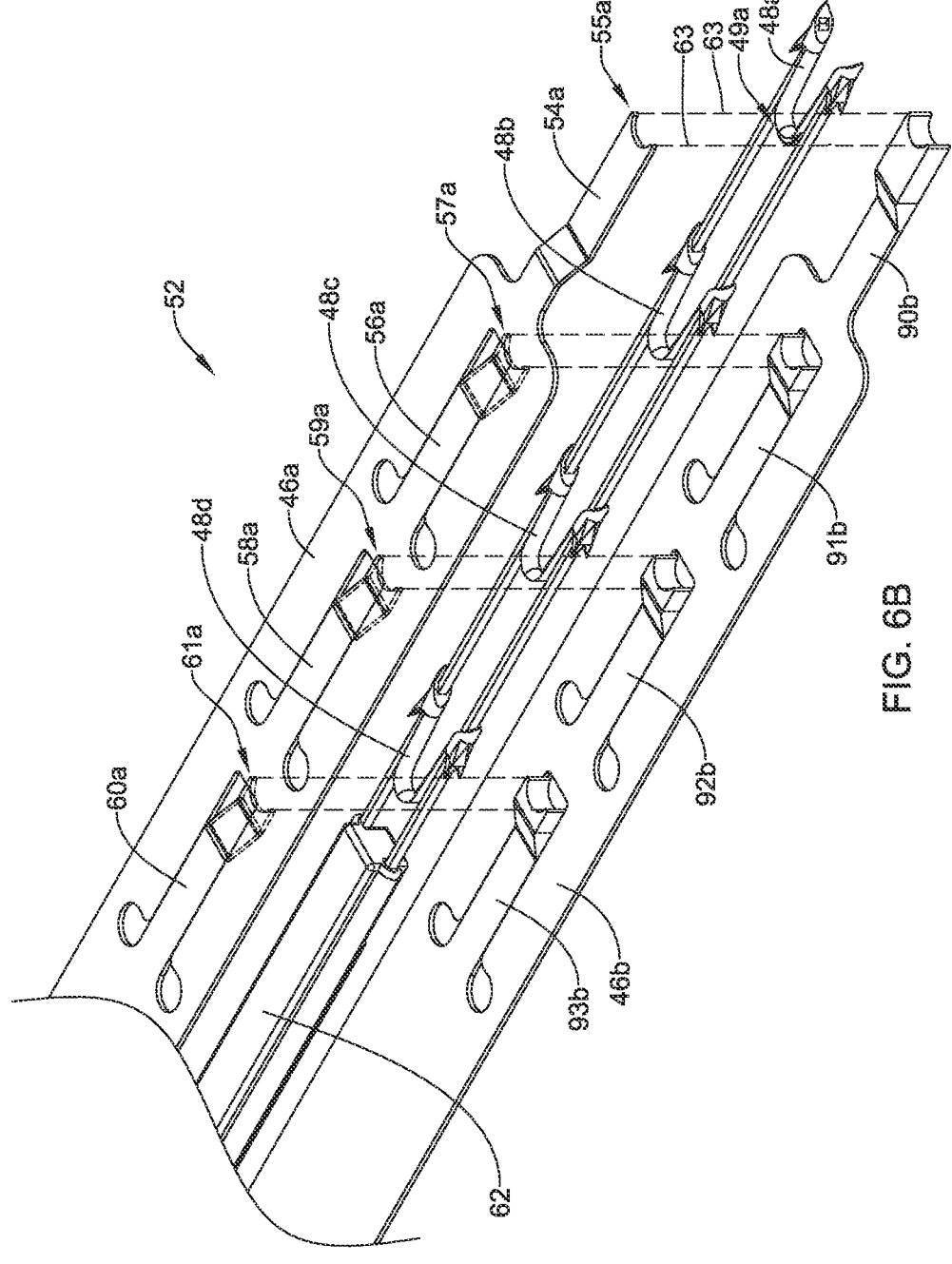
FIG. 6B illustrates an alternative embodiment of the portion of the example implant delivery device shown in FIG. 6A.

FIG. 6B illustrates an alternative embodiment of the fixation member actuation assembly 52 shown in FIG. 6A. Like FIG. 6A, FIG. 6B illustrates the first longitudinal member 46*a* having engagement portions 54*a*/56*a*/58*a*/60*a*, each of which are disposed and aligned along the first longitudinal member 46*a*. Further, the first longitudinal member 46*a* may have an engagement portion for each fixation member initially loaded into the stapling instrument 32. Additionally, FIG. 6B further illustrates the fixation members 48*a*/48*b*/48*c*/48*d* threaded onto the first rail 50*a* and the second rail 50*b*. FIG. 6B also illustrates the second longitudinal member 46*b* having engagement portions 90*b*/

91*b*/92*b*/93*b*, each of which are disposed and aligned along the second longitudinal member 46*b*. The engagement portions 90*b*/91*b*/92*b*/93*b* may be aligned with each fixation member in addition to also being aligned with the engagement portions 54*a*/56*a*/58*a*/60*a* of the first longitudinal member 46*a*.

Further, in some examples disclosed herein (such as the example shown in FIG. 6B), the second longitudinal member 46*b* shown in FIG. 6B may not translate relative to the first longitudinal member 46*a*, the first rail 50*a* and/or the second rail 50*b* during the deployment of the fixation members into the implant target site. Rather, the second longitudinal member 46*b* may be held stationary as the first longitudinal member 46*a*, the first rail 50*a* and/or the second rail 50*a* are actuated to deploy the fixation members 48*a*/48*b*/48*c*/48*d* into the implant target site. Further, in some instances the engagement portions 90*b*/91*b*/92*b*/93*b* may be held stationary as the first longitudinal member 46*a*, the first rail 50*a* and/or the second rail 50*a* are actuated to deploy the fixation members 48*a*/48*b*/48*c*/48*d* into the implant target site. However, in other instances, the engagement portions 90*b*/91*b*/92*b*/93*b* may flex toward or away from the first rail 50*a* and the second rail 50*b*, but not move proximally or distally, as the first longitudinal member 46*a*, the first rail 50*a* and/or the second rail 50*a* are actuated to deploy the fixation members 48*a*/48*b*/48*c*/48*d* into the implant target site.

FIG. 7 illustrates a portion of the fixation member actuation assembly 52. In particular, FIG. 7 shows the second longitudinal member 46*b*, the first rail 50*a* and the second rail 50*b* (for clarity, the first longitudinal member 46*a* is not shown in FIG. 7). Further, FIG. 7 illustrates the fixation member 48*b* threaded (e.g., loaded) onto the first rail 50*a* and the second rail 50*b* with the first rail 50*a* extending through an aperture of the first anchor portion of the fixation member 48*b* and the second rail 50*b* extending through an aperture of the second anchor portion of the fixation member 48*b*. The fixation member 48*b* is shown engaged with the engagement member 56*b*, as described above. Further yet, FIG. 7 illustrates the fixation member 48*a* spaced apart from the first rail 50*a* and the second rail 50*b* (e.g., the fixation member 48*a* has not yet been threaded (e.g., loaded) onto the first rail 50*a* or the second rail 50*b*). It can be appreciated that FIG. 7 illustrates the apertures 68*a* and 68*b* (the actual aperture 68*b* is obscured in FIG. 7) extending through the anchor portions of the fixation member 48*a* which may permit the fixation member 48*a* to be threaded (e.g., loaded) onto the first rail 50*a* and the second rail 50*b*. Additionally, FIG. 7 shows the distal end portions 51*a*/51*b* of the first rail 50*a* and the second rail 50*b*, respectively.

Figure 8:
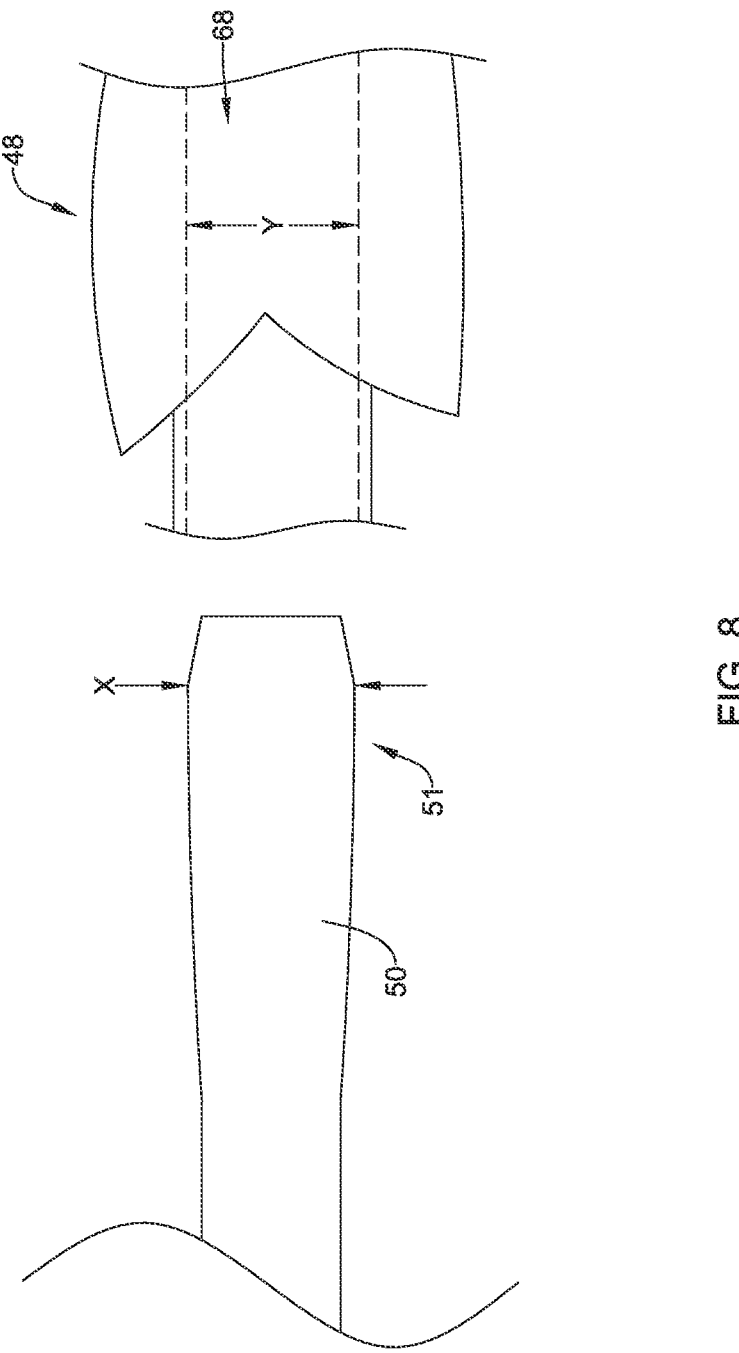
FIG. 8 illustrates another portion of an example implant delivery device.

FIG. 8 illustrates a close up of the distal end 51 of a rail 50. It can be appreciated that the rail 50 shown in FIG. 8 may represent either the first rail 50*a* or the second rail 50*b* of the fixation member actuation assembly 52 (and the distal end 51 may represent the distal end 51*a*/51*b* of the first rail 50*a* or the second rail 50*b*), described above. Additionally, FIG. 8 illustrates that the distal end 51 may include an enlarged portion (e.g. a protuberance) having a width "X" measured perpendicular to the longitudinal axis of the rail 50 which is larger than the portion of the rail 50 immediately proximal of the enlarged portion. The rail 50 may, if desired, have a tapered distal end that tapers from the enlarged portion to a smaller width to facilitate loading fixation members 48 onto the rail 50 from the distal end of the rail 50.

FIG. 8 further illustrates an example fixation member 48 aligned with the rail 50. The fixation member 48 may represent any of the fixation members 48*a*/48*b*/48*c*/48*d* described above. Further, FIG. 8 illustrates that the aperture of the fixation member 48 may have a width "Y" measured parallel to the width X of the rail 50, and thus perpendicular to the longitudinal axis of the rail 50. The aperture 68 may represent the aperture 68*a*/68*b*, described above, through which the rail 50 may extend.

In some examples, it can be appreciated that the width Y may be sized to provide a press fit or interference fit between a surface of the rail 50 at width X of the rail 50 and an inner surface of the aperture 68 at width Y of the fixation member 48. In other words, the dimension Y may be slightly less than the dimension X. For example, the dimension Y may be 0.0005 inches less than the dimension X, or about 0.001 inches less than the dimension X, or about 0.0015 inches less than the dimension X, or about 0.002 inches less than the dimension X, or about 0.0025 inches less than the dimension X, or about 0.003 inches less than the dimension X. It can be appreciated that providing a slight friction fit between the rail 50 and the surface of the fixation member defining the aperture 68 may prevent the fixation member 48 from prematurely sliding off the rail 50, while also permitting the fixation member 48 to be removed from the rail 50 when sufficient force is applied to the fixation member 48. It is noted that the proximal portion of the rail 50 proximal of the enlarged portion may have a width less than the width Y of the aperture 68 to freely slide along the rail 50 when threaded thereon.

Figure 8A:
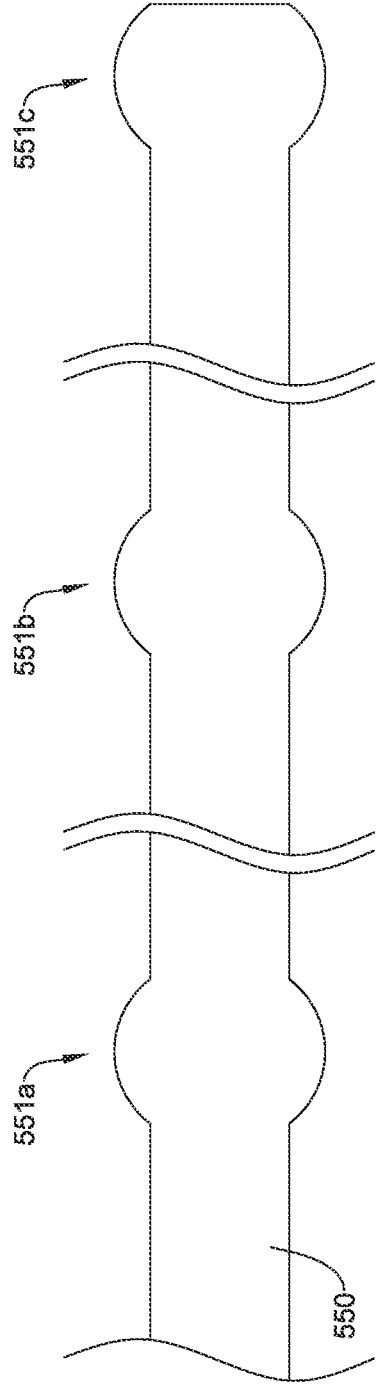
FIG. 8A illustrates an alternative rail for the implant delivery device.

In another embodiment, the rail 50 may include additional enlarged portions, with an enlarged portion configured to engage each fixation member 48 loaded thereon. For instance, the rail 50 may include an enlarged portion (e.g., bump or protrusion) for each of the fixation members 48 initially loaded onto the rail 50. For instance, the rail 50 may include 4, 6, 8, 10 or more enlarged portions spaced along the length of the rail 50. For example, FIG. 8A illustrates another example rail 550 having a plurality of enlarged portions (e.g., bumps or protrusions) relative to portions of the rail 50 extending between the enlarged portions. The rail 550 may be similar in form and function to the rail 50 described above. However, it can be appreciated from FIG. 8A that the rail 550 may include multiple enlarged portions 551*a*/551*b*/551*c* aligned along the longitudinal axis of the rail 550. The enlarged portions 551*a*/551*b*/551*c* may be spaced apart longitudinally from one another along the rail 550 with portions of the rail having a width less than the width Y of the aperture 68 extending between the enlarged portions 551*a*/551*b*/551*c*. The enlarged portions 551*a*/551*b*/551*c* may be spaced apart longitudinally from one another along the rail 550 at the same distance the fixation members 48 are spaced apart along the rail 550. Each of the enlarged portions 551*a*/551*b*/551*c* may have a width measured perpendicular to the longitudinal axis of the rail 550 which is larger than the portion of the rail 550 immediately proximal of the enlarged portion (similar to the width X described above with respect to FIG. 8). It can be further appreciated that each of the enlarged portions 551*a*/551*b*/551*c* may be designed to align with each of multiple fixation members 48*a*/48*b*/48*c*/48*d* (not shown in FIG. 8A, but described above), respectively, when loaded onto the rail 550. As described above with respect to FIG. 8, the width of each of the enlarged portions 551*a*/551*b*/551*c* may be sized to provide a press fit between a surface of the rail 550 and an inner surface of an aperture extending through each of the fixation members 48*a*/48*b*/48*c*/48*d*, through which the rail 550 extends through. It can be appreciated that providing a slight friction fit between the rail 550 and the surface of the aperture of the fixation members 48*a*/48*b*/48*c*/48*d* may prevent the fixation members 48a/48b/48c/48d from prematurely sliding off the rail 550, while also permitting the fixation members 48a/48b/48c/48d to be removed from the rail 550 when sufficient force is applied to each of the fixation members 48a/48b/48c/48d. Each of the enlarged portions 551a/551b/551c may have an arcuate shape extending outward from the surface of the rail 550 between adjacent enlarged portions 551a/551b/551c. In other instances the enlarged portions 551a/551b/551c may taper outward in a distal direction to an outermost extent having the width X. Further, each of the enlarged portions 551a/551b/551c of the rail 550 may, if desired, have a tapered distal end that tapers distally from the outermost extent of the enlarged portion to a smaller width to facilitate loading fixation members 48 onto the rail 550 from the distal end of the rail 550.

Figure 9:
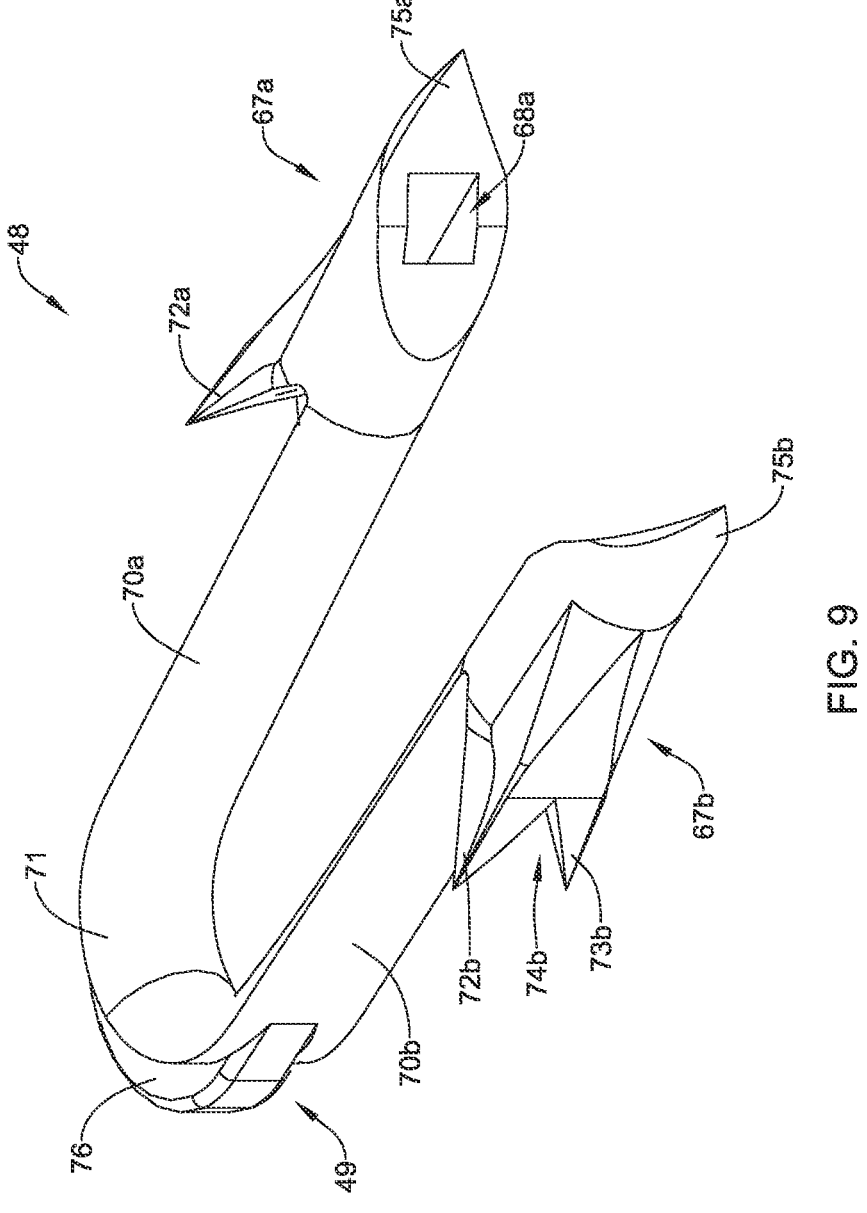
FIG. 9 illustrates a perspective view of an example fixation member.

FIG. 9 is a perspective view illustrating an exemplary fixation member 48 in accordance with the present disclosure (the fixation member 48 may represent the fixation members 48a/48b/48c/48d described above). Although the various parts of exemplary fixation member 48 are depicted in relative proportion to other parts of fixation member 48, other configurations in size and orientation of the various parts are also contemplated in other examples.

In some examples, fixation member 48 may be in the form of a staple including a first arm 70a, second arm 70b, and a bridge 71 extending between the first and second arms 70a/70b. The bridge 71 may abut, or extend from or adjacent to, the proximal end of the first arm 70a to the proximal end of the second arm 70b. In some examples, the first arm 70a may also include an anchor portion 67a and the second arm 70b may further include an anchor portion 67b. In some examples, the anchor portions 67a/67b may each include a first projection 72a/72b and a second projection 73a/73b, on each of the first anchor portion 67a and the second anchor portion 67b, respectively. The first projection 72a/72b and the second projection 73a/73b, on each of the first anchor portion 67a and the second anchor portion 67b, respectively, may extend out and away from the first arm 70a and the second arm 70b, respectively. Having the first projection 72a/72b and the second projection 73a/73b on each of the first anchor portion 67a and the second anchor portion 67b, respectively, extend out and away may permit the fixation member 48 to engage with tissue, such as tendon tissue, after the fixation member 48 is deployed through an implant and into tissue, such as tendon tissue.

FIG. 9 further illustrates that the first projection 72b and the second projection 73b of the second anchor portion 67b may define a second notch 74b positioned between the first projection 72b and the second projection 73b of the second anchor portion 67b. It can be appreciated that the fixation member 48 may include a similar notch 74a positioned between the first projection 72a and the second projection 73a of the first anchor portion 67a (it is noted that the notch 74a is not visible in the perspective view of the fixation member 48). The first projection 72a, the second projection 73a and the notch 74a (positioned between the first projection 72a and the second projection 73a) are shown in FIG. 10.

FIG. 9 further illustrates the aperture 68a located in the first anchor portion 67a of the fixation member 48. As discussed above, the aperture 68a may extend from a distal end region to a proximal end region of the anchor portion 68a. It can further be appreciated that the aperture 68b may be located in the anchor portion 68b, however, it is obscured from view in FIG. 9. The aperture 68b is shown in FIGS. 10-11. The aperture 68a may open out on a distal surface at the distal end region and the aperture 68a may open out on a proximal surface at the proximal end region of the anchor portion 67a, such that the aperture 68a extends entirely through the anchor portion 67a. Likewise, the aperture 68b may open out on a distal surface at the distal end region and the aperture 68b may open out on a proximal surface at the proximal end region of the anchor portion 67b, such that the aperture 68b extends entirely through the anchor portion 67b.

FIG. 9 further illustrates the fixation member 48 may include a projection 76 positioned along the proximal end region 49 of the fixation member 48. The projection may extend along the bridge portion 71 of the fixation member 48. The projection 76 is more clearly shown in FIG. 10, discussed below.

Figure 10:
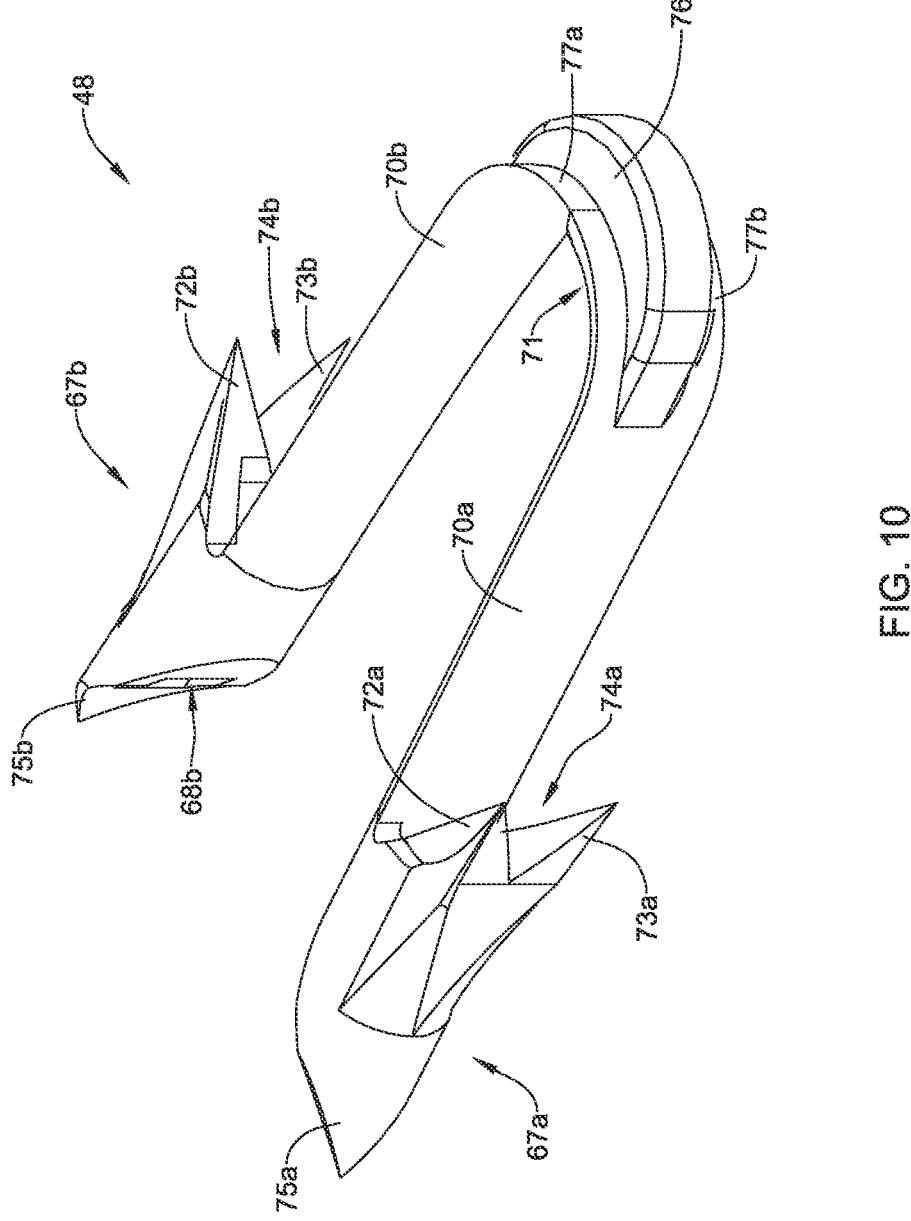
FIG. 10 illustrates a perspective view of the fixation member shown in FIG. 9.
Figure 11:
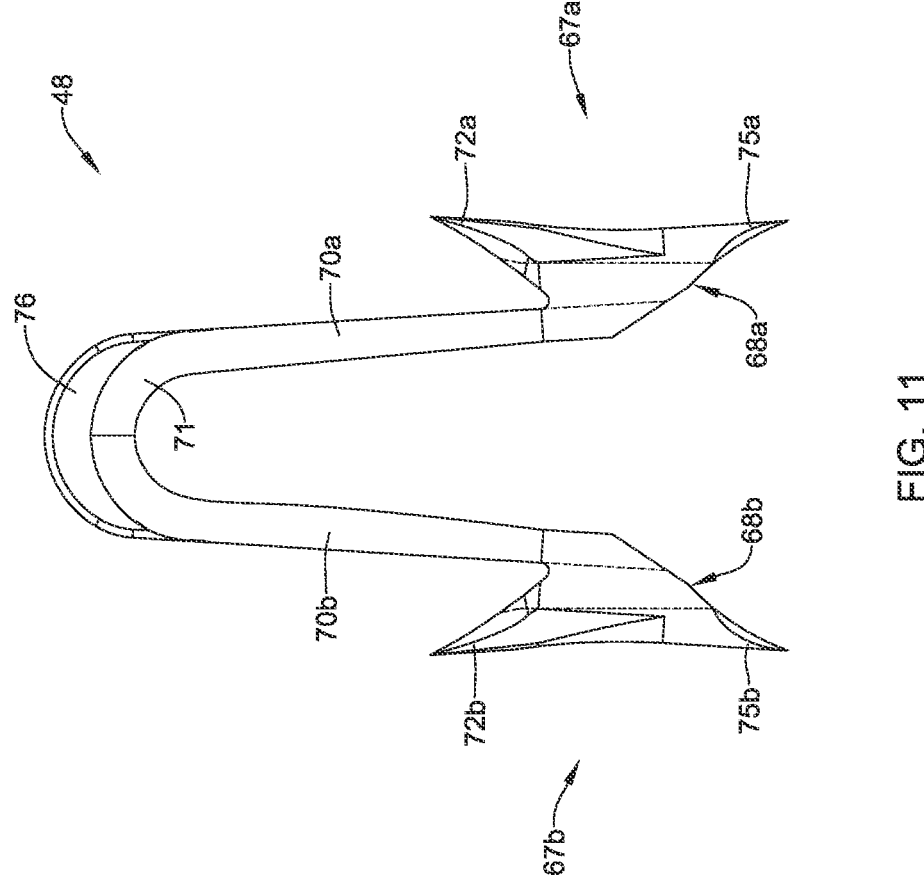
FIG. 11 illustrates a front view of the fixation member shown in FIG. 9.

FIG. 10 shows another perspective view of the fixation member 48 discussed above. FIG. 10 shows the first arm 70a, the second arm 70b and the bridge 71 of the fixation member 48. Additionally, FIG. 10 illustrates the first anchor portion 67a and the second anchor portion 67b of the fixation member 48. Further, as described above, the anchor portions 67a/67b may each include a first projection 72a/72b and a second projection 73a/73b on each of the first anchor portion 67a and the second anchor portion 67b, respectively. Further, FIG. 10 illustrates that the distal end region of each of the anchor portions 67a/67b may include a sharp and/or pointed end 75a/75b. The pointed ends 75a/75b may aid the fixation member 48 in piercing through the implant and into tissue, such as tendon tissue, upon deployment of the fixation member 48.

As discussed above, FIG. 10 further illustrates the projection 76 extending in a proximal direction from the bridge 71. It can be appreciated that the projection 76 may divide the proximal face of the bridge 71 into a first engagement face 77a and a second engagement face 77b with the projection 76 arranged therebetween. Each of the first engagement face 77a and the second engagement face 77b may face proximally to engage a distally facing surface of the engagement portions 54a/56a/58a/60a of the first longitudinal member 46a and/or the engagement portions 54b/56b/58b/60b of the second longitudinal member 46b). Each of the first engagement face 77a and the second engagement face 77b may include those portions of the fixation member 48 for which the engagement portions 54a/56a/58a/60a (of the first longitudinal member 46a) and 54b/56b/58b/60b (of the second longitudinal member 46b) may contact. In other words, the engagement portions 54a/56a/58a/60a of the first longitudinal member 46a may engage the first engagement face 77a of each respective fixation member 48 with which they are each aligned, while the engagement portions 54b/56b/58b/60b of the second longitudinal member 46b may engage the second engagement face 77b of each respective fixation member 48 with which they are each aligned.

FIG. 11 illustrates a front view of the fixation member 48 described above. FIG. 11 shows the first arm 70a, the second arm 70b and the bridge 71 of the fixation member 48. Additionally, FIG. 11 illustrates the first anchor portion 67a and the second anchor portion 67b of the fixation member 48. Further, as described above, FIG. 11 shows first projection 72a/72b on each of the first anchor portion 67a and the second anchor portion 67b, respectively (it is noted that the second projection 73a/73b on each of the first anchor portion 67a and the second anchor portion 67b is hidden in FIG. 11 by the first projection 72a and the second projection 72b).

FIG. 11 further illustrates the first aperture 68a and the second aperture 68b, each of which is depicted by dashed lines extending from a distal end region to a proximal end region of each of the first anchor portion 67a and the second anchor portion 67b. Additionally, FIG. 11 illustrates the projection 76 extending away from the proximal end of the bridge 71 of the fixation member 48. FIG. 11 illustrates that the projection 76 may include a convex curved portion which generally matches the convex curve of the bridge 71.

Figure 12:
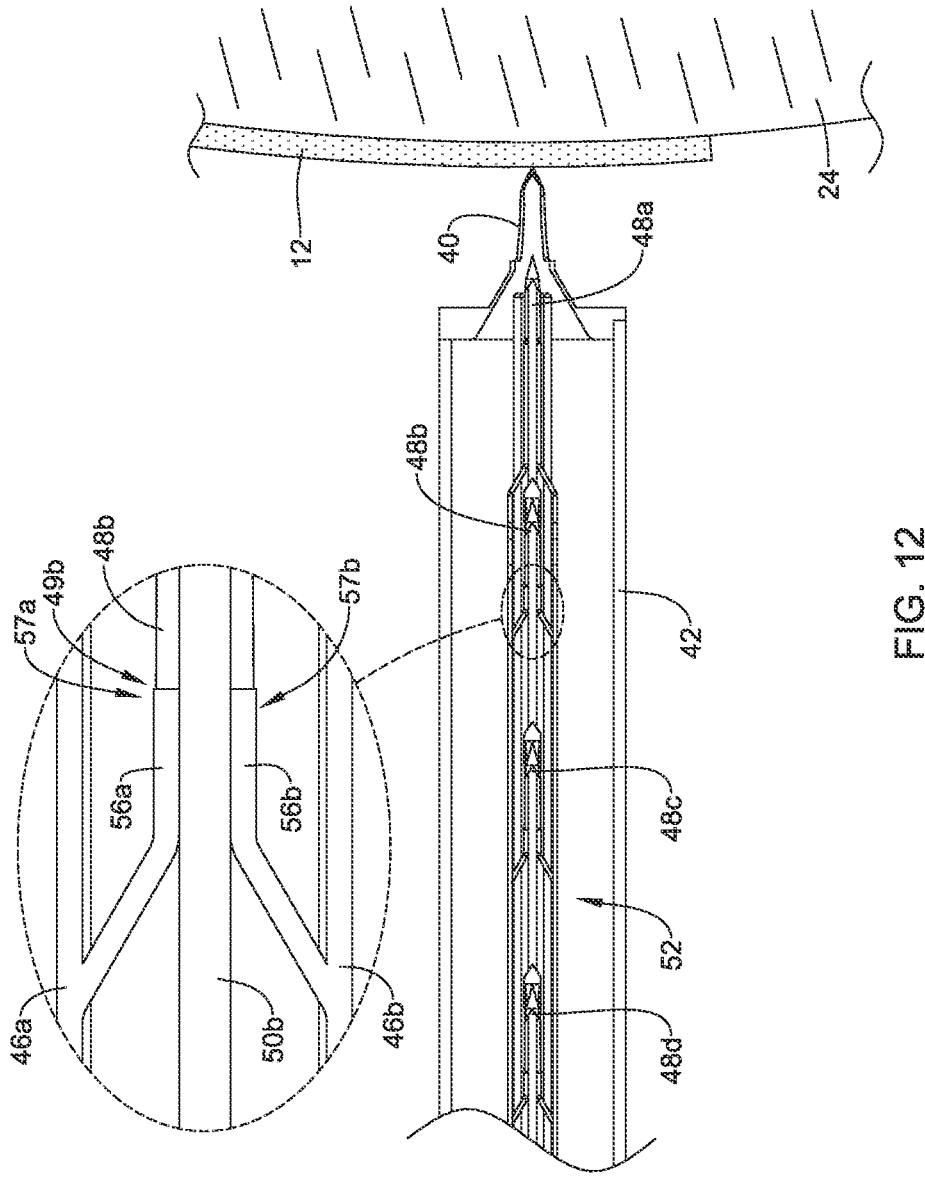
FIGS. 12-17 illustrate an exemplary method of delivering a fixation member with an example implant delivery device at a target site.

FIGS. 12-17 illustrates a series of steps which may be performed by the fixation member actuation assembly 52 to deploy a plurality of fixation members in sequence. As an initial step, FIG. 12 illustrates the outer shaft 42 positioned adjacent to a target site within in the body. Specifically, FIG. 12 illustrates the distal tines 40 of the outer shaft 42 positioned adjacent to an implant 12. For simplicity, FIG. 12 shows the implant 12 positioned over a portion of tendon 24. However, it can be appreciated that the outer shaft 42 may be utilized to deploy the fixation members in a variety of locations such as along the perimeter, the distal end, the proximal end and/or anywhere along the implant 12.

FIG. 12 further illustrates that the actuation assembly 52 is positioned in a resting or ready state, whereby the actuation assembly 52 is positioned such that the fixation member 48a is proximal to the tines 40 of the outer shaft 42. As discussed above, the other fixation members 48b/48c/48d remain aligned with, and spaced apart from, one another along the longitudinal axis of the actuation assembly 52.

Additionally, the detailed view of FIG. 12 illustrates the engagement of the engagement portions 56a/56b with the fixation member 48b. It can be appreciated that in FIG. 12, the fixation member 48b is the second fixation member in a sequence of four fixation members (48a/48b/48c/48d) initially aligned to be deployed. It is understood that the stapling instrument 32 may include additional fixation members similarly arranged, if desired. The detailed view of FIG. 12 further illustrates the engagement portions 56a/56b extending away from the first longitudinal member 46a and the second longitudinal member 46b, respectively, whereby the distal end regions 57a/57b of the engagement portions 56a/56b, respectively, are engaged with the proximal end region 49b of the fixation member 48b. It can be appreciated that each of the remaining fixation members (48a/48c/48d) are similarly engaged with the engagement portions of the first longitudinal member 46a and the second longitudinal member 46b. It is noted that in other embodiments, the stapling instrument 32 may only include one of the first and second longitudinal members 46a/46b. FIG. 12 further illustrates the second rail 50b of the actuation assembly 52 extending through the fixation member 48b. As discussed above, the fixation members 48a/48b/48c/48d may be slidably threaded or loaded onto the first rail 50a and the second rail 50b.

Figure 13:
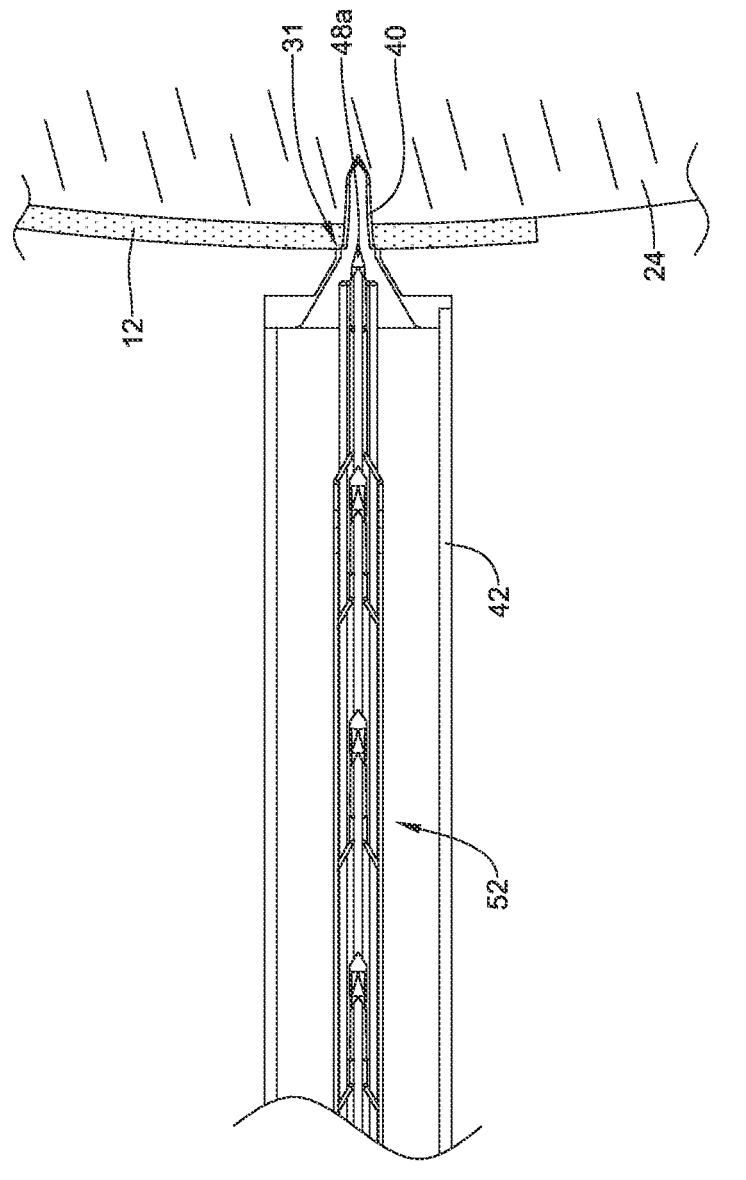

FIG. 13 illustrates another step in the sequential deployment of the fixation members 48a/48b/48c/48d. FIG. 13 illustrates that the clinician has manipulated the handle of the implant stapler 32 to drive the tines 40 of the outer shaft 42 through the implant 12 and into the tendon 24. FIG. 13 further illustrates that the outer shaft 42 has been driven forward to a position in which the distal face 31 of the outer shaft 42 abuts the implant 12. It can be appreciated that from this position, the fixation member 48a of the actuation assembly 52 may be advanced distally through the aperture created by the tines 40, whereby the fixation member 48a is deployed directly into the tendon 24.

Figure 14:
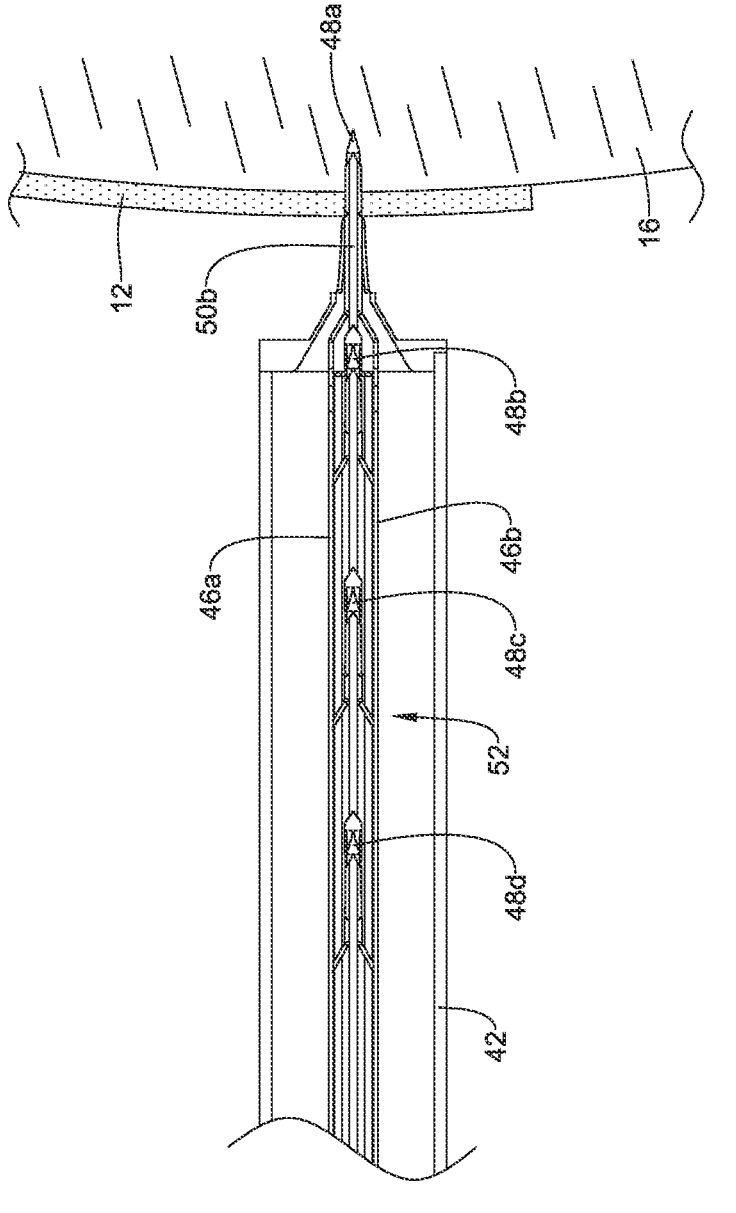

FIG. 14 illustrates another step in the sequential deployment of the fixation members 48a/48b/48c/48d. FIG. 14 illustrates that the clinician has manipulated the handle (e.g., a trigger of the handle assembly) of the implant stapler 32 to drive the leading fixation member 48a into the tendon 24. As will be discussed in greater detail below, it can be appreciated that the handle of the implant stapler 32, through variety of components, may manipulate the first longitudinal member 46a, the second longitudinal member 46b, the first rail 50a and the second rail 50a to distally advance each of the fixation members 48a/48b/48c/48d within the lumen of the outer shaft 42. In other words, FIG. 14 illustrates that as a clinician squeezes a trigger or other actuation mechanism of the handle of the implant stapler 32, each of the components of the actuation assembly 52 (e.g., first longitudinal member 46a, the second longitudinal member 46b, the first rail 50a and the second rail 50a) may be advanced simultaneously in a proximal-to-distal direction relative to the outer shaft 42, thereby moving each of the fixation members 48a/48b/48c/48d distally a corresponding amount. In other words, actuation of the trigger or other actuation mechanism of the handle causes the first longitudinal member 46a, the second longitudinal member 46b, the first rail 50a and the second rail 50b to move together longitudinally in a distal direction relative to the outer shaft 42 to a distal position, simultaneously moving each of the fixation members 48a/48b/48c/48d distally a corresponding amount. This proximal-to-distal advancement may deploy the leading fixation member 48a into the target site as well as advance each of the other fixation members 48b/48c/48d in a proximal-to-distal direction to a next successive position within the outer shaft 42.

Additionally, it can be appreciated that as the clinician actuates the actuation mechanism (e.g., trigger) of the handle to drive the fixation member 48a through the implant 12 and into the tendon tissue 24, the outer shaft 42 may, in some instances, retract proximally such that the tip of the tines may retract from the implant 12. It can be further appreciated that because each of the fixation members 48a/48b/48c/48d may be uniformly spaced from one another, the position of each of the fixation member 48a/48b/48c/48d is fixed relative to the first longitudinal member 46a and the second longitudinal member 46b as they are distally advanced in unison.

Figure 15:
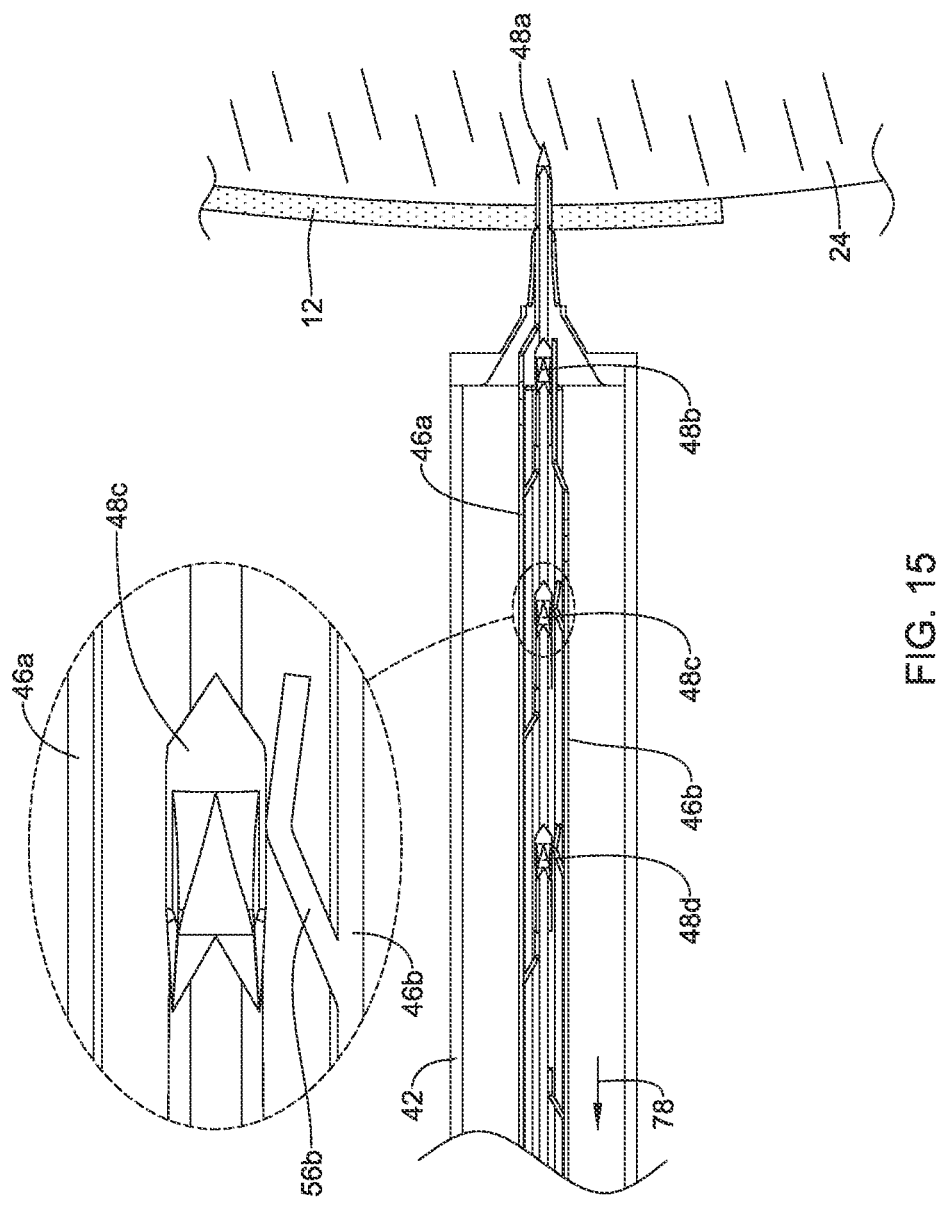

FIG. 15 illustrates another step in the sequential deployment of the fixation members 48a/48b/48c/48d. Once the distalmost (i.e., leading) fixation member has been deployed, the fixation member actuation assembly 52 must be reset to the resting or ready state to prepare the fixation member actuation assembly 52 to advance (e.g., "cycle") another fixation member out of the outer shaft 42, and thus deploy the fixation member from the outer shaft 42 after the first fixation member 48a is deployed into the target site (e.g., the tendon tissue 24).

Specifically, FIG. 15 illustrates that as the clinician releases the actuator on the handle, the second longitudinal member 46b may be retracted proximally (as shown by the arrow 78) relative to the first longitudinal member 46a, the first rail 50a and the second rail 50b. In other words, the second longitudinal member 46b may be retracted proximally while the first longitudinal member 46a, the first rail 50a and the second rail 50b remain stationary. It is noted that the fixation members 48b/48c/48d remaining in the outer shaft 42 also remain stationary while the second longitudinal member 46b is retracted proximally.

The detailed view of FIG. 15 illustrates that as the second longitudinal member 46b is retracted proximally, the engagement portions 54b/56b/58/60b may flex away from the central longitudinal axis of the actuation assembly 52, thereby permitting the engagement portions 54b/56b/58b of the second longitudinal member 46b to deflect and maneuver past the fixation members 48b/48c/48d remaining in the outer shaft 42. For example, the detailed view of FIG. 15 illustrates the engagement portion 56*b* flexing away from the longitudinal axis of the actuation assembly 52 thereby allowing the engagement portion 56*b* to slide past the fixation member 48*c* to a position proximal of the fixation member 48*c*.

As discussed above, as the second longitudinal member 46*b* is shifting proximally, the first longitudinal member 46*a* may be holding the fixation members 46*b*/46*c*/46*d* stationary. In other words, the engagement portions 54*a*/56*a*/58*a*/60*a* of the first longitudinal member 46*a* are contacting first engagement faces 77*a* of the fixation members 46*b*/46*c*/46*c* and thus holding the fixation members 48*a*/48*b*/48*c*/48*d* stationary as the second longitudinal member 46*b* shifts proximally.

It can be further appreciated that a similar embodiment may be employed for steps described in FIG. 15 whereby as the clinician releases the actuator on the handle, the second longitudinal member 46*b*, the first rail 50*a* and the second rail 50*b* (collectively) may be retracted proximally relative to the first longitudinal member 46*a*. In other words, this alternative embodiment may perform as described above for FIG. 15, however, the first relative movement would include the second longitudinal member 46*b*, the first rail 50*a* and the second rail 50*b* retracting proximally to the proximal position while the first longitudinal member 46*a* remains stationary in the distal position.

Figure 16:
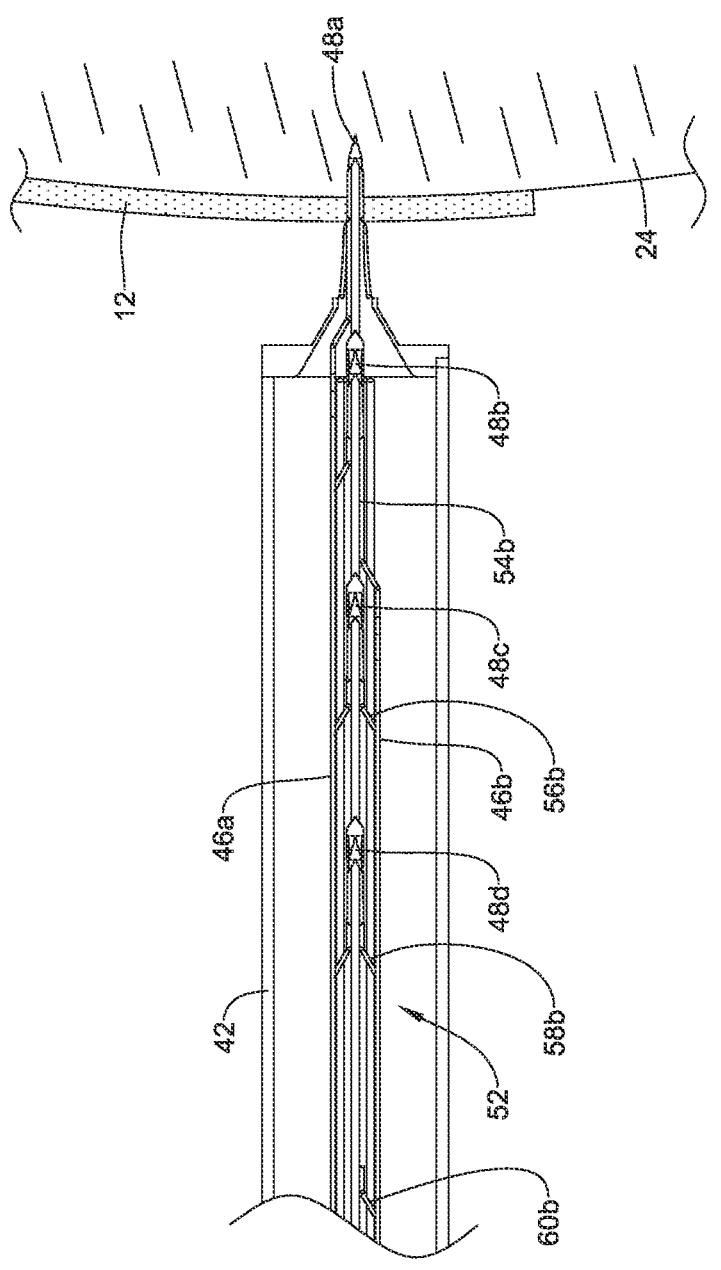

FIG. 16 illustrates another step in the sequential deployment of the fixation members 48*a*/48*b*/48*c*/48*d*. FIG. 16 illustrates that the second longitudinal member 46*b* has shifted proximally to a position in which the engagement members 54*b*/56*b*/58*b* of the second longitudinal member 46*b* are engaged with the fixation member 48*b*/48*c*/48*d*, respectively. In other words, the second longitudinal member 46*b* has shifted proximally to its proximal position, a position in which the engagement members 54*b*/56*b*/58*b* move back toward the central longitudinal axis of the actuation assembly 52 and engage the proximal end regions of the fixation members 48*b*/48*c*/48*d* remaining in the outer shaft 42. Thus, the second longitudinal member 46*b* has returned to its proximal positon, while the first longitudinal member 46*a*, as well as the first and second rails 50*a*/50*b* remain in their distal position. It is noted that that engagement member 60*b* does not engage a fixation member because, after shifting back to its proximal position, there is no longer a fixation member for the engagement portion 60*b* to engage, as each of the remaining fixation members have moved distal one position. This would represent a scenario where the fixation member 48*d* is the proximal-most or last of a series of fixation members to be deployed from the outer shaft 42. It should be noted that while the drawings utilized herein shown a series of four fixation members, more or less than four fixation members may be loaded into the example implant stapler device 32.

As described with respect to FIG. 15, in an alternative embodiment, the second longitudinal member 46*b*, the first rail 50*a* and the second rail 50*b* may be initially retracted (collectively) to their proximal position while only the first longitudinal member 46*a* remains in its distal position.

Figure 17:
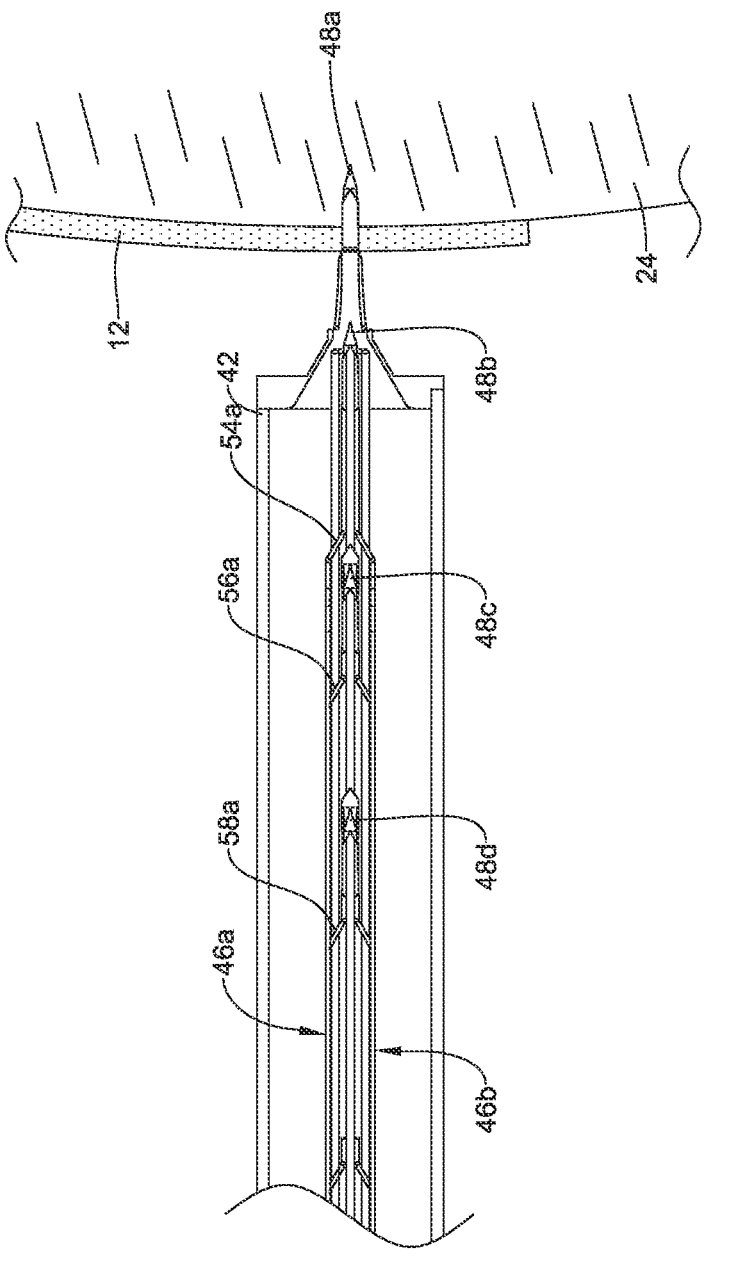

FIG. 17 illustrates another step in the sequential deployment of the fixation members 48*a*/48*b*/48*c*/48*d*. Specifically, FIG. 17 illustrates that further actuation of the actuation mechanism of the handle, such as the clinician releases another component (e.g., a thumb trigger) on the handle, the first longitudinal member 46*a*, the first rail 50*a* and the second rail 50*b* may be retracted proximally relative to the second longitudinal member 46*b* back to their proximal position while the second longitudinal member 46*b* remains stationary at its proximal position. In other words the first longitudinal member 46*a*, the first rail 50*a* and the second rail 50*b* (collectively) may be retracted proximally while the second longitudinal member 46*b* remains stationary and prevents the fixation members 48*b*/48*c*/48*d* from moving within the lumen of the outer shaft 42. While not shown in FIG. 17, it can be appreciated the engagement portions 54*a*/56*a*/58*a* may flex away from the central longitudinal axis of the actuation assembly in order to deflect and slide past and subsequently engage the fixation members 48*b*/48*c*/48*d* (just as the step described above with respect to the second longitudinal member 46*b* flexing past the fixation members as it shifts proximally, as shown in FIG. 15).

Again, as described with respect to FIGS. 15-16, in an alternative embodiment, after retracting the first longitudinal member 46*a*, the first rail 50*a* and the second rail 50*b* back to the proximal position, the second longitudinal member 46*b* may be retracted proximally while the first longitudinal member 46*a*, the first rail 50*a* and the second rail 50*b* (collectively) remain stationary in the proximal position and prevent the fixation members 48*b*/48*c*/48*d* from moving within the lumen of the outer shaft 42.

It can be appreciated that after the first longitudinal member 46*a*, the first rail 50*a* and the second rail 50*b* are retracted back to their proximal position and engage the remaining fixation members 48*b*/48*c*/48*d*, the actuation assembly 52 has completed one "cycle," whereby the lead fixation member 48*a* was deployed into the tendon 24 and the remaining fixation members 48*b*/48*c*/48*d* have moved distally one position in the outer shaft 42 to ready deployment of the next fixation member 48*b*. After the fixation member 48*a* is deployed and the actuation mechanism reset, the outer shaft 42 may be repositioned, whereby the fixation member 48*b* now becomes the lead (i.e., distalmost) fixation member and may be deployed in the same sequence of steps described above with respect to FIGS. 12-17. The cycle may continue with a clinician repositioning the implant stapler 32 and deploying the fixation members until all the fixation members are implanted, without having to remove the implant stapler 32 from an implant site.

In yet another embodiment, the fixation member actuation assembly 52 may include the first and second rails 50*a*/50*b*, and only one longitudinally actuatable longitudinal member (e.g., first longitudinal member 46*a*) configured to incrementally advance the fixation members 48*a*/48*b*/48*c*/48*d* for sequential deployment. In some instances, the fixation member actuation assembly 52 may include the second longitudinal member 46*b* in a fixed position for preventing proximal movement of the fixation members 48*a*/48*b*/48*c*/48*d* while the first longitudinal member 46*a* moves distally to deploy a fixation member and then returns to the proximal position while the second longitudinal member 46*b* prevents the remaining fixation members from proximal movement along the first and second rails 50*a*/50*b*. In this embodiment, the first and second rails 50*a*/50*b* may be configured to move in unison with the first longitudinal member 46*a* in both proximal and distal directions while the second longitudinal member 46*b* remains stationary throughout one complete cycle. Thus, during deployment of the fixation member 48*a*, the first and second rails 50*a*/50*b* may move in unison with the first longitudinal member 46*a* in a distal direction relative to the second longitudinal member 46*b* to advance the first fixation member 48*a*. Thereafter, the first and second rails 50*a*/50*b* may move in unison with the first longitudinal member 46*a* in a proximal direction relative to the second longitudinal member 46*b* to reset for deployment of the next fixation member 48*b*. Accordingly, the second longitudinal member 46*b* may remain in a fixed longitudinal position while the first and second rails 50*a*/50*b* and the first longitudinal member 46*a* cycle between a distal position and a proximal position while sequentially deploying fixation members 48*a*/48*b*/48*c*/48*d* loaded onto the first and second rails 50*a*/50*b*. In other instances, the first and second rails 50*a*/50*b* may be fixed relative to the second longitudinal member 46*a*, such that only the first longitudinal member 46*a* moves in both proximal and distal directions while the second longitudinal member 46*b*, as well as the first and second rails 50*a*/50*b* remain stationary throughout one complete cycle.

Figure 18:
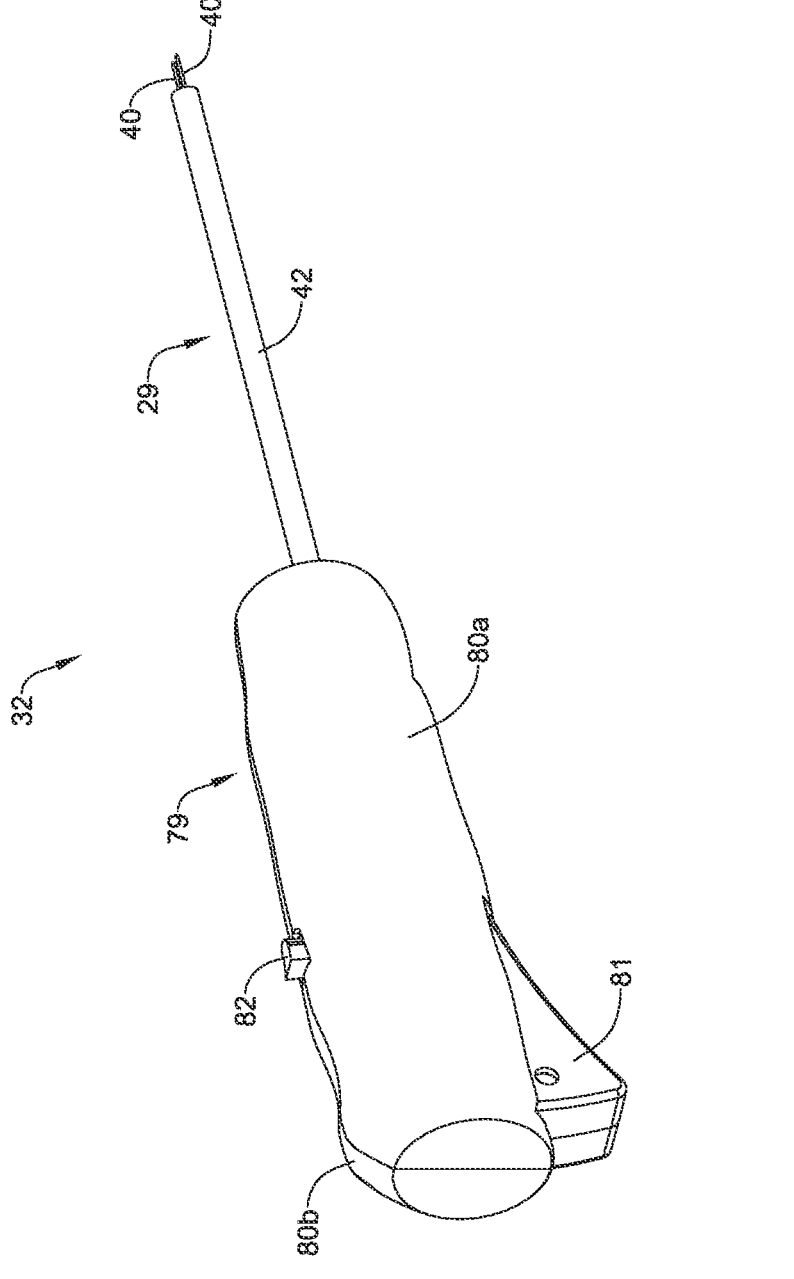
FIG. 18 illustrates an example implant delivery device.

FIG. 18 illustrates an example stapling instrument 32, such as a tendon stapler. The stapling instrument 32 may include a handle 79 coupled to the shaft assembly 29. As discussed above, the shaft assembly 29 may include an outer shaft 42. The outer shaft 42 may include one or more tines 40 extending away from the distal end of the outer shaft 42. The tines 40 may extend parallel to a central longitudinal axis of the outer shaft 42. It can be appreciated, that while not shown in FIG. 18, the fixation member actuation assembly 52 may be positioned within the lumen of the outer shaft 42. As discussed above, the fixation member actuation assembly 52 may include an actuation shaft 62 which extends within the outer shaft 42 and into the handle 79. Attachment of the actuation shaft 62 within the handle 79 will be further discussed below.

FIG. 18 further illustrates that the handle 79 may include a first housing member 80*a* and a second housing member 80*b*. It can be appreciated that the first housing member 80*a* and the second housing member 80*b* may be designed to mate with one another in a "clam shell" configuration. As will be described below, the handle 79 may include a variety of components which are designed to manipulate the fixation member actuation assembly 52 located in the outer shaft 42.

FIG. 18 further illustrates that the handle 79 may include an actuation mechanism, such as a lever 81 and a thumb trigger 82 for actuating the fixation member actuation assembly 52. While the actuation mechanism is illustrated as including a lever and a thumb trigger, it is noted that other forms of actuator may be utilized for the actuation mechanism to manipulate the fixation member actuation assembly 52 during use. It can be appreciated that the handle 79 may be designed such that a clinician may grasp the handle 79 with one hand and actuate both the lever 81 (via squeezing) and the thumb trigger 82 (via manipulation with the thumb of the grasping hand).

Figure 19:
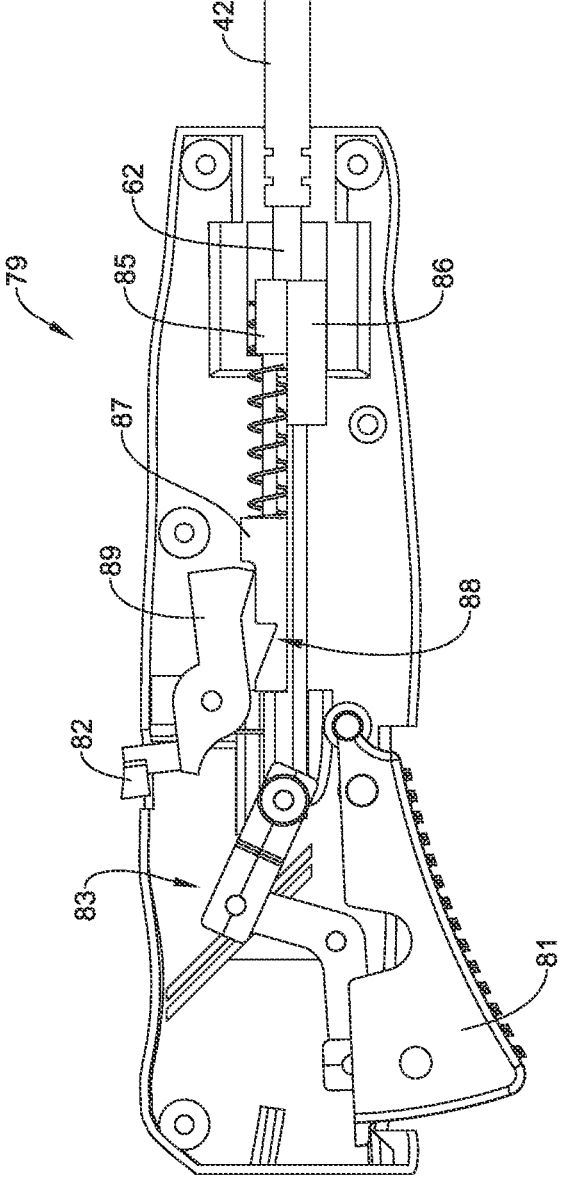
FIGS. 19-22 illustrate the implant delivery device shown in FIG. 18 being actuated in a sequence of steps to deliver a fixation member.

FIG. 19 illustrates a cross-section of the inner components of the handle 79. For example, FIG. 19 illustrates further illustrates the lever 81 and the thumb trigger 82 as described above. Further, FIG. 19 illustrates that the lever 81 may be coupled to a first linkage assembly 83. The first linkage assembly 83 may be further coupled to a first deployment member 86. Additionally, FIG. 19 illustrates that the handle 79 may include second linkage assembly 88, whereby second linkage assembly 88 includes a pivoting linkage 89 coupled to stepped actuation linkage 87. The stepped actuation linkage 87 may be coupled to a second deployment member 85. Additionally, the first deployment member 86 and/or the second deployment member 85 may be coupled to the actuation shaft 62. For example, the second deployment member 85 may be fixedly coupled to each of the first longitudinal member 46*a*, the first rail 50*a*, and the second rail 50*b*, and moveable therewith. The first deployment member 86 may be fixedly coupled to the second longitudinal member 46*b* and moveable therewith.

Figure 20:
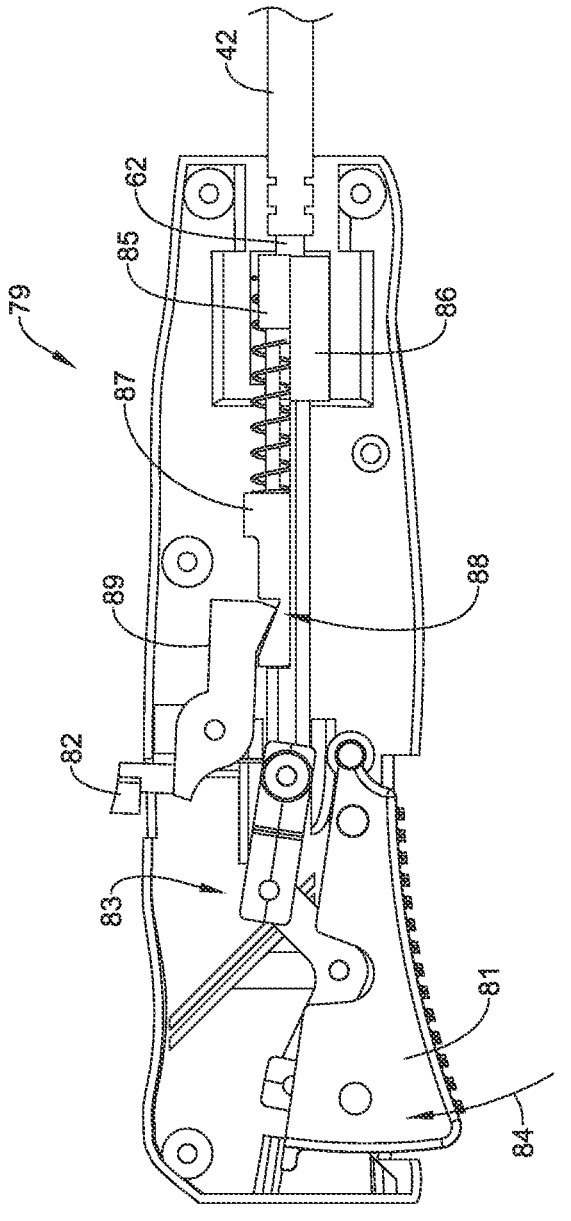
Figure 21:
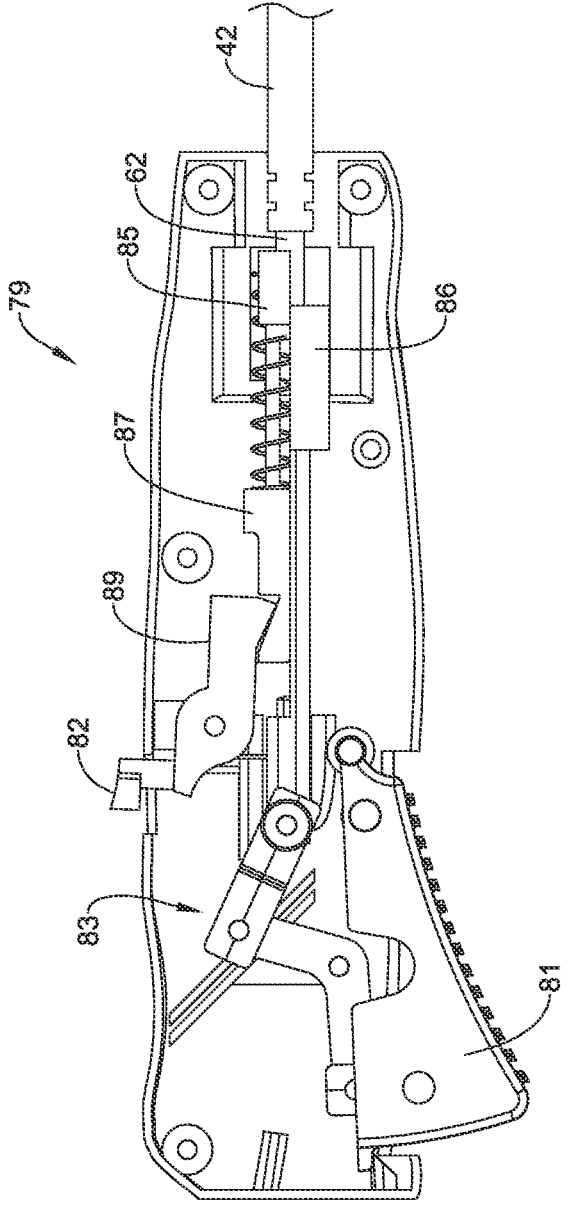
Figure 22:
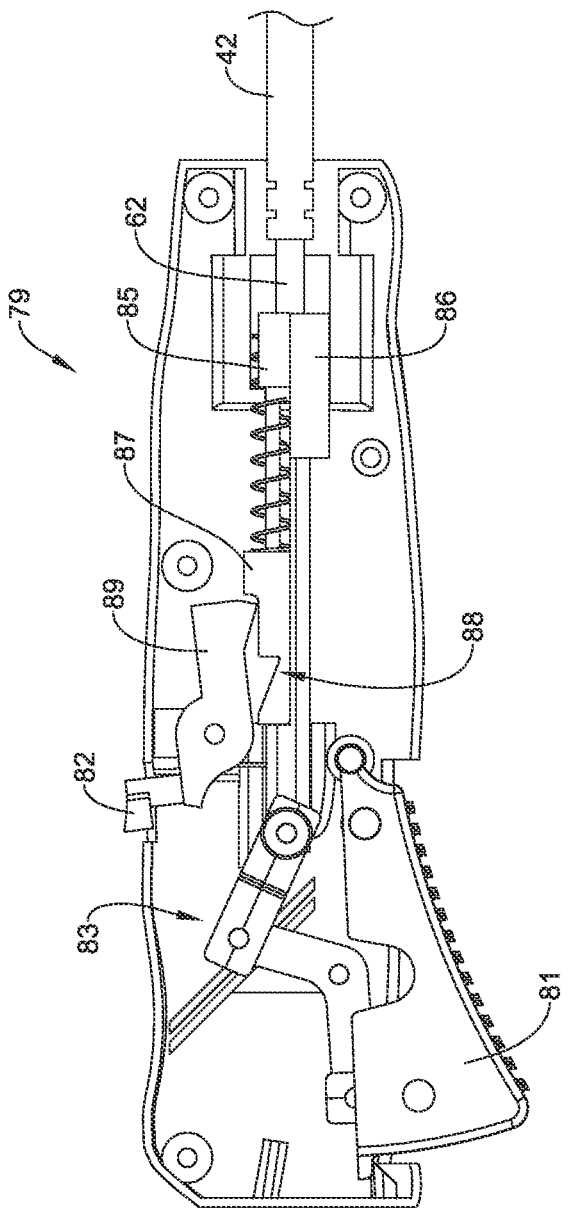

FIGS. 20-22 illustrate the coordinated movement of various inner components within the handle 79 which permit the fixation member actuation assembly 52 to sequentially deploy the fixation members from the outer shaft 42. In other words, the mechanical movement of the inner components of the actuation mechanism within the handle 79, as shown in FIGS. 19-22, correspond to the cycling of the first longitudinal member 46*a*, the second longitudinal member 46*b*, the first rail 50*a* and the second rail 50*b* to sequentially deploy the fixation members from the outer shaft 42. It can be appreciated that, prior to actuating the lever 81 or the thumb trigger 82, a clinician may initially position the handle 79 adjacent a target site and push the handle 79 into the target site, thereby driving the tines 40 through the implant 12 and into the target tissue (e.g., humeral head or tendon). This step is described above with respect to FIG. 13 in which the actuation mechanism is in the ready state. FIGS. 20-22 describe the actuation of the components of the handle 79 after the initial penetration of the tines 40 at the target site (e.g., tendon).

FIG. 20 illustrates the squeezing of the lever 81 of the handle 79. The squeezing of the lever 81 is depicted by the arrow 84. The squeezing of the lever 81 causing an actuation of the first linkage assembly 83. It can be appreciated that the actuation of the first linkage assembly may result in a proximal-to-distal movement of both the first deployment member 86 and the second deployment member 85, thereby moving the first longitudinal member 46*a*, the second longitudinal member 46*b*, the first rail 50*a*, and the second rail 50*b* distally in unison. Accordingly, the proximal-to-distal movement of the first and second deployment members 86/85 may translate the actuation shaft 62, having the rails 50*a*/50*b* secured thereto in a distal direction. It can be appreciated that the distal movement of the actuation shaft 62 may shift each of the fixation members in a distal direction relative to the outer shaft 42. The distal movement of the fixation member actuation assembly 52 may deploy the leading fixation member out of the outer shaft 42.

FIG. 21 illustrates a clinician releasing the lever 81 after squeezing the lever 81 to deploy the initial leading fixation member out of the outer shaft 42. This step begins the "cycling" of the fixation member actuation assembly 52 back to the proximal position, or ready state, to load a subsequent fixation member in the leading position of the fixation member actuation assembly 52 for subsequent deployment from the outer shaft 42. As illustrated in FIG. 21, as the lever 81 is released, the first linkage assembly 83 shifts such that the first deployment member 86 retracts in a proximal direction within respect to the second deployment member 85. The retraction of the first deployment member 86 corresponds to the proximal retraction of the second longitudinal member 46*b* back to its proximal position, as described above. Further, it can be appreciated from FIG. 20 that because the second linkage assembly 88 maintains the second deployment member 85 stationary, the first longitudinal member 46*a*, the first rail 50*a* and the second rail 50*b* remain in a stationary position as the second longitudinal member 46*b* is retracted. For example, the pivoting link 89 may contact the stepped actuation member 87 to prevent proximal movement of the stepped actuation member 87.

FIG. 22 illustrates the subsequent actuation of the thumb trigger 82 after release of the lever 81, as described with respect to FIG. 21. FIG. 22 illustrates that actuation of the thumb trigger 82 (at the clinician's discretion), may rotate the pivoting link 89 out of engagement from the stepped actuation member 87, thereby permitting proximal movement of the stepped actuation member 87 via proximal force application by a spring or other biasing member. Rotation of the pivoting link 89 may result in the proximal retraction of the stepped actuation member 87, which in turn may permit the second deployment member 85 to be proximally retracted. Moreover, the proximal retraction of the second deployment member 85 may permit the first longitudinal member 46a, the first rail 50a and the second rail 50b of the actuation assembly 52 to proximally retract in unison back to their proximal position in the ready state, thereby completing a full cycle of advancing the fixation members within the outer shaft 42 to a position in which a successive fixation member is ready to be deployed at the target site. As described above, it can be appreciated that as the first longitudinal member 46a, the first rail 50a and the second rail 50b are proximally retracted back to their proximal position, the second longitudinal member 46b may remain stationary in its proximal position, thereby maintaining the position of the fixation members within the lumen of the outer shaft 42.

Figure 23:
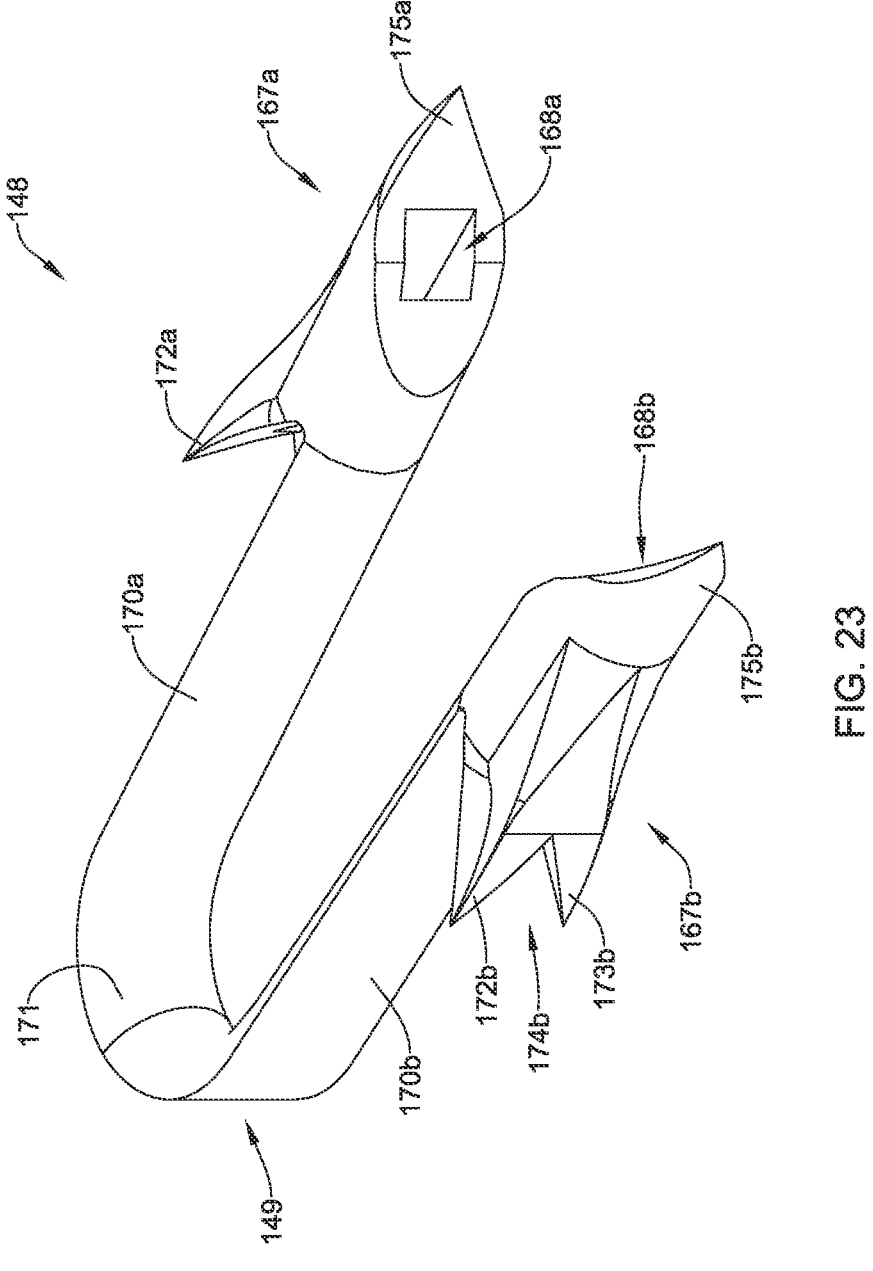
FIG. 23 illustrates a perspective view of another example fixation member.

FIG. 23 illustrates another example fixation member 148 (i.e., staple) which may be utilized with the implant stapler 32 described herein. FIG. 23 is a perspective view in accordance with the present disclosure (the fixation member 148 may represent the fixation members 48a/48b/48c/48d described above). Although the various parts of exemplary fixation member 148 are depicted in relative proportion to other parts of fixation member 148, other configurations in size and orientation of the various parts are also contemplated in other examples.

In some examples, fixation member 148 includes a first arm 170a, a second arm 170b, and a bridge 171 extending between the first and second arms 170a/170b. The bridge 171 may abut, or extend from or adjacent to, the proximal end of the first arm 170a to the proximal end of the second arm 170b. In some examples, the first arm 170a may also include an anchor portion 167a and the second arm 170b may further include an anchor portion 167b. In some examples, the anchor portions 167a/167b may each include a first projection 172a/172b and a second projection 173a/173b, on each of the first anchor portion 167a and the second anchor portion 167b, respectively (it is noted that the second projection 173a is not visible in FIG. 23, but is similar to the projection 173b). The first projection 172a/172b and the second projection 173a/173b, on each of the first anchor portion 167a and the second anchor portion 167b, respectively, may extend out and away from the first arm 170a and the second arm 170b, respectively. Having the first projection 172a/172b and the second projection 173a/173b, on each of the first anchor portion 167a and the second anchor portion 167b, respectively, extend out and away may permit the fixation member 148 to engage with tissue, such as tendon tissue, after the fixation member 148 is deployed through an implant and into the tissue, such as tendon tissue.

FIG. 23 further illustrates that the first projection 172b and the second projection 173b of the second anchor portion 167b may define a second notch 174b positioned between the first projection 172b and the second projection 173b of the second anchor portion 167b. It can be appreciated that the fixation member 148 may include a notch 174a positioned between the first projection 172a and the second projection 173a of the first anchor portion 167a (it is noted that the notch 174a is not visible in the perspective view of the fixation member 148, but is similar to the notch 174b).

Figure 24:
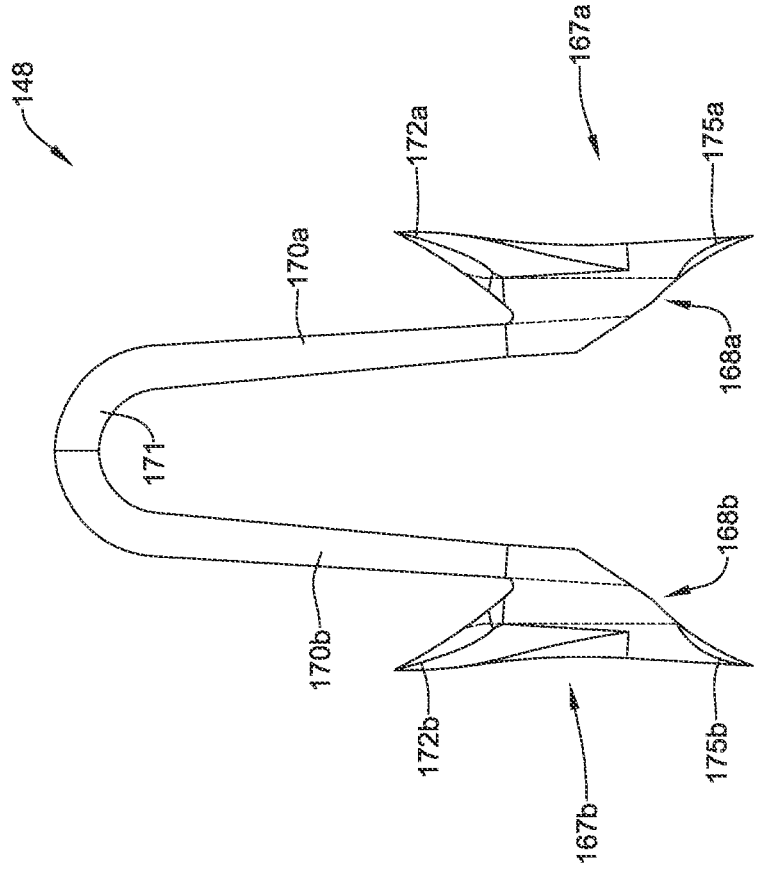
FIG. 24 illustrates a front view of the fixation member shown in FIG. 23.

FIG. 23 further illustrates that the aperture 168a located in the first anchor portion 167a of the fixation member 148. As discussed above, the aperture 168a may extend from a distal end region to a proximal end region of the anchor portion 168a. It can further be appreciated that the aperture 168b may be located in the engagement region 168b, however, it is obscured from view in FIG. 23. The aperture 168b is shown in FIG. 24. The aperture 168a may open out on a distal surface at the distal end region and the aperture 168a may open out on a proximal surface at the proximal end region of the anchor portion 167a, such that the aperture 168a extends entirely through the anchor portion 167a. Likewise, the aperture 168b may open out on a distal surface at the distal end region and the aperture 168b may open out on a proximal surface at the proximal end region of the anchor portion 167b, such that the aperture 168b extends entirely through the anchor portion 167b.

FIG. 24 illustrates a front view of the fixation member 148 described above. FIG. 24 shows the first arm 170a, the second arm 170b and the bridge 171 of the fixation member 148. Additionally, FIG. 24 illustrates the first anchor portion 167a and the second anchor portion 167b of the fixation member 148. Further, as described above, FIG. 24 shows first projection 172a/172b on each of the first anchor portion 167a and the second anchor portion 167b, respectively (it is noted that the second projection 173a/173b on each of the first anchor portion 167a and the second anchor portion 167b is hidden in FIG. 24 by the first projection 172a and the second projection 172b).

FIG. 24 further illustrates the first aperture 168a and the second aperture 168b, each of which is depicted by dashed lines extending from a distal end region to a proximal end region of each of the first anchor portion 167a and the second anchor portion 167b.

Figure 25:
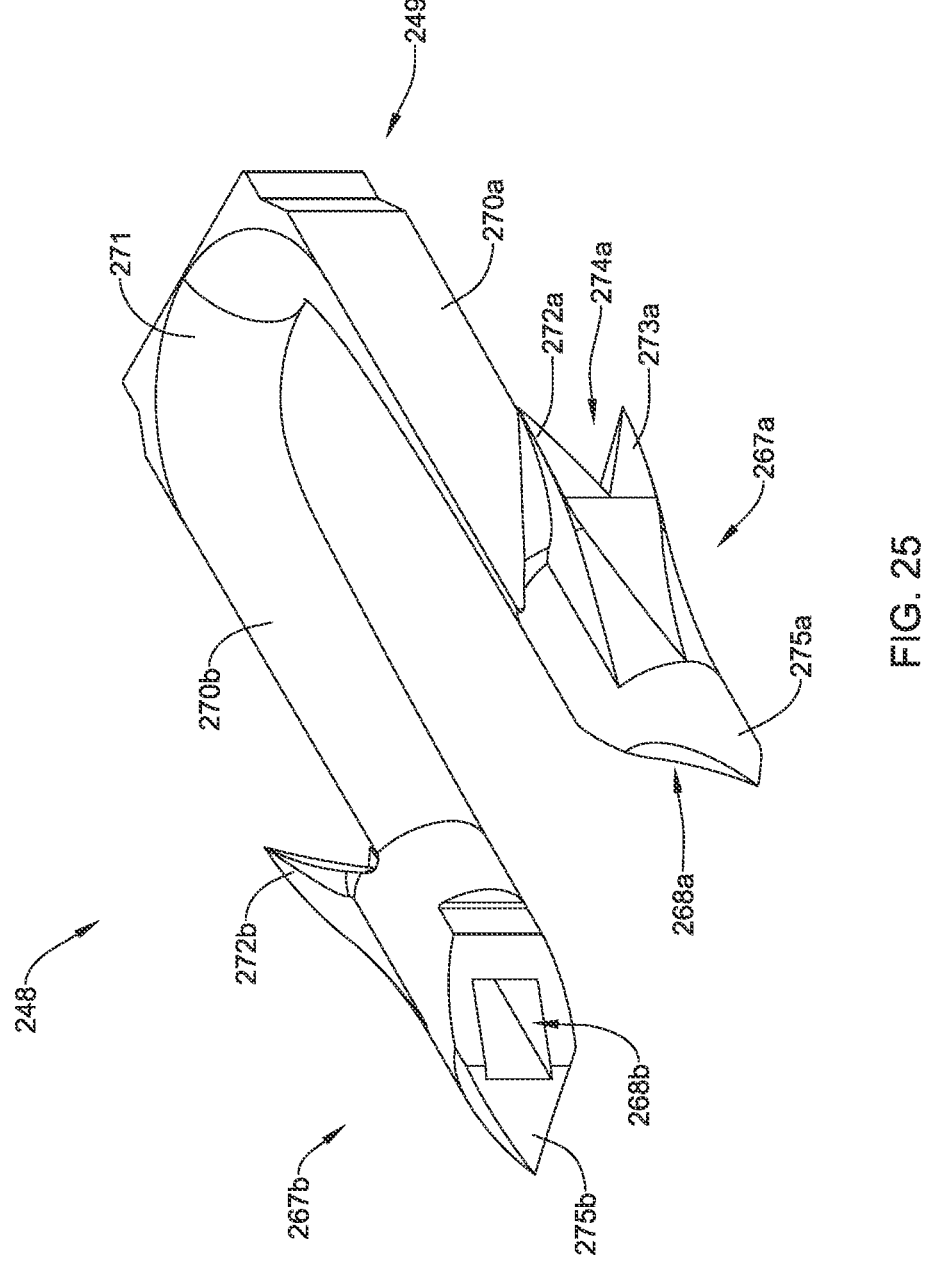
FIG. 25 illustrates a perspective view of another example fixation member.

FIG. 25 illustrates another example fixation member 248 (i.e., staple) which may be utilized with the implant stapler 32 described herein. FIG. 25 is a perspective view in accordance with the present disclosure (the fixation member 248 may represent the fixation members 48a/48b/48c/48d described above). Although the various parts of exemplary fixation member 248 are depicted in relative proportion to other parts of fixation member 248, other configurations in size and orientation of the various parts are also contemplated in other examples.

In some examples, fixation member 248 includes a first arm 270a, a second arm 270b, and a bridge 271 extending between the first arm 270a and the second arm 270b. The bridge 271 may abut, or extend from or adjacent to, the proximal end of the first arm 270a to the proximal end of the second arm 270b. In some examples, the first arm 270a may also include an anchor portion 267a and the second arm 270b may further include an anchor portion 267b. In some examples, the anchor portions 267a/267b may each include a first projection 272a/272b and a second projection 723a/273b, on each of the first anchor portion 267a and the second anchor portion 267b, respectively (it is noted that the second projection 273b is not visible in FIG. 25, but is similar to the projection 273b). The first projection 272a/272b and the second projection 273a/273b, on each of the first anchor portion 267a and the second anchor portion 267b, respectively, may extend out and away from the first arm 270a and the second arm 270b, respectively. Having the first projection 272a/272b and the second projection 273a/273b, on each of the first anchor portion 267a and the second anchor portion 267b, respectively, extend out and away may permit the fixation member 248 to engage with tissue, such as tendon tissue, after the fixation member 248 is deployed through an implant and into the tissue, such as tendon tissue.

FIG. 25 further illustrates that the first projection 272a and the second projection 273a of the first anchor portion 267a may define a first notch 274a positioned between the first projection 272a and the second projection 273a of the first anchor portion 267a. It can be appreciated that the fixation member 248 may include a similar notch 274b positioned between the first projection 272b and the second projection 273b of the second anchor portion 267b (it is noted that the notch 274b is not visible in the perspective view of the fixation member 248, but is similar to the notch 274a). The first projection 272b, the second projection 273b and the notch 274b (positioned between the first projection 272b and the second projection 273b) is shown in FIG. 26.

FIG. 25 further illustrates that the aperture 268b located in the first anchor portion 267b of the fixation member 248. As discussed above, the aperture 268b may extend from a distal end region to a proximal end region of the anchor portion 268b. It can further be appreciated that the aperture 268a may be located in the anchor portion 267a, however, it is obscured from view in FIG. 25. The aperture 268a is shown in FIGS. 26-27. The aperture 268a may open out on a distal surface at the distal end region and the aperture 268a may open out on a proximal surface at the proximal end region of the anchor portion 267a, such that the aperture 268a extends entirely through the anchor portion 267a. Likewise, the aperture 268b may open out on a distal surface at the distal end region and the aperture 268b may open out on a proximal surface at the proximal end region of the anchor portion 267b, such that the aperture 268b extends entirely through the anchor portion 267b.

Figure 26:
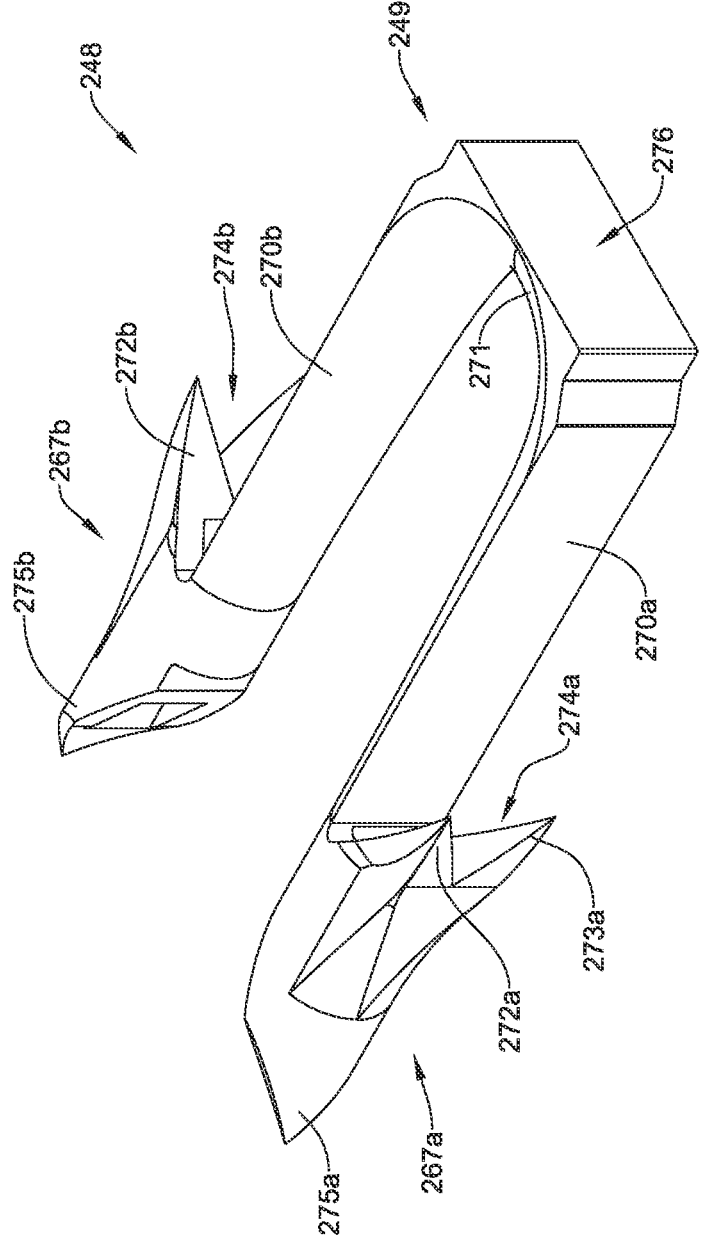
FIG. 26 illustrates a perspective view of the fixation member shown in FIG. 25.
Figure 27:
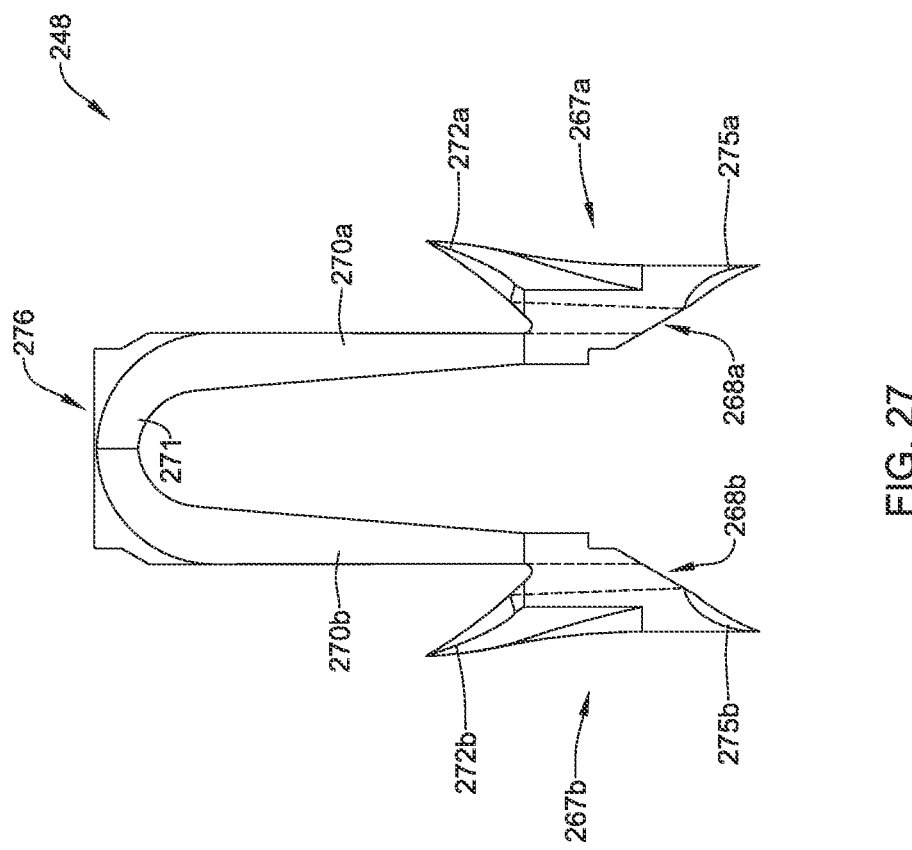
FIG. 27 illustrates a front view of the fixation member shown in FIG. 25.

FIG. 26 shows another perspective view of the fixation member 248 discussed above. FIG. 26 shows the first arm 270a, the second arm 270b and the bridge 271 of the fixation member 248. Additionally, FIG. 26 illustrates the first anchor portion 267a and the second anchor portion 267b of the fixation member 248. Further, as described above, the anchor portions 267a/267b may each include a first projection 272a/272b and a second projection 273a/273b, on each of the first anchor portion 267a and the second anchor portion 267b, respectively. Further, FIG. 26 illustrates that the distal end region of the each of the anchor portions 267a/267b may generally include a sharp and/or pointed end 275a/275b. The pointed ends 275a/275b may aid the fixation member 248 in piercing through the implant and into tissue, such as tendon tissue, upon deployment of the fixation member 248.

FIG. 26 further illustrates that the proximal end 249 of the fixation member 248 may include a flat surface 276 positioned along the proximal side of the bridge 271. The flat surface 276 may be a planar surface arranged perpendicular to the longitudinal axis of the outer shaft 42 of the stapler instrument 32 when loaded therein. When utilized with the example implant stapler 32 described herein, it can be appreciated that the flat surface 276 may define the portion of the fixation member 248 for which the engagement portions 54a/56a/58a/60a (of the first longitudinal member 46a) and 54b/56b/58b/60b (of the second longitudinal member 46b) may contact. Referring to FIG. 6 and the accompanying description above, the engagement portions 54a/56a/58a/60a of the first longitudinal member 46a and the engagement portions 54b/56b/58b/60b of the second longitudinal member 46b may be configured with flat, planar edges configured to engage the flat face 276 of each respective fixation member 248 with which they are each aligned.

FIG. 27 illustrates a front view of the fixation member 248 described above. FIG. 27 shows the first arm 270a, the second arm 270b and the bridge 271 of the fixation member 248. Additionally, FIG. 27 illustrates the first anchor portion 267a and the second anchor portion 267b of the fixation member 248. Further, as described above, FIG. 27 shows the first projection 272a/272b on each of the first anchor portion 267a and the second anchor portion 267b, respectively (it is noted that the second projection 273a/273b on each of the first anchor portion 267a and the second anchor portion 267b is hidden in FIG. 27 by the first projection 272a and the second projection 272b).

FIG. 27 further illustrates the first aperture 268a and the second aperture 268b, each of which is depicted by dashed lines extending from a distal end region to a proximal end region of each of the first anchor portion 267a and the second anchor portion 267b. Additionally, FIG. 27 illustrates the flat face 276 extending along the proximal side of the bridge 271 of the fixation member 248 generally perpendicular to the longitudinal axis extending along the fixation member 248 in a proximal-to-distal direction.

FIGS. 28-31 illustrate another exemplary implant stapler 300 and a series of steps showing the loading and deployment of an example fixation member 304a.

Figure 28:
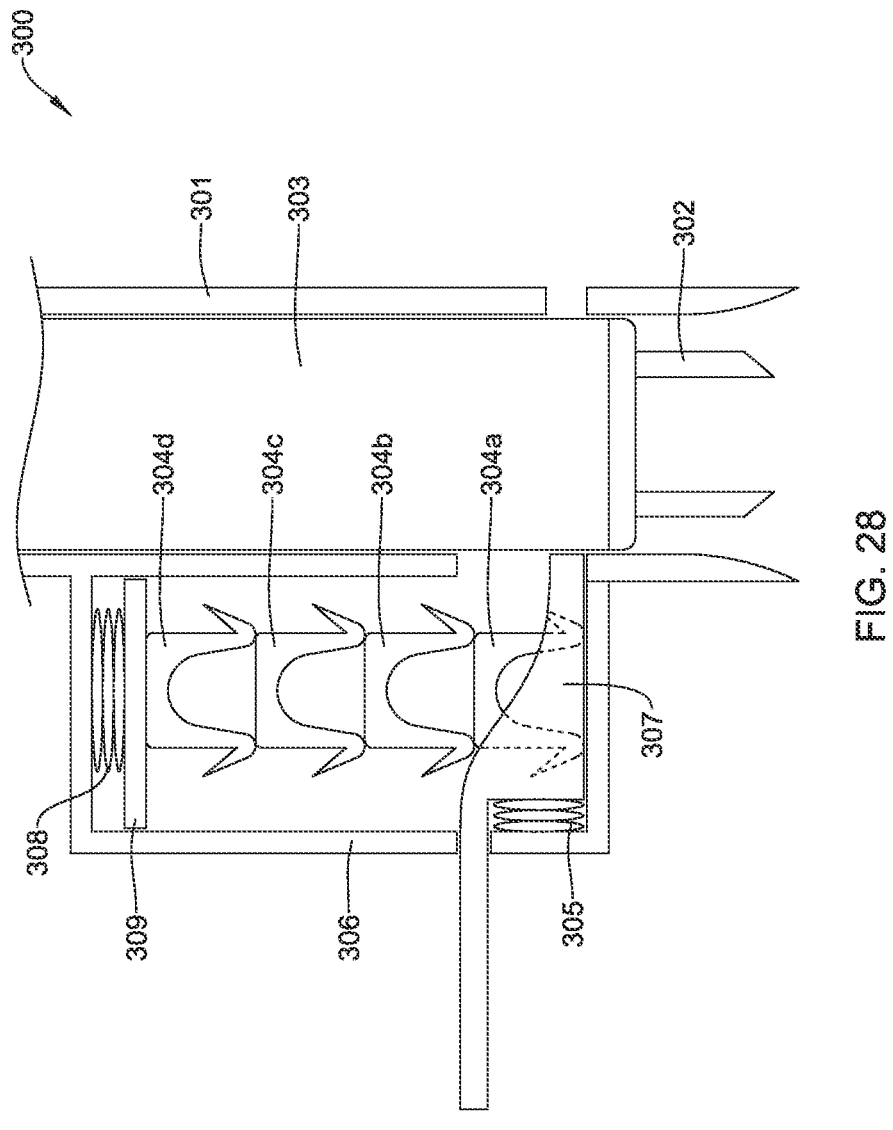
FIGS. 28-31 illustrate an exemplary method of delivering a staple with another example implant delivery device.

FIG. 28 illustrates an implant stapler 300 including a shaft assembly 303 positioned within the lumen of an outer shaft 301. The shaft assembly 303 may include a plurality of tines 302 extending distally away from the shaft assembly 303.

FIG. 28 further illustrates that implant stapler 300 may include a stapler magazine 306 coupled to the outer shaft 301. The stapler magazine 306 may house a plurality of implant staples 304a/304b/304c/304d, each of which may be vertically stacked atop one another, i.e., longitudinally in line with one another. Additionally, the stapler magazine 306 may include a staple pusher spring 308 coupled to a staple pusher 309. It can be appreciated that the staple pusher spring 308 and the staple pusher 309, collectively, may exert a downward force on the implant staples 304a/304b/304c/304d.

FIG. 28 further illustrates that the implant stapler 300 may include a staple cam spring 305 coupled to a staple cam 307. It can be appreciated from FIG. 28 that the lead staple 304a may be nested within the body of the staple cam 307. It can further be appreciated that the staple cam spring 305 may be designed to exert a force on the staple cam 307 which shifts the staple 307, for example, into the outer shaft 301 (this action will be show in detail below in FIG. 29). It can be further appreciated that actuation of the staple cam 307 may be initiated via a clinician manipulating a trigger or other type of actuator.

Figure 29:
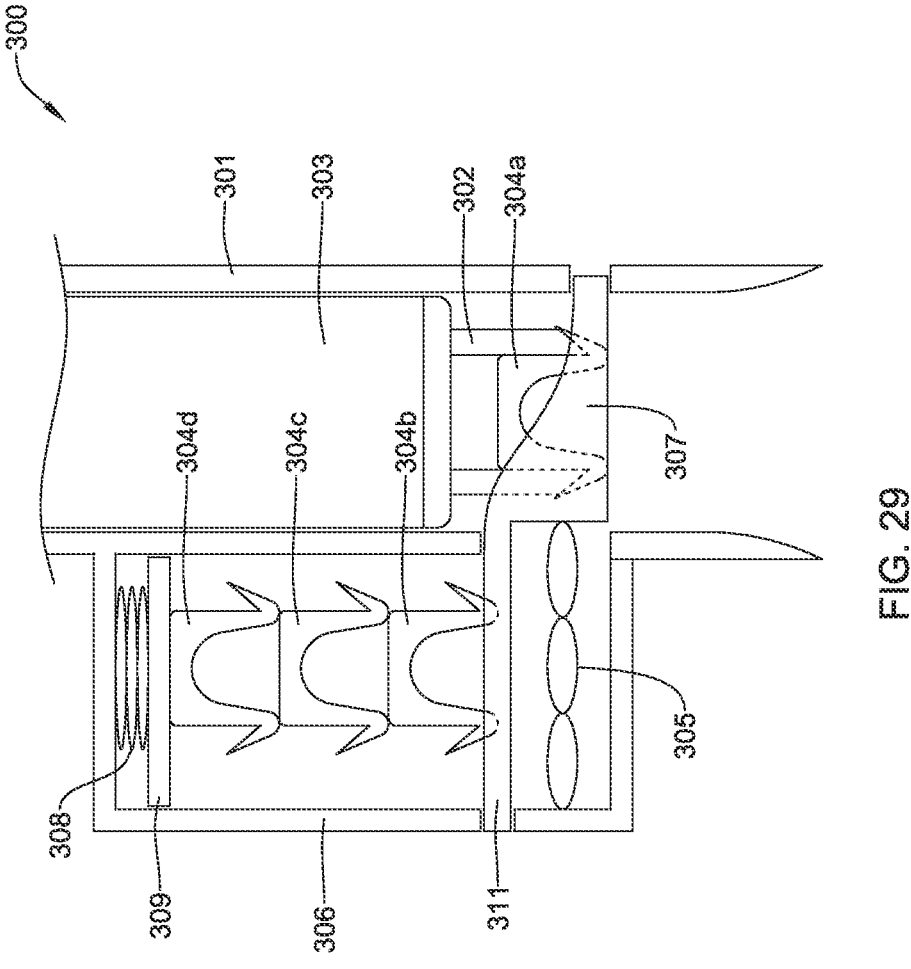

As discussed above, FIG. 29 illustrates that actuation of the staple cam 307 to load the staple 304a into the outer shaft 301 (and, more specifically, into a position in which the tines 302 of the shaft assembly 303. It can be appreciated that the shaft assembly 303 may have to have been manipulated to seat the staple 304a within the tines 302. FIG. 29 illustrates the staple 304a positioned within the tines 302 after the manipulation of the shaft assembly 303). As discussed above, to shift the staple 304a from the magazine 306 into the outer shaft 301, a clinician may actuate a trigger which releases the staple cam 307. Upon release, the staple cam spring 305 may expand, thereby laterally shifting the staple cam 307 and the lead staple 304a into the outer shaft 301. FIG. 29 illustrates that the staple cam 307 may include a projection 311 which is designed to hold the subsequent staple (e.g., staple 304b) stationary which the staple cam 307 shifts the lead staple 304a into the outer shaft 301.

Figure 30:
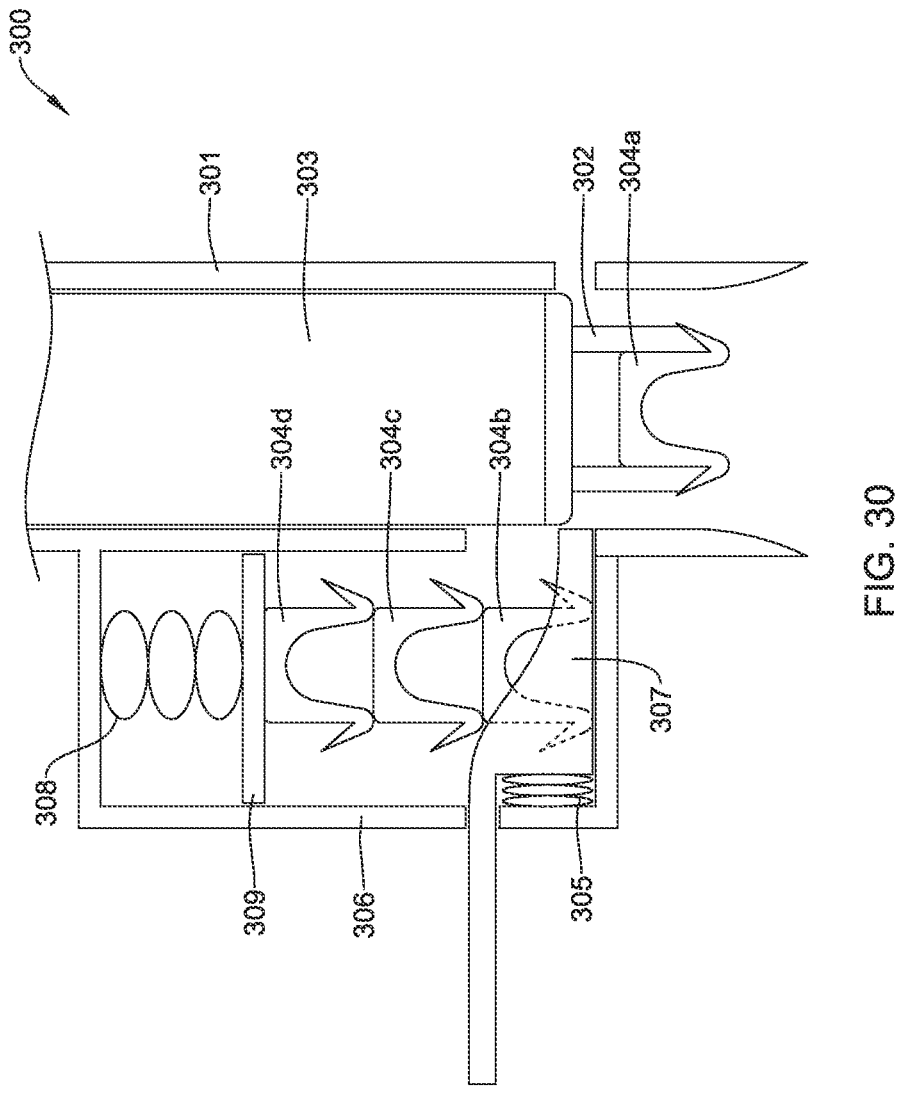

FIG. 30 illustrates the implant stapler 300 being manipulated to shift the pushrod assembly 303 downward (e.g., the initial shifting of the pushrod assembly 303 downward to deploy the lead staple 304a). As the pushrod assembly 303 shifts downward, the engagement of the pushrod assembly 303 with the profile of the cam 307 may force the cam 307 laterally outward and back into the magazine 306. The shifting of the cam 307 is depicted by the arrow 310 in FIG. 30. In other words, as the pushrod assembly 303 is shifted downward (to deploy the staple 304a), the outer surface of the pushrod assembly 303 may contact the staple cam 307 and shift it back into the magazine 307, whereby the next staple 304b may be loaded into the staple cam 307.

Figure 31:
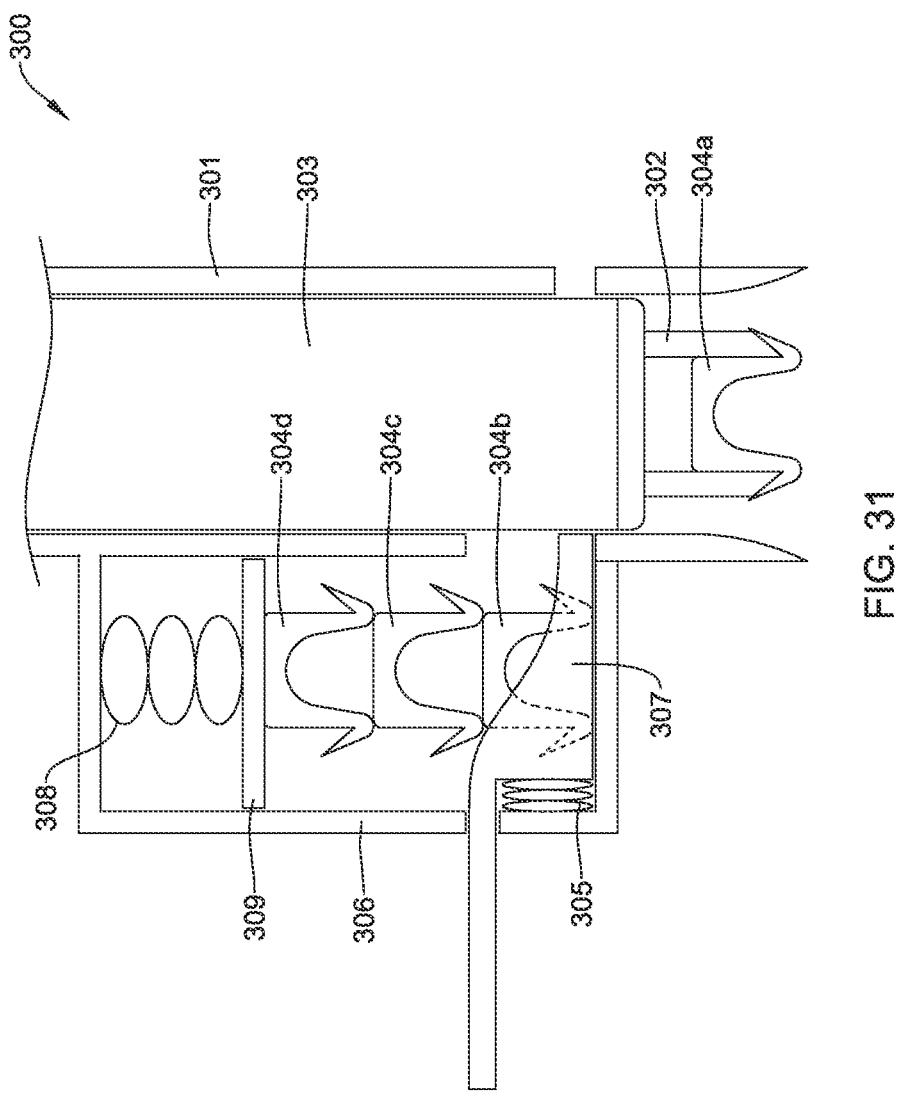

FIG. 31 illustrates the staple cam 307 being shifted to a position in the magazine 306 which permits the staple 304b to be loaded into the staple cam 307. It can be appreciated that the staple 304b may be loaded into the staple cam 307 via the downward force applied via the staple pusher spring 308 and the staple pusher 309. Additionally, FIG. 31 illustrates the staple 304a being further advanced within the outer shaft 301 to a position in which it may be further deployed into an implant and/or target site. It can be appreciated that the sequence of steps described with respect FIGS. 28-31 may be repeated to sequentially deploy and reload multiple staples without having to reload and/or remove the implant stapler 300 from the patient.

Figure 32:
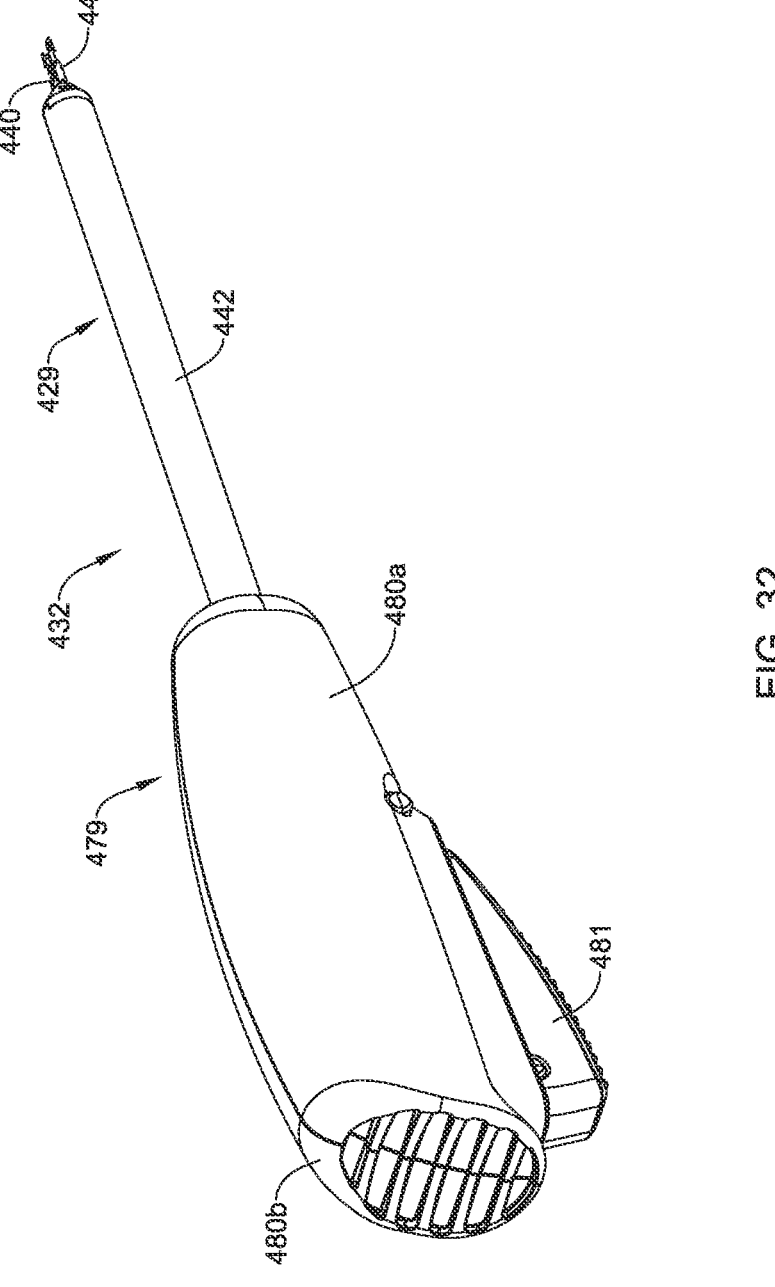
FIG. 32 illustrates another example implant delivery device.

FIG. 32 illustrates another example stapling instrument 432. The stapling instrument 432 may be similar in form and function to the tendon stapler 32 described herein. For example, the stapling instrument 432 may include a handle 479 coupled to a shaft assembly 429. The shaft assembly 429 may include an outer shaft 442. The outer shaft 442 may include one or more tines 440 extending away from the distal end of the outer shaft 442. The tines 440 may extend parallel to a central longitudinal axis of the outer shaft 442. Further, it can be appreciated that a fixation member actuation assembly 452 (shown in an exploded view in FIG. 33) may be positioned within the lumen of the outer shaft 442. As will be discussed in greater detail herein, the fixation member actuation assembly 452 may include an actuation shaft 462 (shown in an exploded view in FIG. 33) which extends within the outer shaft 442 and into the handle 479. Attachment of the actuation shaft 462 within the handle 479 will be discussed in greater detail below.

FIG. 32 further illustrates that the handle 479 may include a first housing member 480a and a second housing member 480b. It can be appreciated that the first housing member 480a and the second housing member 480b may be designed to mate with one another in a "clam shell" configuration. As will be described below, the handle 479 may include a variety of components which are designed to manipulate the fixation member actuation assembly 452 positioned within the outer shaft 442.

FIG. 32 further illustrates that the handle 479 may include an actuation mechanism, such as a lever 481 for actuating the fixation member actuation assembly 452. While the actuation mechanism is illustrated as including a lever 481, it is noted that other forms of an actuator may be utilized for the actuation mechanism to manipulate the fixation member actuation assembly 452 during use. It can be appreciated that the handle 479 may be designed such that a clinician may grasp the handle 479 with one hand and actuate the lever 481 (via squeezing).

Figure 33:
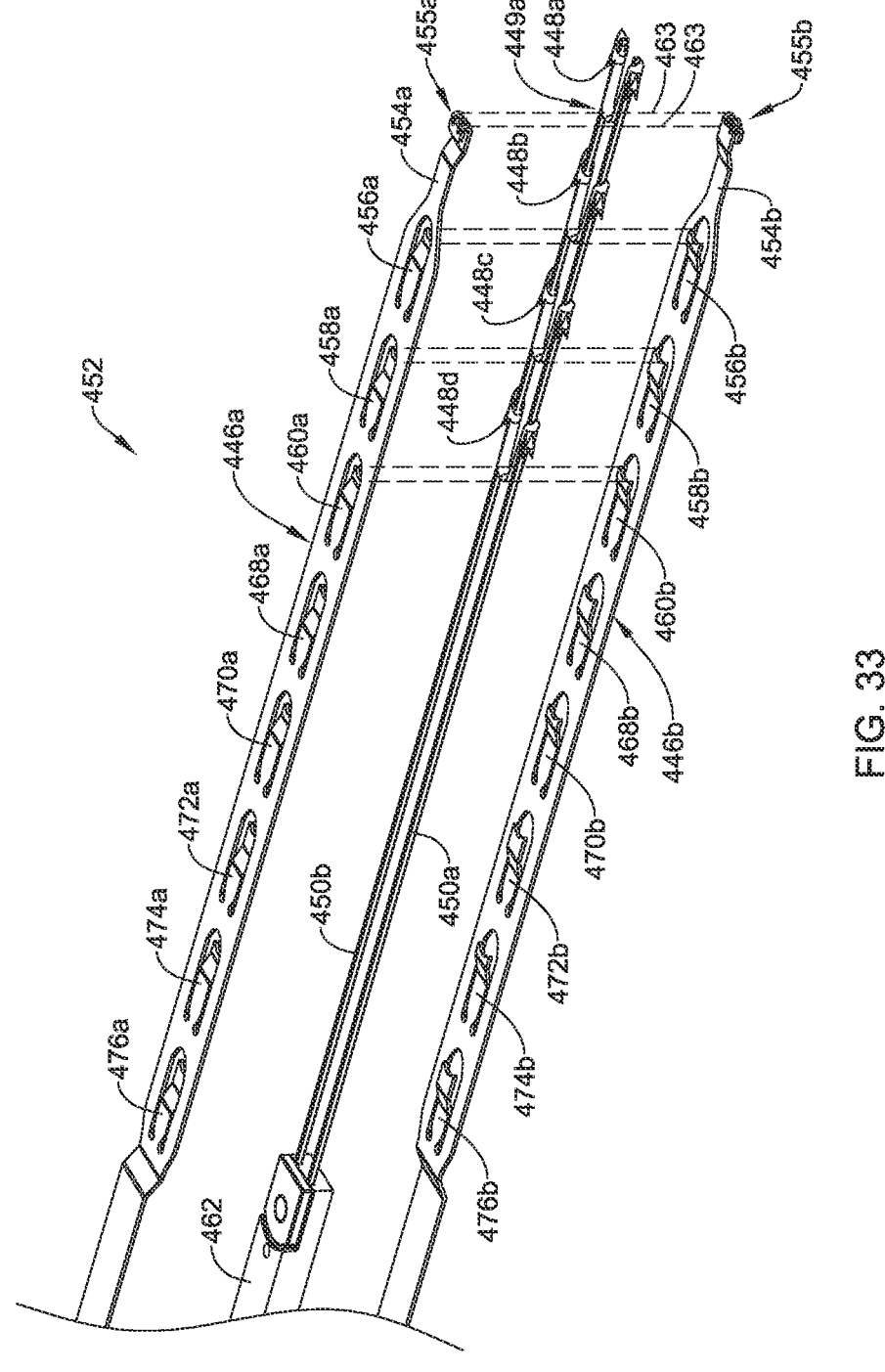
FIG. 33 illustrates a portion of the implant delivery device shown in FIG. 32.

FIG. 33 illustrates an exploded view of the fixation member actuation assembly 452. As described herein, the fixation member actuation assembly 452 may be positioned within the lumen of the outer shaft 442. Like the fixation member actuation assembly 52 described herein, the fixation member actuation assembly 452 may include several components, which collectively, work together to deploy fixation members (e.g., staples) out the distal end of the shaft assembly 429.

FIG. 33 illustrates that the fixation member actuation assembly 452 may include a first longitudinal member 446a, such as a first longitudinal beam, and a second longitudinal member 446b, such as a second longitudinal beam. In some examples, the first longitudinal member 446a and the second longitudinal member 446b may be referred to as a first beam 446a and a second beam 446b, respectively. The first longitudinal member 446a and the second longitudinal member 446b may extend through the lumen of the outer shaft 442 and attach to one or more components of the handle 479.

Additionally, FIG. 33 illustrates that the shaft assembly 429 may further include one or more "rails" which may be attached to an actuation shaft 462 and extend distally therefrom. The rails may extend parallel to a longitudinal axis of the actuation shaft 462. The rails may be fixed relative to the actuation shaft 462 such that the rails move longitudinally with the actuation shaft 462 (i.e., the rails may move in unison with the actuation shaft 462). The rails may include a first rail 450a and a second rail 450b. It can further be appreciated that the first rail 450a and the second rail 450b are generally longitudinal members which extend from the actuation shaft 462 distally through the lumen of the outer shaft 442. As will be discussed in greater detail below, the first rail 450a and the second rail 450b generally extend substantially parallel to one another through the lumen of the outer shaft 442, and thus may extend parallel to the central longitudinal axis of the outer shaft 442. The first and second rails 450a/450b and the actuation shaft 462 may be positioned between the first longitudinal member 446a and the second longitudinal member 446b.

FIG. 33 further illustrates that one or more fixation members 448a/448b/448c/448d (e.g., staples) may be threaded onto the first rail 450b and the second rail 450a. The fixation members 448a/448b/448c/448d may be similar in form and function to other fixation members described herein (e.g., the fixation members 48a/48b/48c/48d). For example, the fixation members 448a/448b/448c/448d may be staples having a first anchor portion having a pointed distal tip, a second anchor portion having a pointed distal tip, and a proximal portion extending between the proximal end regions of the first and second anchor portions. Thus, the first rail 450a may extend through a passage of the first anchor portion of each staple and the second rail 450b may extend through a passage of the second anchor portion of each staple (similar to that shown in FIG. 7 with respect to the stapling instrument 32). The staples may be oriented in longitudinal alignment with the longitudinal axis of the outer shaft 442 with the distal points of the staples pointed toward the distal end of the outer shaft 442.

Further, as shown in FIG. 33, the fixation members 448a/448b/448c/448d may be spaced away from one another along the longitudinal axis of the outer shaft 442 such that adjacent fixation members 448a/448b/448c/448d do not directly contact one another. It can be appreciated from FIG. 33 that the fixation members 448a/448b/448c/448d may be spaced apart from one another while threaded onto the first rail 450a and the second rail 450b. As such, the stapling instrument 432 may be initially loaded with a plurality of fixation members, such as four or more staples, six or more staples, or eight or more staples for sequential deployment from the stapling instrument 432. As will be discussed in greater detail below, the fixation members 448a/448b/448c/448d may be sequentially advanced out of the distal end (e.g., through the tines 440) of the outer shaft 442 as the fixation member actuation assembly 452 is manipulated via the handle 479 (shown in FIG. 32).

FIG. 33 further illustrates the fixation members 448*a*/ 448*b*/448*c*/448*d* threaded onto the first rail 450*a* and the second rail 450*b*. Like that described herein with respect to FIG. 6, it can be appreciated that, in some examples, each of the fixation members 448*a*/448*b*/448*c*/448*d* may include a first aperture extending through a first anchor portion of a fixation member and a second aperture extending through a second anchor portion of a fixation member through which the first rail 450*a* and the second rail 450*b* may extend, respectively. FIG. 33 further shows that the first, second, third and fourth fixation members 448*a*/448*b*/448*c*/448*d* may be spaced away from one another along the longitudinal axis. It can be appreciated that each of the fixation members 448*a*/448*b*/448*c*/448*d* may slide along the first rail 450*a* and the second rail 450*b*.

As described above with respect to the fixation member actuation assembly 52, the fixation member actuation assembly 452 may be designed to cyclically advance the fixation members 448*a*/448*b*/448*c*/448*d* distally along the first rail 450*a* and the second rail 450*b* such that the fixation members 448*a*/448*b*/448*c*/448*d* may be sequentially deployed out of the distal end of the outer shaft 442. FIG. 33 illustrates that the first longitudinal member 446*a* and the second longitudinal member 446*b* may include one or more features that facilitate the advancement of the fixation members 448*a*/448*b*/448*c*/448*d* along the first rail 450*a* and the second rail 450*b*. For example, FIG. 33 illustrates that the first longitudinal member 446*a* may include engagement portions 454*a*/456*a*/458*a*/460*a* (e.g., engagement tabs) which may be designed to engage a proximal end region of the first fixation member 448*a*, the second fixation member 448*b*, the third fixation member 448*c*, and the fourth fixation member 448*d*, respectively. In particular, FIG. 33 illustrates that the first longitudinal member 446*a* may include an engagement portion 454*a* (e.g., an engagement tab) which includes a distal end region 455*a* designed to engage a proximal end 449*a* of the fixation member 448*a*.

As described herein, FIG. 33 illustrates the first longitudinal member 446*a* having engagement portions 454*a*/456*a*/ 458*a*/460*a*, each of which are disposed and aligned along the first longitudinal member 446*a*. The first longitudinal member 446*a* may have an engagement portion for each fixation member initially loaded into the stapling instrument 432. It can be appreciated that FIG. 33 illustrates that the longitudinal member 446*a* may include four engagement portions (e.g., 454*a*/456*a*/458*a*/460*a*) corresponding to four fixation members (e.g., 448*a*/448*b*/448*c*/448*d*). Moreover, the longitudinal member 446*a* may include additional engagement portions corresponding to additional fixation members. For example, the longitudinal member 446*a* shown in FIG. 33 includes nine engagement portions (454*a*/456*a*/458*a*/460*a*/ 468*a*/470*a*/472*a*/474*a*/476*a*). However, for simplicity, the discussion herein focuses on the four engagement portions (454*a*/456*a*/458*a*/460*a*) corresponding to the four fixation members (448*a*/448*b*/448*c*/448*d*) depicted. However, the remainder of the engagement portions of the longitudinal member 446*a* shown in FIG. 33 may function similarly to that of the engagement portions 454*a*/456*a*/458*a*/460*a* described herein. For example, the stapling instrument 432 may be initially loaded with nine fixation members which engage the nine engagement portions of the longitudinal member 446*a* shown in FIG. 33.

FIG. 33 further illustrates that the fixation member actuation assembly 452 may include a second longitudinal member 446*b* having engagement portions 454*b*/456*b*/458*b*/ 460*b*/468*b*/470*b*/472*b*/474*b*/476*b*, each of which are disposed and aligned along the second longitudinal member

446*b*. Like the first longitudinal member 446*a*, the second longitudinal member 446*b* may have an engagement portion for each fixation member initially loaded into the stapling instrument 432.

FIG. 33 further illustrates the general alignment of the engagement portions 454*a*/456*a*/458*a*/460*a* of the first longitudinal member 446*a* and the engagement portions 454*b*/ 456*b*/458*b*/460*b* of the second longitudinal member 446*b* with each of the fixation members 448*a*/448*b*/448*c*/448*d*, respectively. For example, the vertical dashed lines 463 illustrate the vertical alignment of the distal end 455*a* of the engagement portion 454*a* and the distal end 455*b* of the engagement portion 454*b* with the proximal end 449*a* of the fixation member 448*a* at the same longitudinal position of the stapling instrument 432. It can be appreciated from FIG. 33 that the distal end of each of the other engagement portions 456*a*/458*a*/460*a* and the engagement portions 456*b*/458*b*/460*b* are similarly aligned with each corresponding fixation member 448*b*/448*c*/448*d* (as illustrated by the additional vertical dashed lines shown in FIG. 33). In other words, when assembled, the engagement portions 454*a*/ 456*a*/458*a*/460*a* of the first longitudinal member 446*a* and the engagement portions 454*b*/456*b*/458*b*/460*b* of the second longitudinal member 446*b* may be engaged with each of the fixation members 448*a*/448*b*/448*c*/448*d* such that proximal-to-distal advancement of the first longitudinal member 446*a* and the second longitudinal member 446*b* may push each of the fixation members 448*a*/448*b*/448*c*/448*d* along the first rail 450*a* and the second rail 450*b*.

Figure 34:
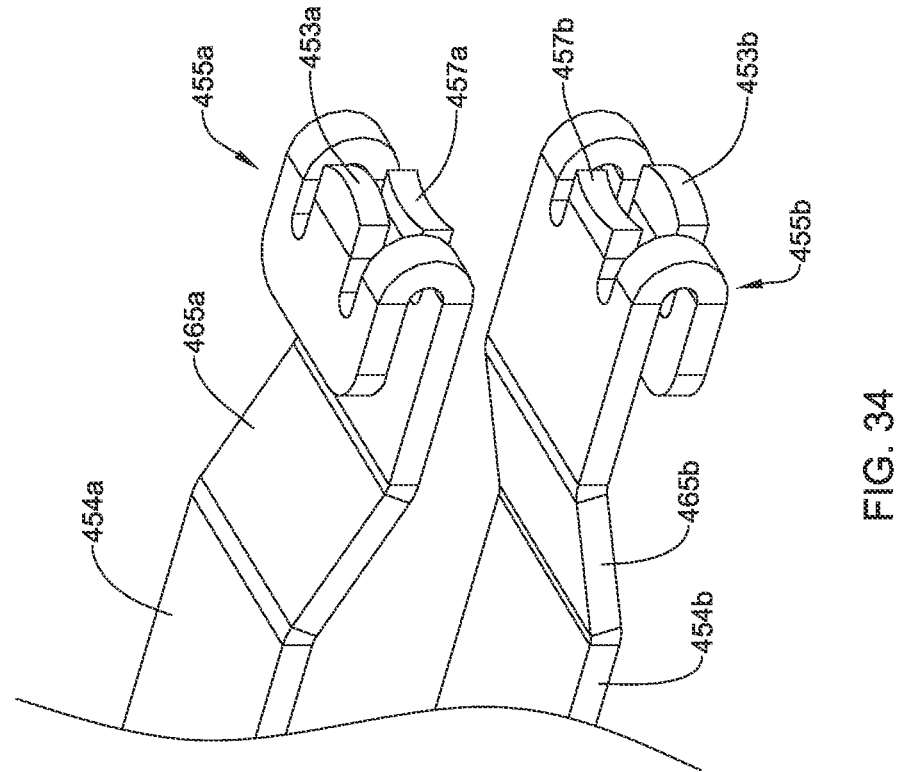
FIG. 34 illustrates another portion of the implant delivery device shown in FIG. 32.

FIG. 34 illustrates the distal ends 455*a*/455*b* of the first engagement portion 454*a* and the second engagement member 454*b*, respectively. As illustrated in FIG. 33, the distal end 455*a* of the first engagement portion 454*a* may include a first engagement face 457*a* and a first alignment tab 453*a*. Similarly, the distal end 455*b* of the second engagement portion 454*b* may include a second engagement face 457*b* and a second alignment tab 453*b*. It can be appreciated that each of the first engagement face 457*a* and the second engagement face 457*b* may be designed to engage the proximal end 449*a* of the fixation member 448*a*. It can be further appreciated that the angled portions 465*a*/465*b* (of the first engagement portion 454*a* and the second engagement portion 454*b*, respectively) may permit the first longitudinal member 446*a* and the second longitudinal member 446*b* to remain spaced apart from one another while also allowing both the first engagement face 457*a* and the second engagement face 457*b* to engage the proximal end 449*a* of the fixation member 448*a*.

Further, it can be appreciated that each of the first engagement face 457*a* and the second engagement face 457*b* may include a profile which is designed to mate with the profile of the proximal end region 449*a* of the fixation member 448*a*. For example, each of the first engagement face 457*a* and the second engagement face 457*b* may include a curved profile which mates with a curved profile of the proximal end region 449*a* of the fixation member 448*a*. The matching profiles of the first engagement face 457*a* and the second engagement face 457*b* with the proximal end region 449*a* of the fixation member 448*a* may allow the first engagement portion 454*a* and the second engagement portion 454*b* to transfer the necessary deployment force to the fixation member 448*a* when deploying the fixation member 448*a* out of the distal end of the outer shaft 442.

As described above, FIG. 33 further illustrates that the distal end 455*a* of the first engagement portion 454*a* may further include a first alignment tab 453*a* and the second engagement portion 454*b* may include a second alignment tab 453b. It can be appreciated that, together, the first alignment tab 453a and the second alignment tab 453b may engage opposing side surfaces, respectively, of the fixation member 448a. In other words, the first alignment tab 453a may engage the top surface of the fixation member 448a, while the second alignment tab 453b may engage the bottom surface of the fixation member 448a, thereby maintaining the fixation member 448a between the first alignment tab 453a and the second alignment tab 453b. It can be further appreciated that maintaining the first alignment member 448a between the first alignment tab 453a and the second alignment tab 453b may vertically align and stabilize the fixation member 448a with the first engagement face 457a and the second engagement face 457b. In some examples, the first alignment member 448a may be positioned between the first alignment tab 453a and the second alignment tab 453b such that approximately half of the proximal end 449a of the fixation member 448a (e.g., the upper half) will engage the first engagement face 457a and approximately half of the proximal end 449a of the fixation member 448a (e.g., the lower half) will engage the second engagement face 457b. It can be appreciated that to deploy the fixation member 448a, both the first longitudinal member 446a and the second longitudinal member 446b may be actuated together (i.e., simultaneously), whereby both the first longitudinal member 446a and the second longitudinal member 446b engage and deploy the fixation member 448a.

The first engagement portion 454a, including the first engagement face 457a and the first alignment tab 453a, may be formed as a unitary or monolithic portion of the first longitudinal member 446a. Additionally, the second engagement portion 454b, including the second engagement face 457b and the second alignment tab 453b, may be formed as a unitary or monolithic portion of the second longitudinal member 446b.

It can be appreciated that any of the engagement portions disclosed herein may include the profile of the distal ends 455a/455b of the first engagement portion 454a and the second engagement member 454b. For example, the distal ends of the engagement portions 54a/56a/58a/60a/90b/91b/92b/93b shown in FIG. 6B may include the profile of the distal ends 455a/455b illustrates in FIG. 34, if desired.

Figure 35:
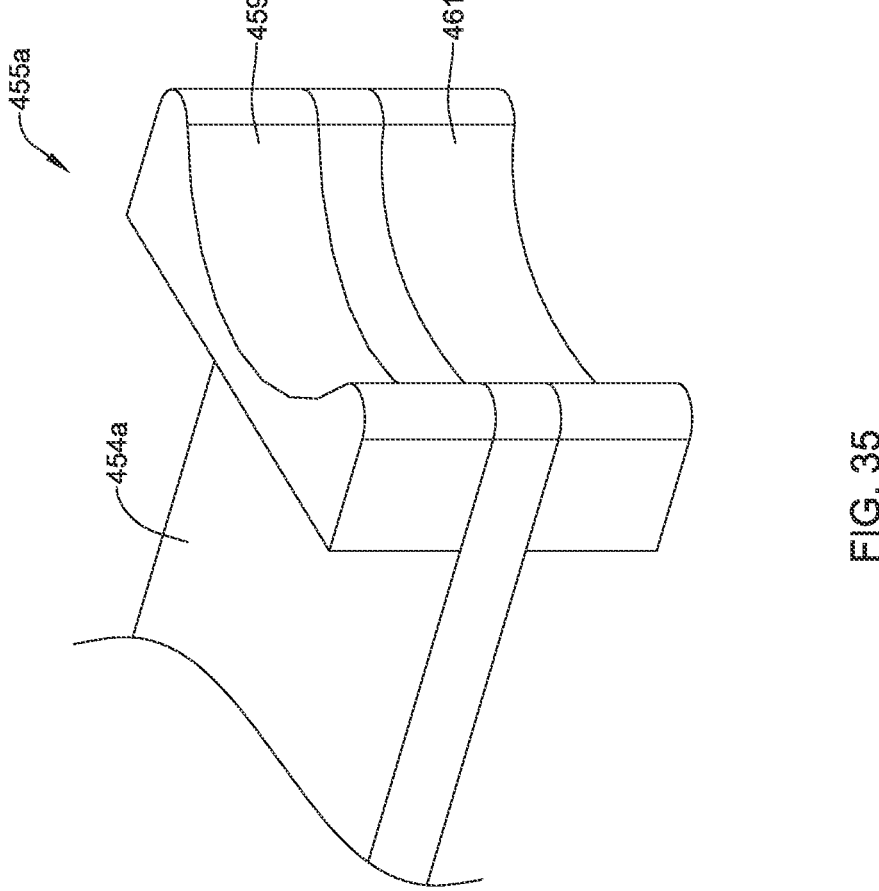
FIG. 35 illustrates an alternative configuration of a portion of the implant delivery device shown in FIG. 32.

FIG. 35 illustrates an alternative embodiment of the distal end 455a of the first longitudinal member 446a. Specifically, FIG. 35 illustrates that the distal end 455a of the first engagement portion 454a may include an upper face 459 and a lower face 461. The upper face 459 and the lower face 461 may be formed by over-molding a material onto the distal end 455a of the first longitudinal member 446a, for example. In other instances the upper face 459 and the lower face 461 may be formed by attaching the upper face 459 and the lower face 461 directly to the distal end region of the first engagement portion 454a. In yet other instances, first engagement portion 454a, the upper face 459 and the lower face 461 may be formed as a monolithic structure (e.g., the first engagement portion 454a, the upper face 459 and the lower face 461 may be formed from a single, solid piece of material).

It can be further appreciated that while FIG. 35 illustrates the distal end 455a of the first longitudinal member 446a having an upper face 459 and a lower face 461, the second longitudinal member 446b may also include an upper face and a lower face like that shown in FIG. 35 with respect to the first longitudinal member 446a. In other words, the first longitudinal member 446a, the second longitudinal member 446b, or both the first longitudinal member 446a and the second longitudinal member 446b may include an upper face and lower face as illustrated in FIG. 35.

Figure 36:
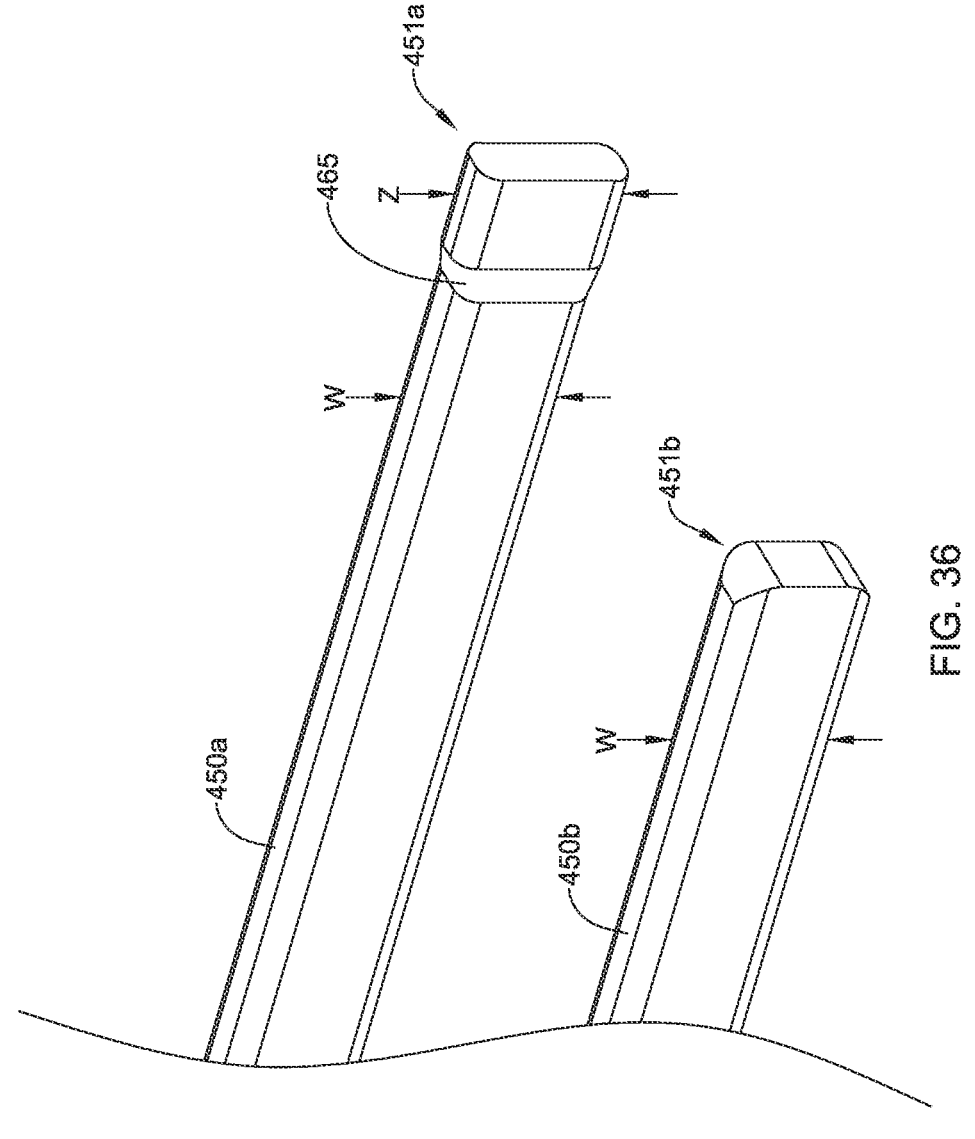
FIG. 36 illustrates another portion of the implant delivery device shown in FIG. 32.

FIG. 36 illustrates the distal end 451a of the rail 450a and the distal end 451b of the rail 450b. FIG. 36 illustrates that the rail 450b may include a width "W" measured perpendicular to the longitudinal axis. The width W of the rail 450b may extend the entire length of the rail 450b. Additionally, FIG. 36 illustrates that the rail 450a may also include a width W measured perpendicular to the longitudinal axis of the rail 450a. The width W of the rail 450a may be consistent along a majority of the length of the rail 450a.

However, as illustrated in FIG. 36, the distal end 451a of the rail 450a may include a taper 465 which extends from a portion of the rail 450a having a width "W" to an enlarged portion having a width "Z" (also measured perpendicular to the longitudinal axis of the rail 450a). As illustrated in FIG. 36, the width Z is larger than the width of the rail 450a immediately proximal of the taper 465. It can be appreciated that the width Z of the distal end 451a of the rail 450a may be designed to provide an interface fit with an aperture in the first fixation member 448a. It can be further appreciated that the entire rail 450a (including the enlarged distal end 451a) may be formed as a monolithic structure (e.g., the rail 450a including the enlarged distal end 451a) are formed from a single material. Furthermore, in some instances the first rail 450a may be formed as a monolithic structure with the second rail 450b, such as including a bent region at the proximal end of the first rail 450a and the second rail 450b. The bent region (not shown) may be located between and connect the proximal ends of the first rail 450a and the second rail 450b.

Figure 37:
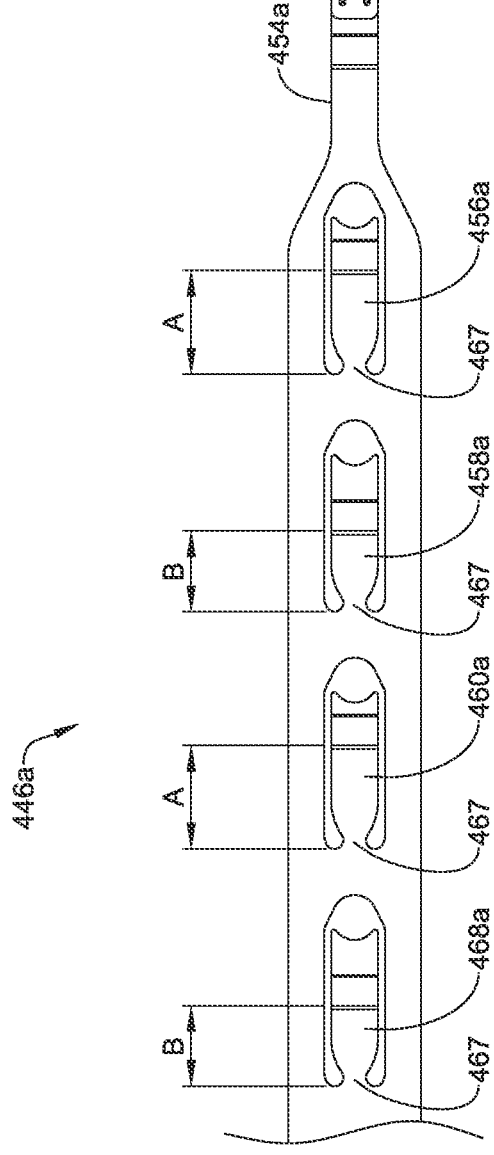
FIG. 37 illustrates another portion of the implant delivery device shown in FIG. 32.

FIG. 37 illustrates a portion of the first longitudinal member 446a. Specifically, FIG. 37 illustrates a top view of the first longitudinal member 446a having the first engagement portion 454a, the second engagement portion 456a, the third engagement portion 458a, the fourth engagement portion 460a and a fifth engagement portion 468a. Referring back to FIG. 33, it can be appreciated the first longitudinal member 446a may further include a sixth engagement portion 470a, a seventh engagement portion 472a, an eighth engagement portion 474a and a ninth engagement portion 476a. However, for simplicity, FIG. 37 illustrates the first, second, third, fourth and fifth portion members.

FIG. 37 further illustrates that the second engagement portion 456a may include a beam length "A," measured from a proximal attachment region and extend distally to a point whereby the second engagement portion 456a angles downward toward the rails 450a/450b (FIG. 33 illustrates a perspective view of the portion of each engagement portion angling downward toward the rails 450a/450b). Similarly, FIG. 37 illustrates the third engagement portion 458a may include a beam length "B." Like the second engagement portion, the length B may be measured from a proximal attachment region and extend distally to a point whereby the third engagement portion 458a angles downward toward the rails 450a/450b. However, FIG. 37 illustrates the beam length A may be longer than the beam length B. Additionally, FIG. 37 illustrates that the beam length for the fourth engagement portion 460a may be equal to the beam length A of the second engagement portion 456a while the beam length for the fifth engagement portion 468a may be equal to the beam length B of the third engagement portion 458a. Further, referring to FIG. 33, in some examples, the beam length for the second engagement portion 456a, the fourth engagement portion 460a, the sixth engagement portion 470a and the eighth engagement portion 474a may all be equal (e.g., they may all have a beam length A), while the beam length for the third engagement portion 458a, the fifth engagement portion 468a, the seventh engagement portion 472a and the ninth engagement portion 476a may all be equal (e.g., they may all have a beam length B). Thus the beam length of some of the engagement portions may be different than the beam length of others of the engagement portions. For example, the beam lengths may alternate along the length of the first longitudinal member 446a, with one engagement portion having a beam length A located between adjacent engagement portions have a beam length B. Likewise, one engagement portion having a beam length B may be located between adjacent engagement portions having a beam length A.

Additionally, it can be appreciated the beam lengths for the engagement portions (e.g., 456b/458b/460b . . . 476b) of the second longitudinal member 446b may be equal to the beam lengths of their corresponding engagement portions located on the first longitudinal member 446a. For example, referring to the second longitudinal member 446b, the beam length for the second engagement portion 456b, the fourth engagement portion 460b, the sixth engagement portion 470b and the eighth engagement portion 474b may all be equal (e.g., they may all have a beam length A), while the beam length for the third engagement portion 458b, the fifth engagement portion 468b, the seventh engagement portion 472b and the ninth engagement portion 476b may all be equal (e.g., they may all have a beam length B).

It can further be appreciated that varying the beam lengths among the engagement portions for the first longitudinal member 446a and the second longitudinal member 446b (e.g., varying the beam lengths for every other engagement portion pair of the first longitudinal member 446a and the second longitudinal member 446b) may reduce the overall actuation force generated by the first longitudinal member 446a and the second longitudinal member 446b as the engagement portions pass (and flex upward and over) the fixation members. For example, during an actuation cycle, rather than having all the engagement portions contact (and flex upward and over) the remaining fixation members at the same time, the engagement portions shown in FIG. 33 with the relatively shorter beam length B (e.g., the third, fifth, seventh and ninth engagement portions) may contact (and flex) over approximately half of the fixation members prior to the engagement portions having a relatively longer beam length A (e.g., second, fourth, sixth and eighth engagement portions). It can be appreciated that designing the beam lengths of the engagement portions to interact with the fixation members at staggered intervals may require less force for each longitudinal member 446a/446b to perform the actuation cycle.

Additionally, FIG. 33 and FIG. 37 illustrate that each engagement portion (456a, 456b/458a/458b, etc.) of the first longitudinal member and the second longitudinal member 446a/446b may include a necked-down region 467 at the base of the engagement portion. The necked-down region 467 may be defined as portion of each engagement portion that has a narrower width than a remainder of the engagement portion. It can be appreciated that the necked-down regions 467 further reduce the force required for each individual engagement portion (456a, 456b, 458a, 458b, etc.) of the first longitudinal member and the second longitudinal member 446a/446b to flex upward and over the fixation members during an actuation cycle.

In some examples, each of the first longitudinal member 446a and/or the second longitudinal member 446b may be constructed from 304 stainless steel having a raw material yield strength of 160-185 ksi per ASTM 666. Constructing the first longitudinal member 446a and/or the second longitudinal member 446b from 304 stainless steel having a raw material yield strength of 160-185 ksi per ASTM 666 may provide each of the first longitudinal member 446a and the second longitudinal member 446b with enough flexibility to limit the retraction forces during an actuation cycle while also providing sufficient column strength to advance the fixation members through an implant an into tissue. The longitudinal members of other embodiments described herein may also be constructed of 304 stainless steel having a raw material yield strength of 160-185 ksi per ASTM 666.

Figure 38:
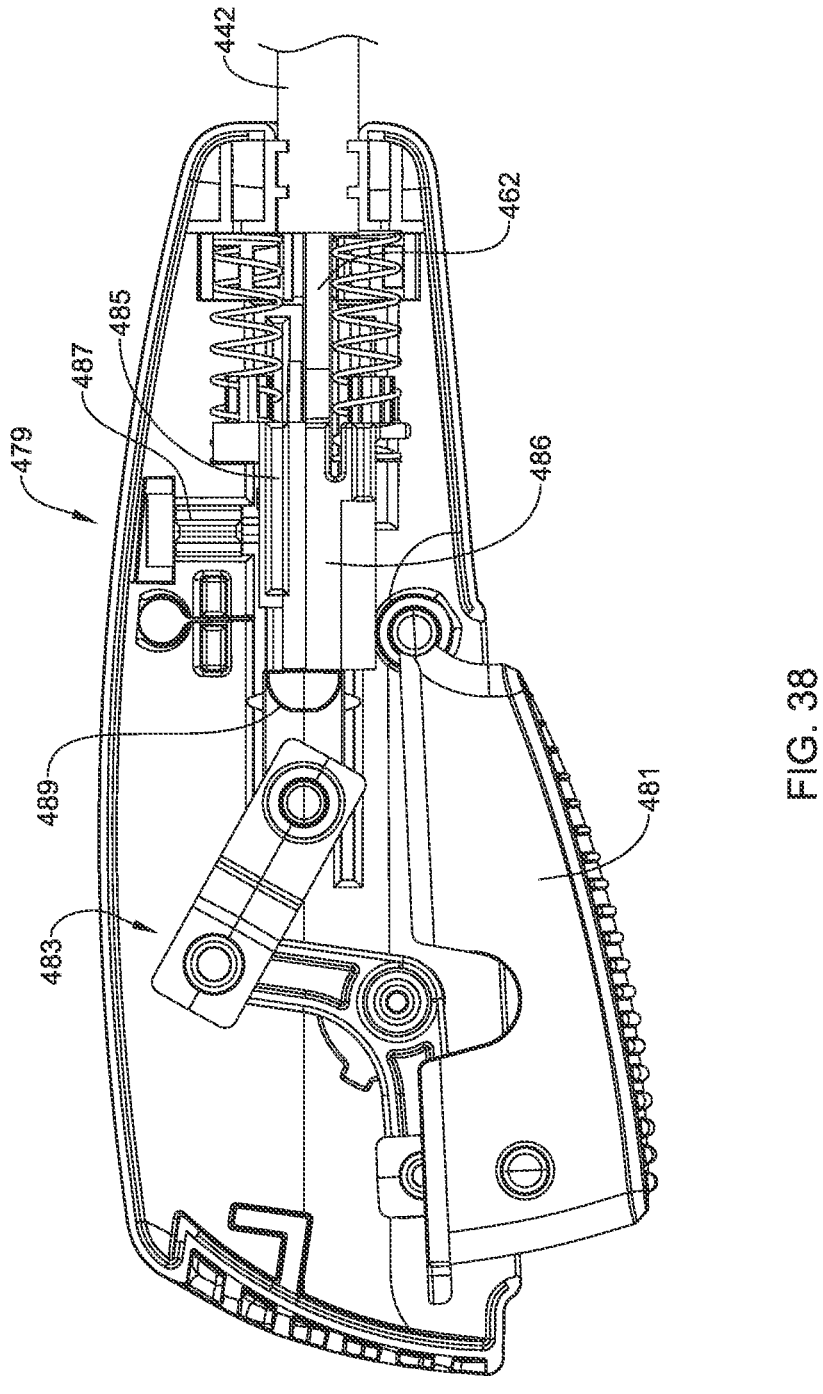
FIGS. 38-40 illustrate the implant delivery device shown in FIG. 32 being actuated in a sequence of steps to deliver a fixation member.

FIGS. 38-41 illustrate components of the handle 479. The handle 479 is described in relation to the stapling instrument 432, however the handle 479 may be incorporated with any other configuration of a stapling instrument described herein. FIG. 38 illustrates a cross-section of the inner components of the handle 479. Further, FIG. 38 illustrates the lever 481, whereby the lever 481 is coupled to a linkage assembly 483. The linkage assembly 483 may include a lead link 489 that engages a first deployment member 485 and a second deployment member 486. For example, the distal end of the lead link 489 may directly contact and engage the proximal ends of both the first deployment member 485 and the second deployment member 486. Additionally, the first deployment member 485 and/or the second deployment member 486 may be coupled to the actuation shaft 462 (which may extend through the outer shaft 442). For example, the first deployment member 485 may be fixedly coupled to each of the first longitudinal member 446a, the first rail 450a, and the second rail 450b, and moveable therewith. The second deployment member 486 may be fixedly coupled to the second longitudinal member 446b and moveable therewith. Further, FIG. 38 illustrates that the handle 479 may include a cam member 487 positioned proximal to the proximal end of the first deployment member 485. As will be described in greater detail below, the cam member 487 may be designed to temporarily engage the first deployment member 485 to prevent proximal movement thereof.

Figure 39:
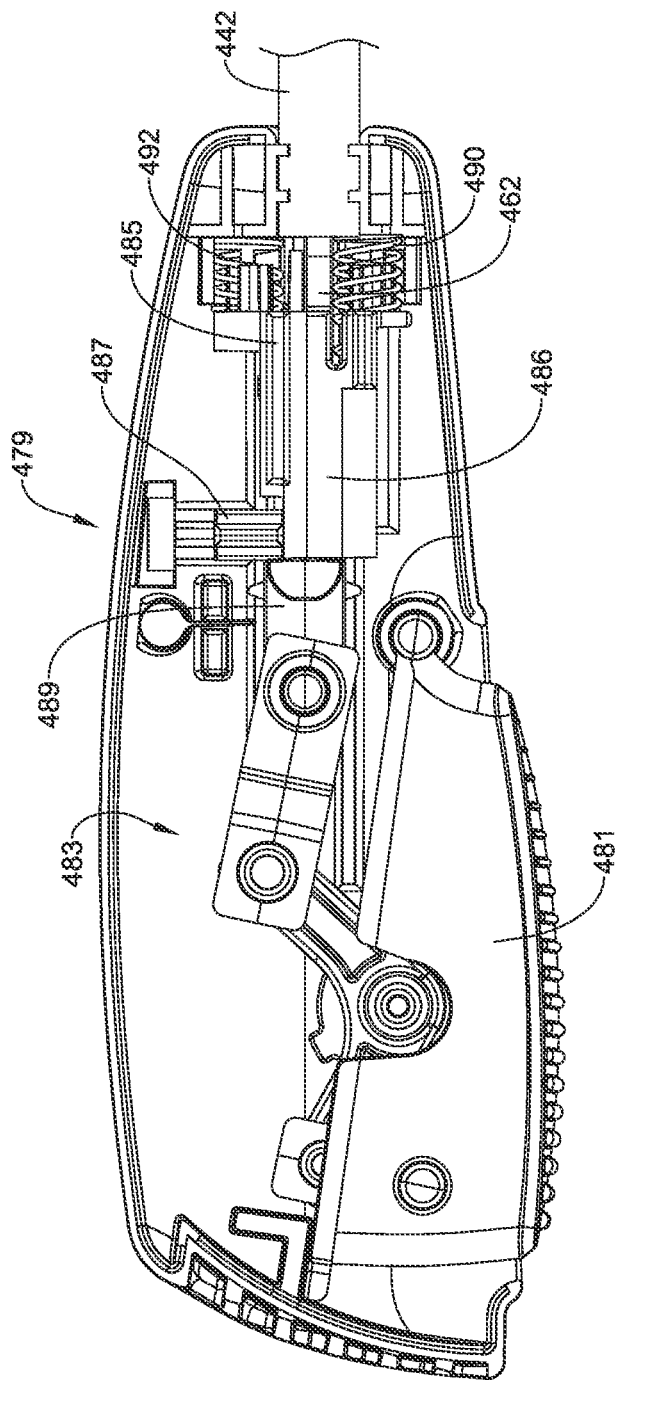
Figure 40:
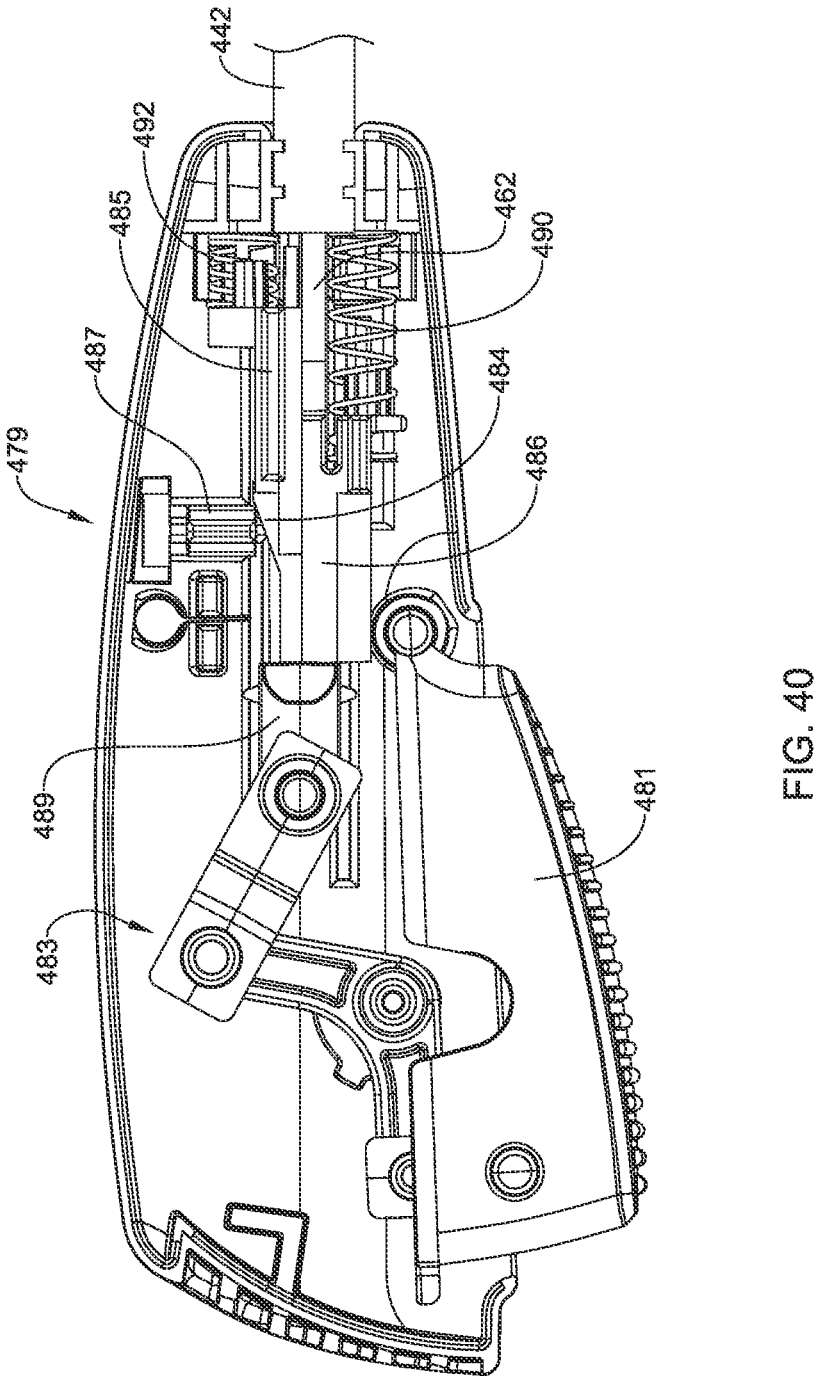

FIGS. 38-40 illustrate the coordinated movement of various inner components within the handle 479 which permit the fixation member actuation assembly 452 to sequentially deploy the fixation members from the outer shaft 442. In other words, the mechanical movement of the inner components of the actuation mechanism within the handle 479, as shown in FIGS. 38-40, correspond to the cycling of the first longitudinal member 446a, the second longitudinal member 446b, the first rail 450a and the second rail 450b to sequentially deploy the fixation members from the outer shaft 442. It can be appreciated that, prior to actuating the lever 481, a clinician may initially position the handle 479 adjacent a target site and push the handle 479 into the target site, thereby driving the tines 440 through the implant 12 and into the target tissue (e.g., humeral head or tendon). This step is described above with respect to FIG. 13 in which the actuation mechanism is in the ready state. FIGS. 38-40 describe the actuation of the components of the handle 479 after the initial penetration of the tines 440 at the target site (e.g., tendon).

FIG. 39 illustrates the squeezing of the lever 481 of the handle 479. It can be appreciated that the actuation of the linkage assembly 483 may result in a proximal-to-distal movement of both the first deployment member 485 and the second deployment member 486, thereby moving the first longitudinal member 446a, the second longitudinal member 446b, the first rail 450a, and the second rail 450b distally in unison. Accordingly, the proximal-to-distal movement of the first and second deployment members 485/486 may translate the actuation shaft 462, having the rails 450a/450b secured thereto, in a distal direction. It can be appreciated that the distal movement of the actuation shaft 462 may shift each of the fixation members in a distal direction relative to the outer shaft 442. The distal movement of the fixation member actuation assembly 452 may deploy the leading (distalmost) fixation member out of the outer shaft 442.

Additionally, FIG. 39 illustrates that the handle 479 may include a first spring 490 coupled to a distal end of the second deployment member 486 and a second spring 492 coupled to the distal end of the first deployment member 485. Further, FIG. 39 illustrates that the proximal-to-distal movement of the first and second deployment members 485/486 may compress both the first spring 490 and the second spring 492.

Additionally, FIG. 39 illustrates that the proximal-to-distal movement of the first and second deployment members 485/486 allows the cam member 487 to translate vertically downward after the distal end of the first deployment member 485 has cleared the "bottom" (e.g., lower end) of the cam member 487. In some instances, the handle 479 may include a third spring which may be coupled to the "top" (e.g., upper end) of the cam member 487. It can be appreciated that the third spring may expand and impart a force onto the cam member 487, whereby the expansion of the spring translates the cam member 487 downward after the first deployment member 485 has cleared the bottom end of the cam member 487. As will be discussed in greater detail with respect to FIG. 40, after the cam member 487 translates downward (e.g., is pushed downward by the third spring), it may engage the proximal end of the first deployment member 485, thereby providing a temporary resistance to the proximal retraction of the first deployment member 485.

FIG. 40 illustrates the lever 481 being released after squeezing the lever 481 to deploy the initial leading fixation member out of the outer shaft 442. This step begins the "cycling" of the fixation member actuation assembly 452 back to the proximal position, or ready state, to load a subsequent fixation member in the leading position of the fixation member actuation assembly 452 for subsequent deployment from the outer shaft 442. As illustrated in FIG. 40, as the lever 481 is released, the linkage assembly 483 shifts such that the second deployment member 486 retracts in a proximal direction with respect to the first deployment member 485. It can be appreciated that after the lever 481 is released, the first spring 492 may expand, thereby pushing the second deployment member 486 in a distal-to-proximal direction. Further, it can be appreciated that the retraction of the second deployment member 486 corresponds to the proximal retraction of the second longitudinal member 446b back to its proximal position, as described above.

Figure 41:
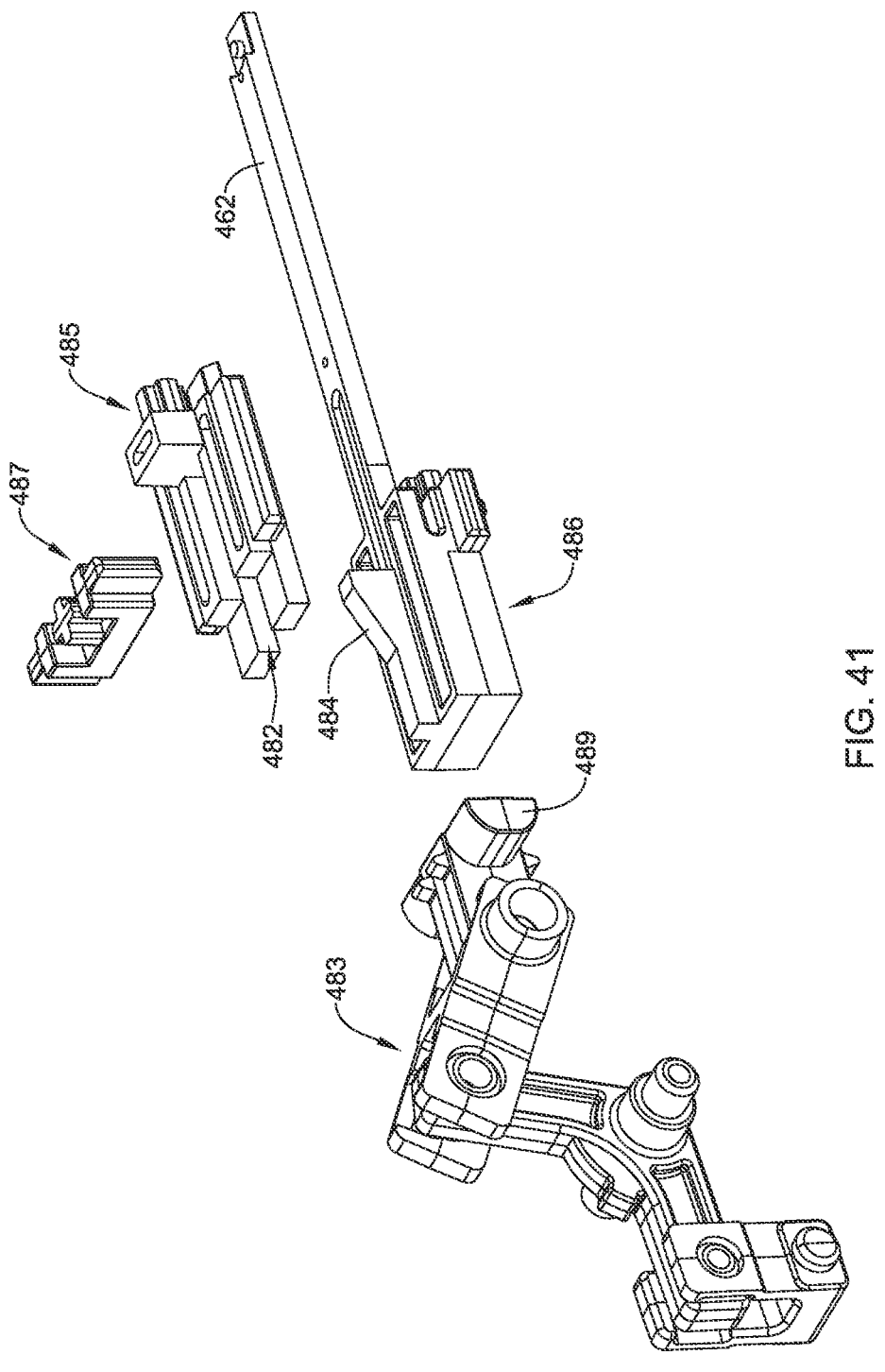
FIG. 41 illustrates another portion of the delivery device shown in FIG. 32.

Further, FIG. 40 illustrates that the second deployment member 486 may include an angled face 484 (e.g., an angled ramp) which is designed to engage the cam member 487 as the second deployment member 486 translates in a distal-to-proximal direction. As illustrated in FIG. 41, the angled face 484 may translate within a slot 482 located in the first deployment member 485. It can be appreciated that after the lever 481 is released, the first spring 490 and the second spring 492 will expand, thereby imparting forces onto the first and second deployment members 485/486, whereby the spring forces may translate the first and second deployment members 485/486 proximally.

It can be further appreciated from FIG. 40 that as the second deployment member 486 translates in a distal-toproximal direction (via the expansive force imparted onto the second deployment member 486 by the first spring 490), the angled face 484 may engage the cam member 487, thereby driving the cam member 487 vertically upward. It can be appreciated that to drive the cam member 487 vertically upward, the force imparted by the angled ramp 484 of the second deployment member 486 must overcome the downward force imparted by the third spring onto the cam member 487 (e.g., the upward force vector imparted by the angled face 484 must be greater than the downward force of imparted by the third spring onto the cam member 487). It can be further appreciated that as the angled face 484 will, over a time period, translate proximally such that it eventually translates the cam member 484 vertically upward to a position in which it no longer engages (i.e., clears) the proximal end of the first deployment member 485. At this point, the first deployment member 485 will be free to translate proximally back to its starting proximal position. Hence, it can be appreciated from the above discussion that the interaction of the angled face 484 of the second deployment member 486 may create a delay between the time point at which the second deployment member 486 is proximally retracted and reset compared to the time point at which the first deployment member 485 is proximally retracted and reset. In other words, the second deployment member 486 will be proximally reset prior to the first deployment member 485 being proximally reset during each actuation cycle.

Further, it can be appreciated that after the second deployment member 486 is proximally reset (which proximally retracts the second longitudinal member 446b), the first longitudinal member 446a, the first rail 450a and the second rail 450b remain in a stationary position as the second longitudinal member 446b is retracted. Moreover, the proximal retraction of the first deployment member 485 may permit the first longitudinal member 446a, the first rail 450a and the second rail 450b of the actuation assembly 452 to proximally retract in unison back to their proximal position in the ready state, thereby completing a full cycle of advancing the fixation members within the outer shaft 442 to a position in which a successive fixation member is ready to be deployed at the target site. As described above, it can be appreciated that as the first longitudinal member 446a, the first rail 450a and the second rail 450b are proximally retracted back to their proximal position, the second longitudinal member 446b may remain stationary in its proximal position, thereby maintaining the position of the fixation members within the lumen of the outer shaft 442.

FIG. 41 illustrates a perspective view of various components discussed above which permit the sequential proximal resetting of the first deployment member 485 and the second deployment member 486. For example, FIG. 41 illustrates the linkage assembly, including the lead link 489. FIG. 41 also illustrates the second deployment member 486, whereby the first deployment member 485 includes the angled face 484 (e.g., angled ramp) and the actuation shaft 462. FIG. 41 also illustrates the first deployment member 485, whereby the second deployment member includes the slot 482. As discussed above, the angled face 484 of the second deployment member 486 may translate within the slot 482 of the first deployment member 485. FIG. 41 also shows the cam member 487 which engages the first deployment member 485.

Figure 42:
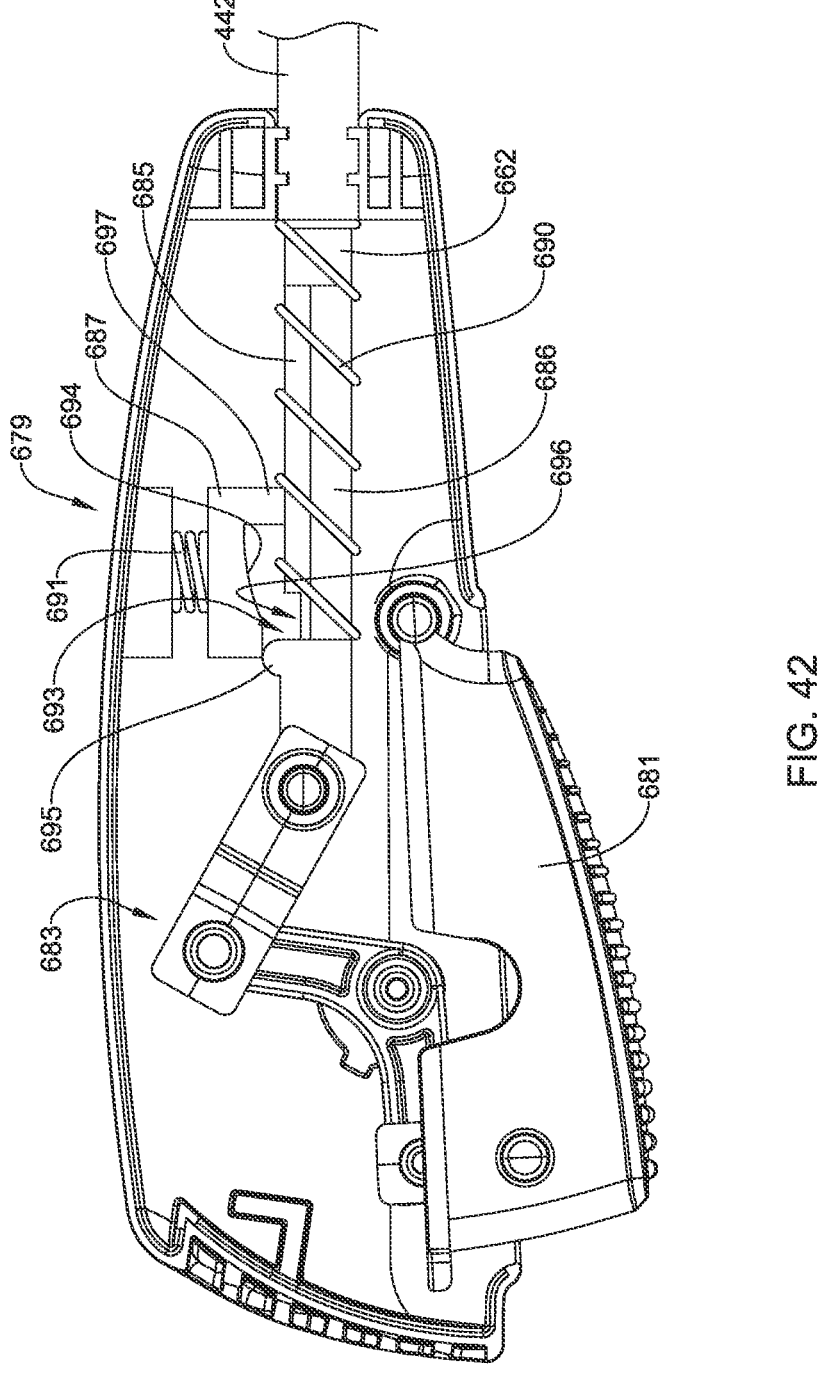
FIGS. 42-44 illustrate another example implant delivery device being actuated in a sequence of steps to deliver a fixation member.

FIG. 42 illustrates a cross-section of the inner components of another example handle 679. The handle 679 may be used in conjunction with any variation of a stapling instrument described herein. The handle 679 may be similar in form and function to the handle 479 described above. For example, the handle 679 may replace the handle 479 in FIG. 32 and operate to deploy the fixation members 448a/448b/448c/448d via engagement with the fixation member actuation assembly 452. In other words, the handle 679 may engage the outer shaft 442 and the fixation member actuation assembly 452 (including the first longitudinal member 446a, the second longitudinal member 446b, the first rail 450a and the second rail 450b) extending within the outer shaft 442 described herein. However, as will be described below, various inner components of the handle 679 which permit the fixation member actuation assembly 452 to sequentially deploy the fixation members from the outer shaft 442 are different compared to the inner components of the handle 479.

Like the handle 479 described above, FIG. 42 illustrates that the handle 679 may include a lever 681, whereby the lever 681 is coupled to a linkage assembly 683. The linkage assembly 683 may be coupled to a first deployment member 685. For example, the distal end of the linkage assembly 683 may directly contact and engage the proximal end of the first deployment member 685. Additionally, the first deployment member 685 and/or the second deployment member 686 may be coupled to an actuation shaft 662, whereby the actuation shaft 662 may be coupled to one or more components of the fixation member actuation assembly 452 (e.g., the actuation shaft 662 may be similar in form and function to the actuation shaft 462 described herein). Accordingly, the first deployment member 685 may be coupled (via the actuation shaft 662 to each of the first longitudinal member 446a, the first rail 450a, and the second rail 450b). Similarly, the second deployment member 486 may be fixedly coupled to the second longitudinal member 446b and moveable therewith. Further, FIG. 42 illustrates that the handle 679 may include a cam member 687 positioned proximal to the proximal end of the first deployment member 685. As will be described in greater detail below, the cam member 687 may be designed to temporarily engage the first deployment member 685 to prevent proximal movement thereof.

Figure 43:
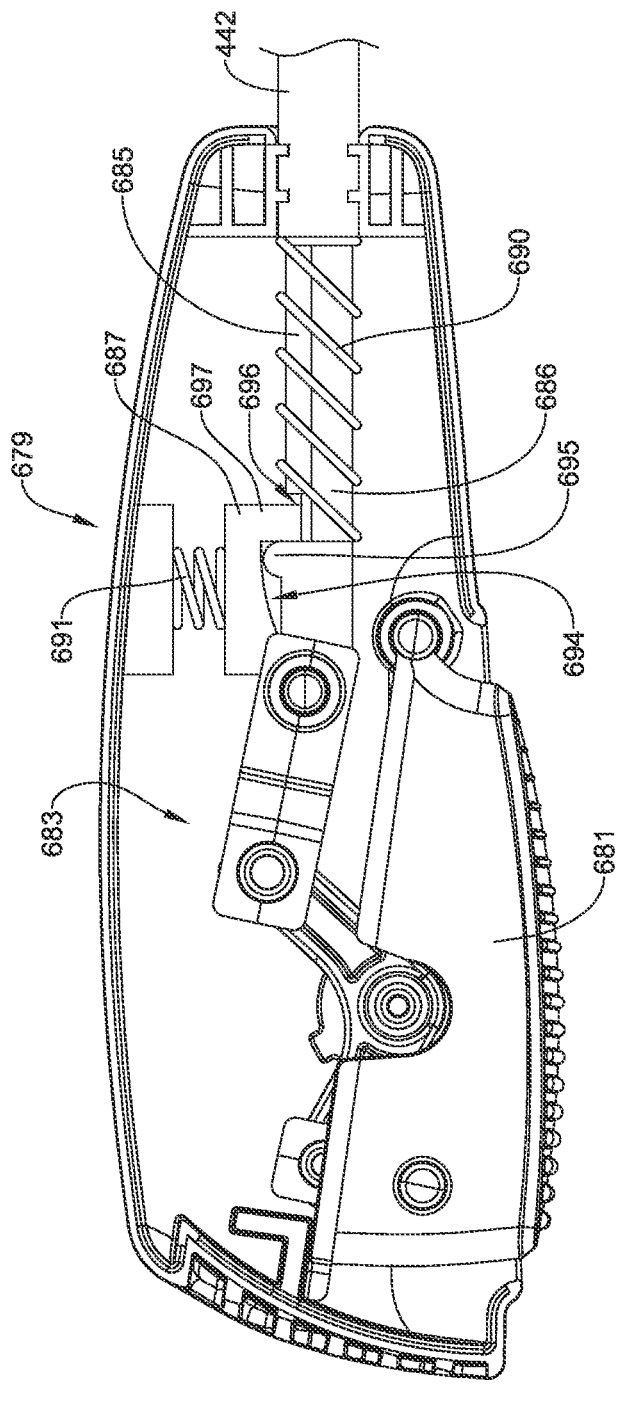
Figure 44:
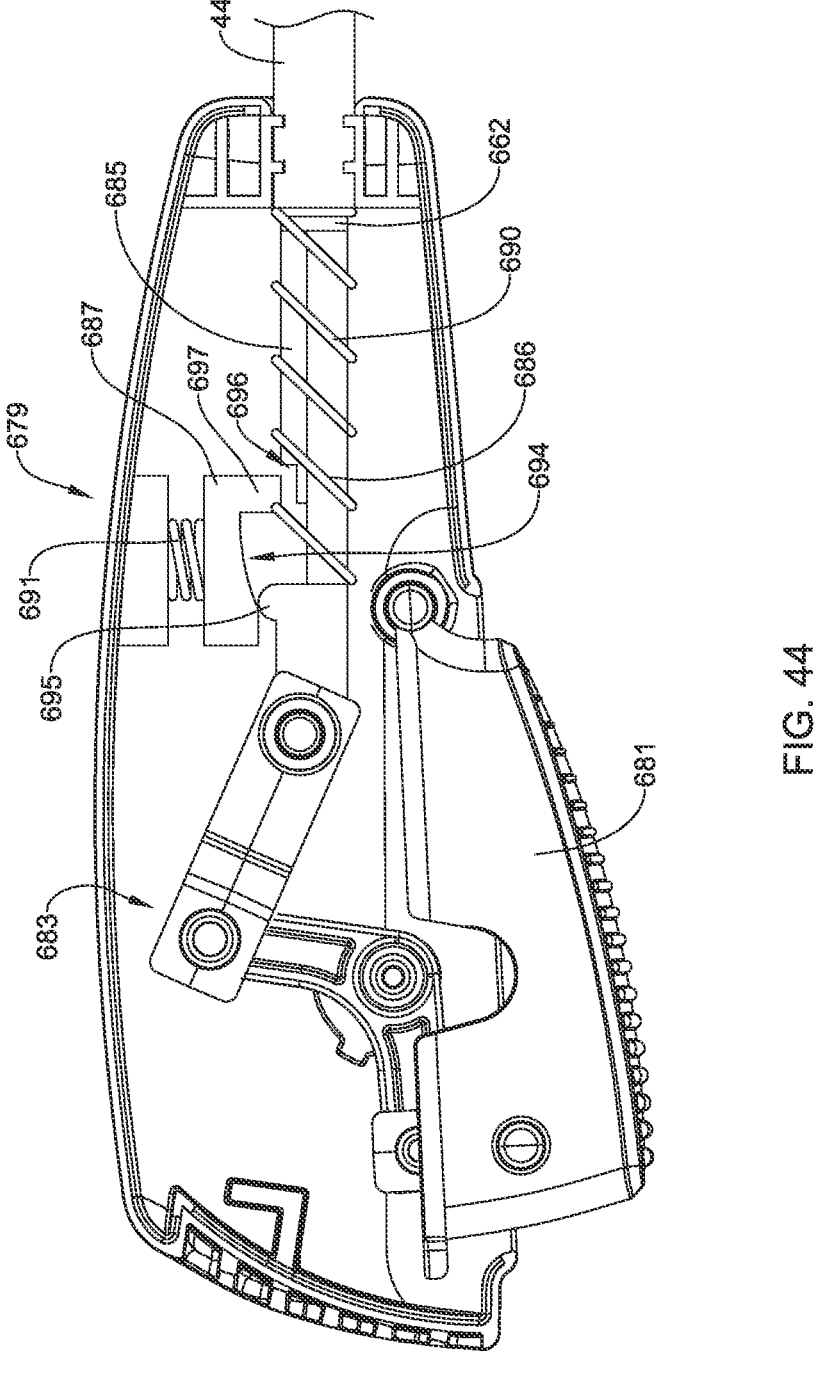

FIGS. 42-44 illustrate a cross-section of the coordinated movement of various inner components within the handle 679 design. In other words, the mechanical movement of the inner components of the actuation mechanism within the handle 679, as shown in FIGS. 42-44, correspond to the cycling of the first longitudinal member 446a, the second longitudinal member 446b, the first rail 450a and the second rail 450b to sequentially deploy the fixation members from the outer shaft 442. It can be appreciated that, prior to actuating the lever 681, a clinician may initially position the handle 679 adjacent a target site and push the handle 679 into the target site, thereby driving the tines 440 through the implant 12 and into the target tissue (e.g., humeral head or tendon). This step is described above with respect to FIG. 13 in which the actuation mechanism is in the ready state. FIGS. 42-44 describe the actuation of the components of the handle 679 after the initial penetration of the tines 440 at the target site (e.g., tendon).

FIGS. 42-43 illustrate the squeezing of the lever 681 of the handle 679. It can be appreciated that the actuation of the linkage assembly 683 may result in a proximal-to-distal movement of both the first deployment member 685 and the second deployment member 686, thereby moving the first longitudinal member 446a, the second longitudinal member 446b, the first rail 450a, and the second rail 450b distally in unison. As shown in FIG. 43, the proximal end region of the first deployment member 685 and the proximal end region of the second deployment member 686 may engage a distal face 693 of the linkage assembly 683, and therefore, the proximal-to-distal translation of the distal face 693 of the linkage assembly 683 may translate both the first deployment member 685 and the second deployment member 686 in unison in a proximal-to-distal direction. Additionally, it can be appreciated that the proximal-to-distal movement of the first and second deployment members 685/686 may translate the actuation shaft 662, having the rails 450a/450b secured thereto, in a distal direction. It can be appreciated that the distal movement of the actuation shaft 662 may shift each of the fixation members in a distal direction relative to the outer shaft 442. The distal movement of the fixation member actuation assembly 452 may deploy the leading fixation member out of the outer shaft 442.

Additionally, FIG. 43 illustrates that the handle 679 may include a first spring 690 coupled to both the first deployment member 685 and the second deployment member 686. Further, FIG. 43 illustrates that the proximal-to-distal movement of the first and second deployment members 685/686 may compress the first spring 690.

FIG. 43 illustrates that the proximal-to-distal movement of the first and second deployment members 685/686 may permit the cam member 687 to translate vertically downward relative to the longitudinal axis of the handle 679. Specifically, FIG. 43 illustrates that as the second longitudinal member 686 moves in a proximal-to-distal direction, a projection 695 of the second longitudinal member 686 may follow a curved recess 694 positioned in the cam member 687. It can be appreciated that the shape of the curved recess 694 of the cam member 687 allows the cam member 687 to translate either vertically downward (when the second longitudinal member 686 translates distally) or vertically upward (when the second longitudinal member 686 translates proximally).

Additionally, it can be appreciated from FIGS. 42-43 that the proximal end of the first longitudinal member 685 may include a notched region 696, whereby the notched region 696 is designed to accept a distal end projection 697 of the cam member 687. Accordingly, it can be appreciated that as the second longitudinal member 686 is translated in a proximal-to-distal direction, it will push the first longitudinal member 685 distally to a position in which the distal end projection 697 of the cam member 687 is aligned with the notched region 696 of the first longitudinal member 685. Further, when the distal end projection 697 of the cam member 687 is aligned with the notched region 696 of the first longitudinal member 685, the cam member 687 will translate vertically downward as the distal end projection 697 "drops" into the notched region 696 of the first longitudinal member 685.

Additionally, FIG. 43 illustrates that the handle 679 may include a second spring 691 which may be coupled to the "top" (e.g., upper end) of the cam member 687. It can be appreciated that the second spring 691 may expand and impart a force onto the cam member 687, whereby the expansion of the spring 691 translates the cam member 687 downward when the distal end projection 697 drops into the notched region 696 of the first deployment member 685. It can be appreciated that after the cam member 687 translates downward (e.g., is pushed downward by the second spring 691), it may engage the proximal end of the first deployment member 685 (e.g., the distal end projection 697 engages a face of the first deployment member 685 when positioned within the notched region 696 of the first deployment member 685) thereby providing a stop to provide temporary resistance to the proximal retraction of the first deployment member 685.

FIG. 44 illustrates the lever 681 being released after squeezing the lever 681 to deploy the initial leading fixation member out of the outer shaft 442. This step begins the "cycling" of the fixation member actuation assembly 452 back to the proximal position, or ready state, to load a subsequent fixation member in the leading position of the fixation member actuation assembly 452 for subsequent deployment from the outer shaft 442. As illustrated in FIG. 44, as the lever 681 is released, the linkage assembly 683 shifts such that the second deployment member 686 retracts in a proximal direction with respect to the first deployment member 685. It can be appreciated that after the lever 681 is released, the first spring 690 may expand, thereby pushing the second deployment member 686 and the first deployment member 685 in a distal-to-proximal direction. Further, it can be appreciated that the retraction of the second deployment member 686 corresponds to the proximal retraction of the second longitudinal member 446*b* back to its proximal position, as described above.

Further, FIG. 44 illustrates that after the lever 681 is released, the first spring 690 may expand, thereby pushing the both the first deployment member 685 and the second deployment member 686 in a distal-to-proximal direction. However, as described with respect to FIG. 43, the first longitudinal member 685 may be prevented from translating proximally until the distal end projection 697 is translated vertically upward such that it clears the top surface of the first longitudinal member 685. Accordingly, FIG. 44 illustrates that as the second longitudinal member 686 translates proximally, the projection 695 contacts the surface of the curved recess 694 of the cam member 687, whereby as the projection 695 follows the curved recess 687 as it translates proximally, the shape of the curved recess 694 results in an upward, vertical translation of the cam member 687. Further, as the second longitudinal member 686 translates proximally, the distal end projection 687 of the cam member 687 will eventually translate vertically upward to a position in which it clears the top surface of the first longitudinal member 685, thereby permitting the first longitudinal member 685 to translate proximally. It can be appreciated from the above discussion that the interaction of the projection 695 of the second deployment member 686 may create a delay between the time point at which the second deployment member 686 is proximally retracted and reset compared to the time point at which the first deployment member 685 is proximally retracted and reset. In other words, the second deployment member 686 will be proximally reset prior to the first deployment member 685 being proximally reset during each actuation cycle. Further, it can be appreciated that after the second deployment member 686 is proximally reset (which proximally retracts the second longitudinal member 446*b*), the first longitudinal member 446*a*, the first rail 450*a* and the second rail 450*b* remain in a stationary position as the second longitudinal member 446*b* is retracted. Moreover, the proximal retraction of the first deployment member 685 may permit the first longitudinal member 446*a*, the first rail 450*a* and the second rail 450*b* of the actuation assembly 452 to proximally retract in unison back to their proximal position in the ready state, thereby completing a full cycle of advancing the fixation members within the outer shaft 442 to a position in which a successive fixation member is ready to be deployed at the target site. As described above, it can be appreciated that as the first longitudinal member 446*a*, the first rail 450*a* and the second rail 450*b* are proximally retracted back to their proximal position, the second longitudinal member 446*b* may remain stationary in its proximal position, thereby maintaining the position of the fixation members within the lumen of the outer shaft 442.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A fixation member delivery system, the fixation member delivery system comprising:
   an outer shaft, the outer shaft including a lumen, a proximal end region, a distal end region, a longitudinal axis, and an opening positioned at a distal end thereof;
   a handle coupled to the proximal end region of the outer shaft, the handle including an actuation mechanism;
   a plurality of fixation members arranged sequentially along the longitudinal axis and lying within a plane extending parallel to the longitudinal axis; and
   an actuation assembly positioned within the lumen of the outer shaft and coupled to the handle, the actuation assembly including:
      a first elongate member including a first plurality of engagement members disposed along the first elongate member, wherein each of the first plurality of engagement members includes an angled portion and an engagement portion extending distally from the angled portion, wherein the angled portion extends at an acute angle relative to the longitudinal axis, wherein the entire engagement portion lies within the plane, and wherein the engagement portion includes a distal end region configured to engage a proximal end of one of the fixation members; and
      a second elongate member including a second plurality of engagement members disposed along the second elongate member;
   wherein the first elongate member is actuatable in a proximal-to-distal direction relative to the outer shaft via actuation of the actuation mechanism to distally advance the plurality of fixation members in unison;
   wherein the second elongate member is held stationary as the first elongate member is actuated;
   wherein cyclical actuation of the actuation assembly is configured to incrementally move the fixation members distally to deploy each of the plurality of fixation members in sequence.

2. The fixation member delivery system of claim 1, wherein the first and second elongate members extend parallel to and are positioned on opposing sides of the longitudinal axis and parallel therewith.

3. The fixation member delivery system of claim 2, wherein a portion of each of the first plurality of engagement members extend inward toward the longitudinal axis.

4. The fixation member delivery system of claim 3, wherein a portion of each of the second plurality of engagement members extend inward toward the longitudinal axis.

5. The fixation member delivery system of claim 1, wherein the first elongate member is configured to proximally retract after actuating in a proximal-to-distal direction, and wherein the first plurality of engagement members is configured to flex away from the longitudinal axis as the first elongate member is proximally retracted.

6. The fixation member delivery system of claim 5, wherein the second plurality of engagement members is configured to flex away from the longitudinal axis.

7. The fixation member delivery system of claim 6, wherein the second elongate member prevents the plurality of fixation members from moving within the lumen of the outer shaft while the first elongate member is retracted proximally.

8. The fixation member delivery system of claim 1, wherein the plurality of fixation members are spaced away from one another along the longitudinal axis.

9. The fixation member delivery system of claim 1, wherein the plurality of fixation members are staples having a first anchor portion having a pointed distal tip, a second anchor portion having a pointed distal tip, and a bridge extending between proximal ends of the first and second anchor portions.

10. The fixation member delivery system of claim 1, wherein the actuation mechanism includes a lever and a linkage.

11. The fixation member delivery system of claim 10, wherein the linkage is coupled to a deployment member.

12. The fixation member delivery system of claim 11, wherein the deployment member is fixedly coupled to the first elongate member.

13. The fixation member delivery system of claim 1, further comprising an access sheath extending along a portion of the outer shaft.

14. The fixation member delivery system of claim 13, wherein the access sheath includes a longitudinal slot extending along an entire length of the access sheath.

15. A fixation member delivery system, comprising:
an outer shaft, the outer shaft including a lumen, a proximal end region, a distal end region, a longitudinal axis and an opening positioned at a distal end thereof;

a handle coupled to the proximal end region of the outer shaft, the handle including an actuation mechanism;
a plurality of fixation members arranged sequentially along the longitudinal axis;
an access sheath extending along a portion of the outer shaft; and
an actuation assembly positioned within the lumen of the outer shaft and coupled to the handle, the actuation assembly including:
a first elongate member including a first plurality of engagement members disposed along the first elongate member with a distal end of each engagement member of the first elongate member in engagement with a proximal end of one of the fixation members; and
a second elongate member including a second plurality of engagement members disposed along the second elongate member;
wherein the first elongate member is actuatable in a proximal-to-distal direction relative to the outer shaft via actuation of the actuation mechanism to distally advance the plurality of fixation members in unison;
wherein the second elongate member is held stationary as the first elongate member is actuated;
wherein cyclical actuation of the actuation assembly is configured to incrementally move the fixation members distally to deploy each of the plurality of fixation members in sequence;
wherein a proximal end region of the access sheath includes a finger loop to grasp in order to separate the access sheath from the outer shaft.

* * * * *